(12) United States Patent
Davis et al.

(10) Patent No.: US 11,369,483 B2
(45) Date of Patent: Jun. 28, 2022

(54) INTERVERTEBRAL DEVICES AND RELATED METHODS

(71) Applicant: Expanding Innovations, Inc., Mountain View, CA (US)

(72) Inventors: John Davis, Sunnyvale, CA (US); Al Mirel, Redwood City, CA (US)

(73) Assignee: Expanding Innovations, Inc., Mountain View, CA (US)

( * ) Notice: Subject to any disclaimer, the term of this patent is extended or adjusted under 35 U.S.C. 154(b) by 0 days.

(21) Appl. No.: 15/213,394

(22) Filed: Jul. 18, 2016

(65) Prior Publication Data

US 2018/0014944 A1   Jan. 18, 2018
US 2018/0368987 A9   Dec. 27, 2018

Related U.S. Application Data

(60) Provisional application No. 62/194,149, filed on Jul. 17, 2015.

(51) Int. Cl.
*A61F 2/44* (2006.01)
*A61F 2/30* (2006.01)
*A61F 2/46* (2006.01)

(52) U.S. Cl.
CPC .......... *A61F 2/447* (2013.01); *A61F 2/30771* (2013.01); *A61F 2/4455* (2013.01); *A61F 2/4611* (2013.01); *A61F 2/4603* (2013.01); *A61F 2002/3093* (2013.01); *A61F 2002/30266* (2013.01); *A61F 2002/30471* (2013.01); *A61F 2002/30476* (2013.01); *A61F 2002/30492* (2013.01); *A61F 2002/30538* (2013.01); *A61F 2002/30556* (2013.01);
(Continued)

(58) Field of Classification Search
CPC ...... A61F 2/447; A61F 2/4455; A61F 2/4611; A61F 2/4603; A61F 2002/4475
See application file for complete search history.

(56) References Cited

U.S. PATENT DOCUMENTS

| 5,860,973 A | 1/1999 | Michelson |
| 6,562,074 B2 | 5/2003 | Gerbec et al. |

(Continued)

FOREIGN PATENT DOCUMENTS

| WO | WO 2013/036707 | 3/2013 |
| WO | WO 2016/019230 | 2/2016 |

OTHER PUBLICATIONS

The supplemental European search report and European search opinion of a corresponding foreign filed application.

*Primary Examiner* — Amy R Sipp
(74) *Attorney, Agent, or Firm* — Ross M. Carothers

(57) ABSTRACT

Intervertebral devices and systems, and methods of their use, are disclosed having configurations suitable for placement between two adjacent vertebrae, replacing the functionality of the disc therebetween. Intervertebral devices and systems contemplated herein are implantable devices intended for replacement of a vertebral disc, which may have deteriorated due to disease for example. The intervertebral devices and systems are configured to allow for ample placement of therapeutic agents therein, including bone growth enhancement material, which may lead to better fusion between adjacent vertebral bones. The intervertebral devices and systems are configured for use in minimally invasive procedures, if desired.

12 Claims, 51 Drawing Sheets

(52) U.S. Cl.
CPC ............... *A61F 2002/30579* (2013.01); *A61F 2002/30593* (2013.01); *A61F 2002/30772* (2013.01); *A61F 2002/30785* (2013.01); *A61F 2002/30892* (2013.01); *A61F 2002/30904* (2013.01); *A61F 2002/30906* (2013.01); *A61F 2002/4627* (2013.01); *A61F 2002/4628* (2013.01)

(56) References Cited

U.S. PATENT DOCUMENTS

| | | | |
|---|---|---|---|
| 6,648,917 B2 | 11/2003 | Gerbec et al. | |
| 6,852,129 B2 | 2/2005 | Gerbec et al. | |
| 6,863,673 B2 | 3/2005 | Gerbec et al. | |
| 6,986,772 B2 | 1/2006 | Michelson | |
| 7,118,579 B2 | 10/2006 | Michelson | |
| 7,204,853 B2 | 4/2007 | Gordon et al. | |
| 7,235,082 B2 | 6/2007 | Bartish et al. | |
| 7,316,714 B2 | 1/2008 | Gordon et al. | |
| 7,655,027 B2 | 2/2010 | Michelson | |
| 7,753,958 B2 | 7/2010 | Gordon et al. | |
| 7,828,849 B2 | 11/2010 | Lim | |
| 7,850,733 B2 | 12/2010 | Baynham | |
| 7,909,869 B2 | 3/2011 | Gordon | |
| 7,922,729 B2 | 4/2011 | Michelson | |
| 7,967,867 B2 | 6/2011 | Barreiro et al. | |
| 8,062,375 B2 | 11/2011 | Glerum et al. | |
| 8,118,870 B2 | 2/2012 | Gordon et al. | |
| 8,118,871 B2 | 2/2012 | Gorden et al. | |
| 8,123,810 B2 | 2/2012 | Gorden et al. | |
| 8,147,550 B2 | 4/2012 | Gorden et al. | |
| 8,172,903 B2 | 5/2012 | Gordon et al. | |
| 8,257,440 B2 | 9/2012 | Gordon et al. | |
| 8,308,805 B2 | 11/2012 | Lynn et al. | |
| 8,328,818 B1 | 12/2012 | Seifert et al. | |
| 8,343,224 B2 | 1/2013 | Lynn et al. | |
| 8,382,842 B2 | 2/2013 | Greenhalgh et al. | |
| 8,398,713 B2 | 3/2013 | Weiman | |
| 8,435,298 B2 | 5/2013 | Weiman | |
| 8,444,692 B2 | 5/2013 | Michelson | |
| 8,491,659 B2 | 7/2013 | Weiman | |
| 8,496,664 B2 | 7/2013 | Michelson | |
| 8,518,120 B2 | 8/2013 | Glerum et al. | |
| 8,556,979 B2 | 10/2013 | Glerum et al. | |
| 8,603,168 B2 | 12/2013 | Gordon et al. | |
| 8,632,595 B2 | 1/2014 | Weiman | |
| 8,647,386 B2 | 2/2014 | Gordon et al. | |
| 8,679,183 B2 | 3/2014 | Glerum et al. | |
| 8,685,098 B2 | 4/2014 | Glerum et al. | |
| 8,709,086 B2 | 4/2014 | Glerum | |
| 8,753,398 B2 | 6/2014 | Gordon et al. | |
| 8,771,321 B2 | 7/2014 | Michelson | |
| 2004/0153065 A1 | 8/2004 | Lim | |
| 2005/0131536 A1* | 6/2005 | Eisermann | A61F 2/447 623/17.11 |
| 2010/0049324 A1 | 2/2010 | Valdevit et al. | |
| 2010/0204795 A1 | 8/2010 | Greenhalgh | |
| 2010/0211176 A1* | 8/2010 | Greenhalgh | A61F 2/447 623/17.15 |
| 2011/0093074 A1 | 4/2011 | Glerum et al. | |
| 2011/0282453 A1 | 11/2011 | Greenhalgh et al. | |
| 2012/0150304 A1 | 6/2012 | Glerum | |
| 2012/0150305 A1 | 6/2012 | Glerum | |
| 2012/0158146 A1 | 6/2012 | Glerum | |
| 2012/0158147 A1 | 6/2012 | Glerum et al. | |
| 2012/0158148 A1 | 6/2012 | Glerum | |
| 2013/0158663 A1* | 6/2013 | Miller | A61F 2/4455 623/17.16 |
| 2014/0039622 A1 | 2/2014 | Glerum et al. | |
| 2014/0052254 A1 | 2/2014 | Glerum et al. | |
| 2014/0058516 A1 | 2/2014 | Glerum et al. | |
| 2014/0058519 A1 | 2/2014 | Glerum et al. | |
| 2014/0094916 A1 | 4/2014 | Glerum et al. | |
| 2014/0121774 A1 | 5/2014 | Glerum et al. | |
| 2014/0128977 A1 | 5/2014 | Glerum et al. | |
| 2015/0342749 A1* | 12/2015 | Baynham | A61F 2/4455 623/17.16 |

\* cited by examiner

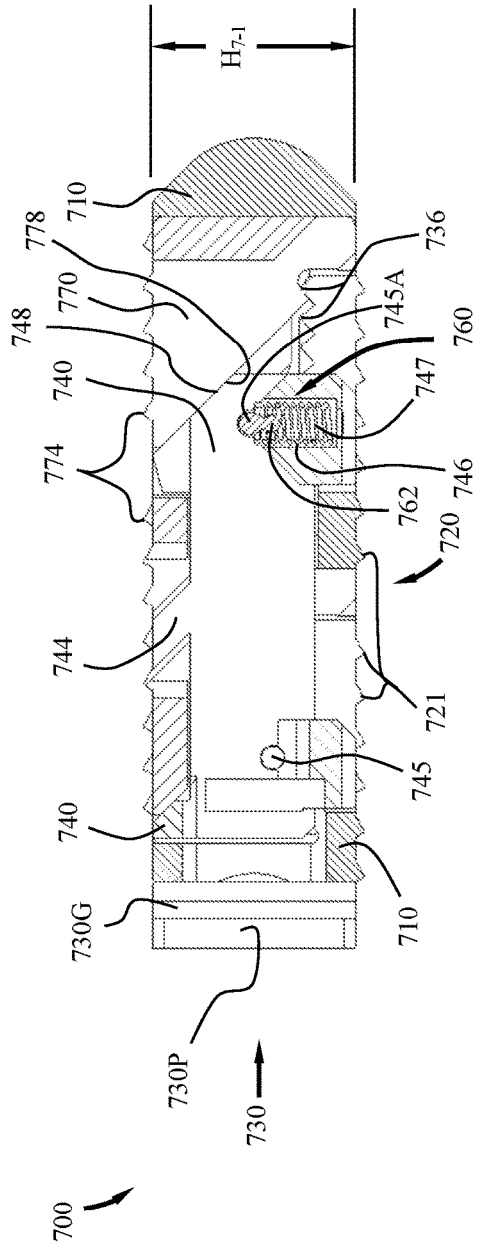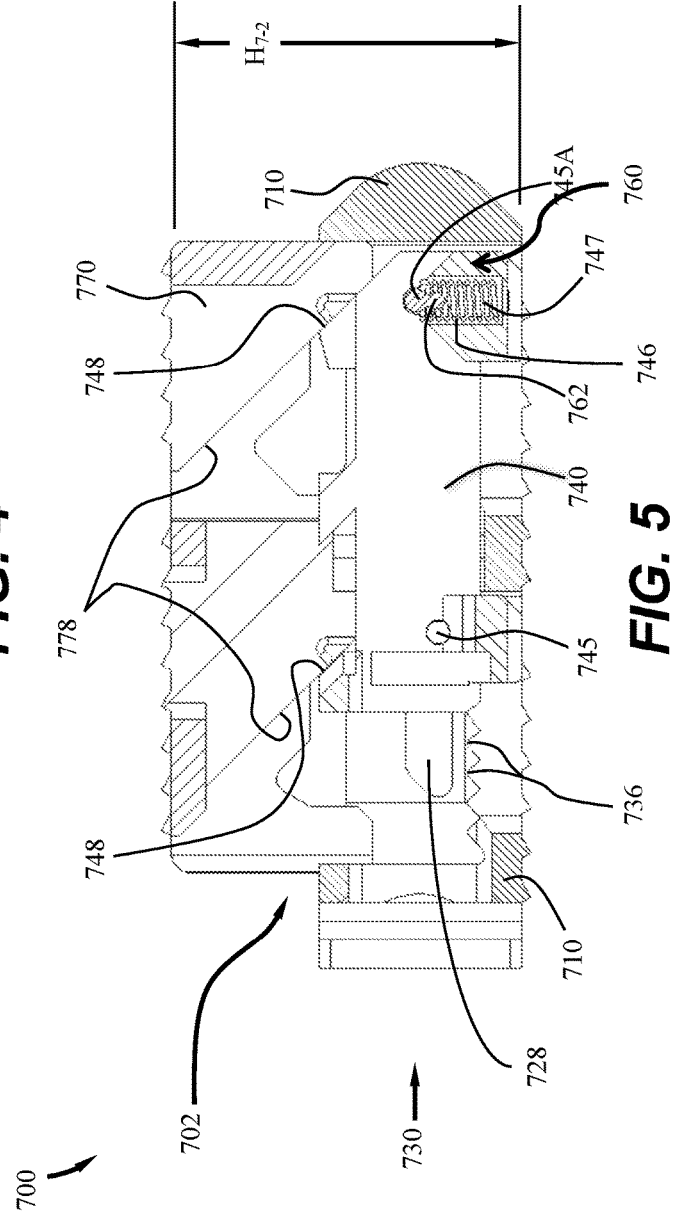

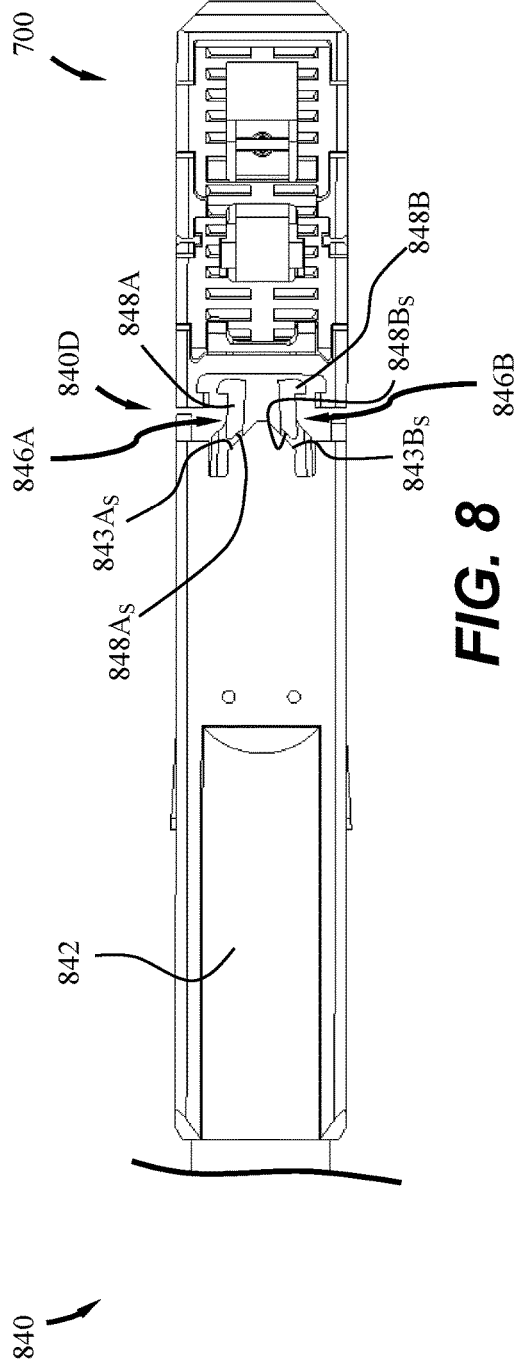
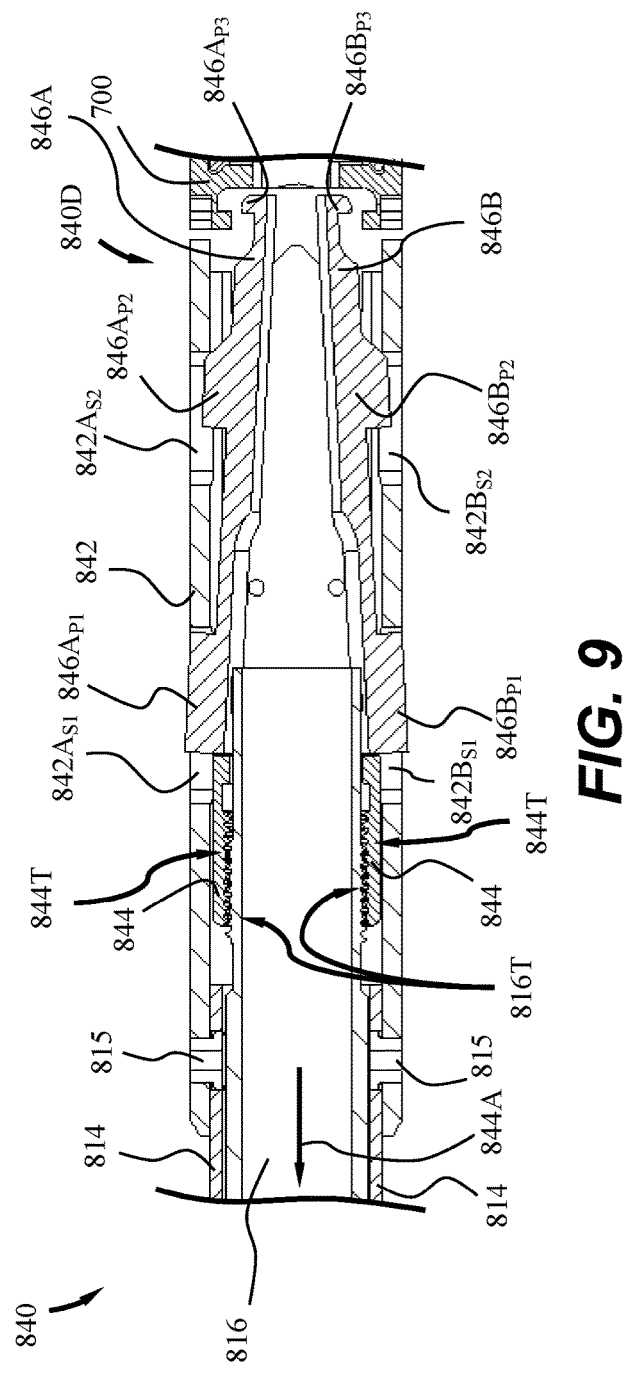

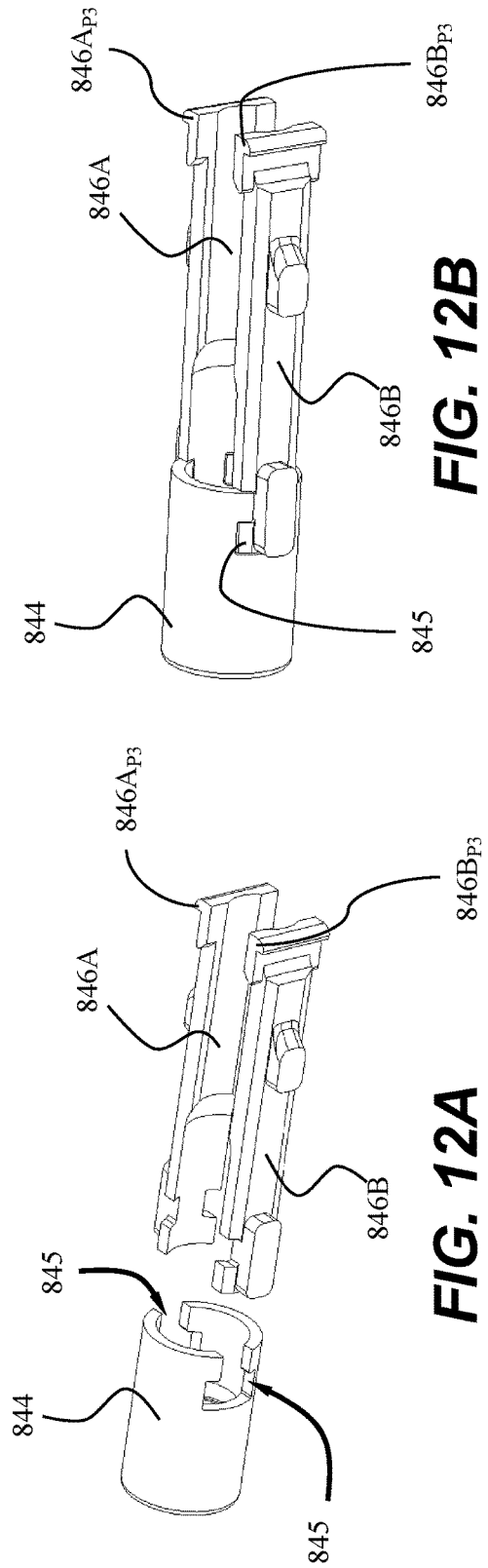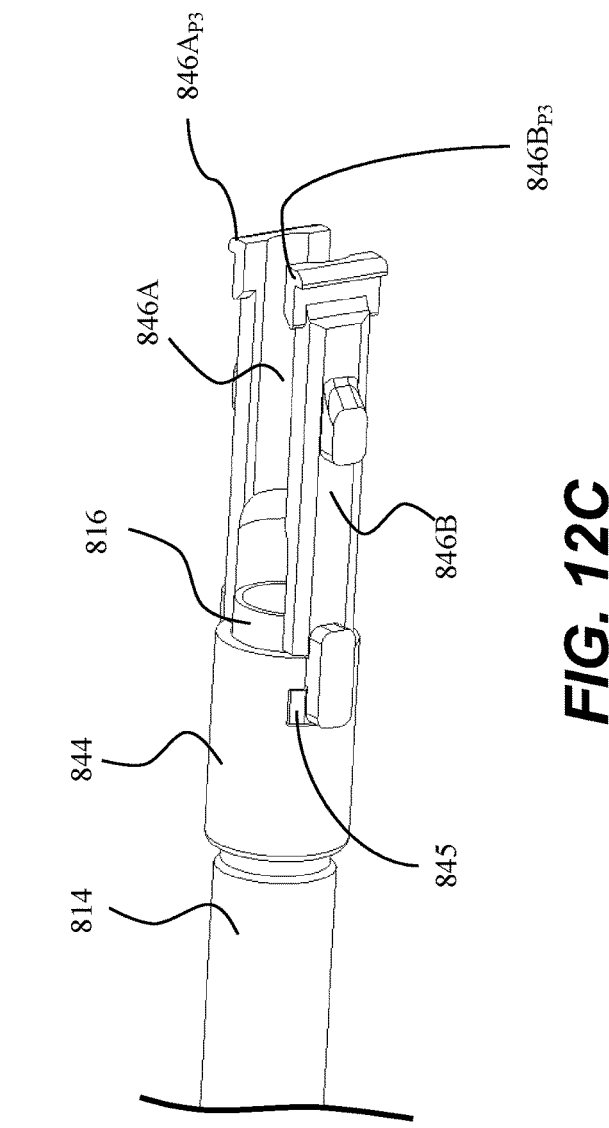
FIG. 12A
FIG. 12B
FIG. 12C

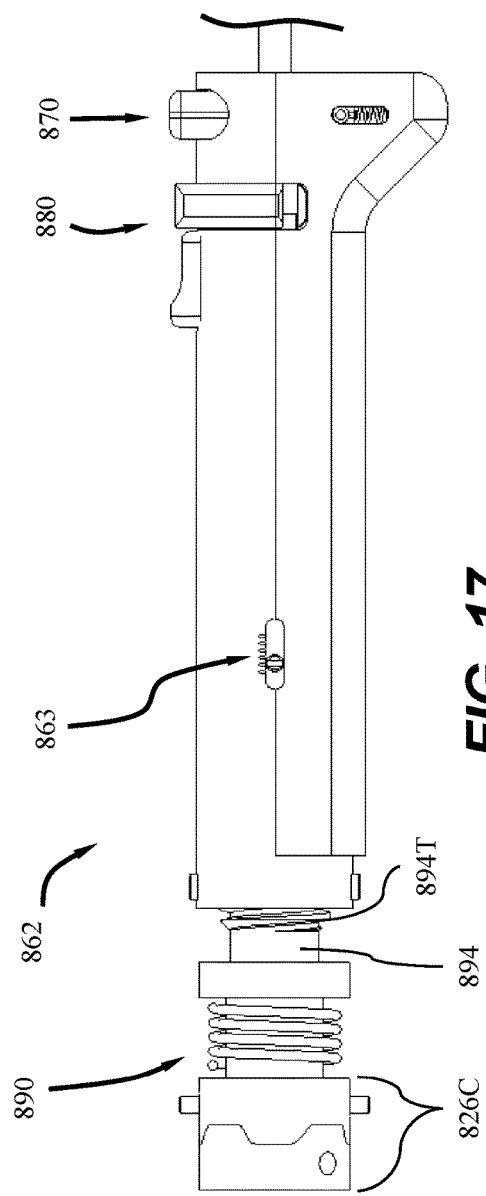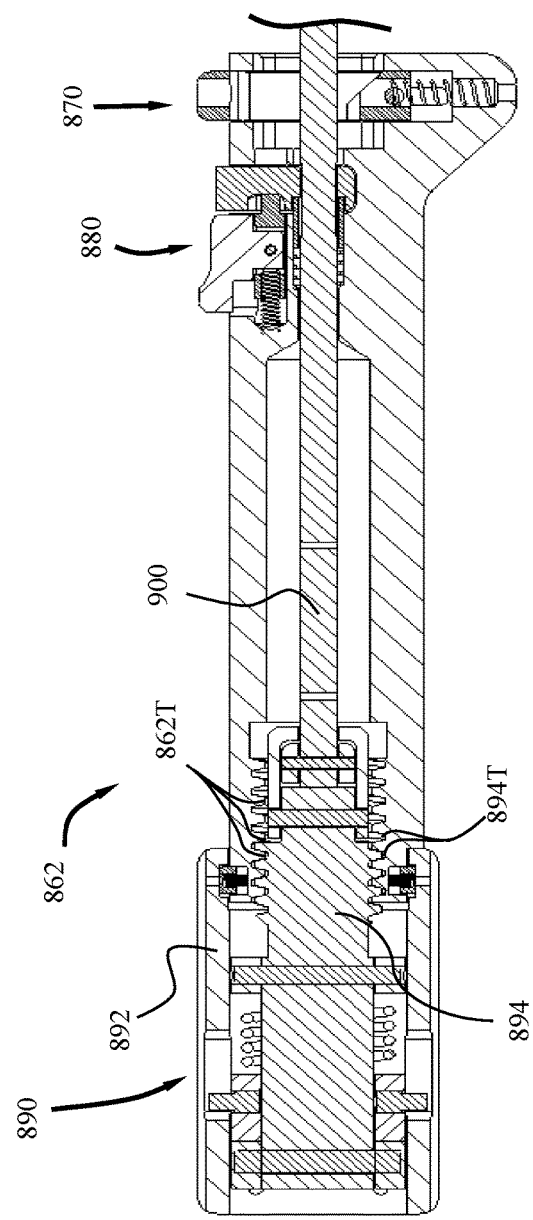

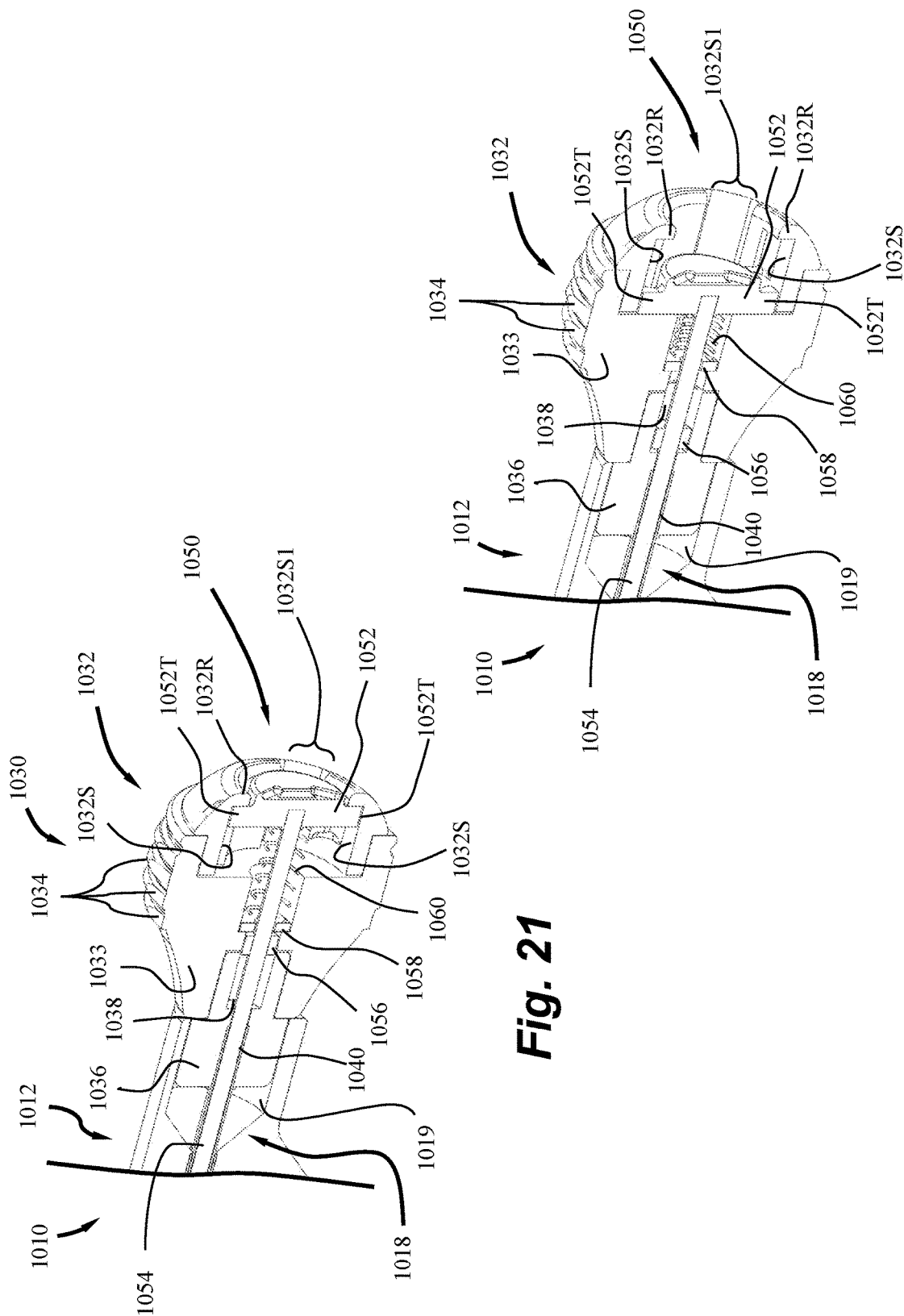

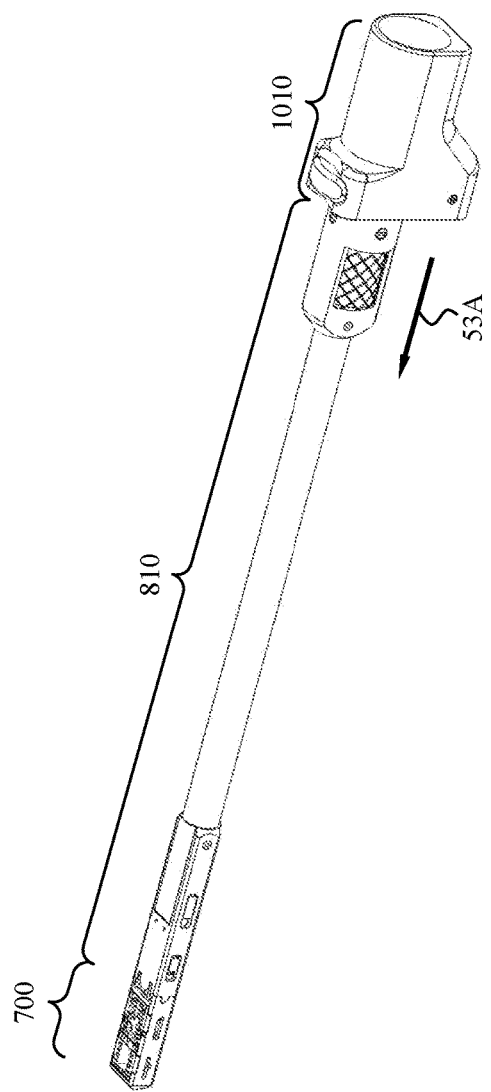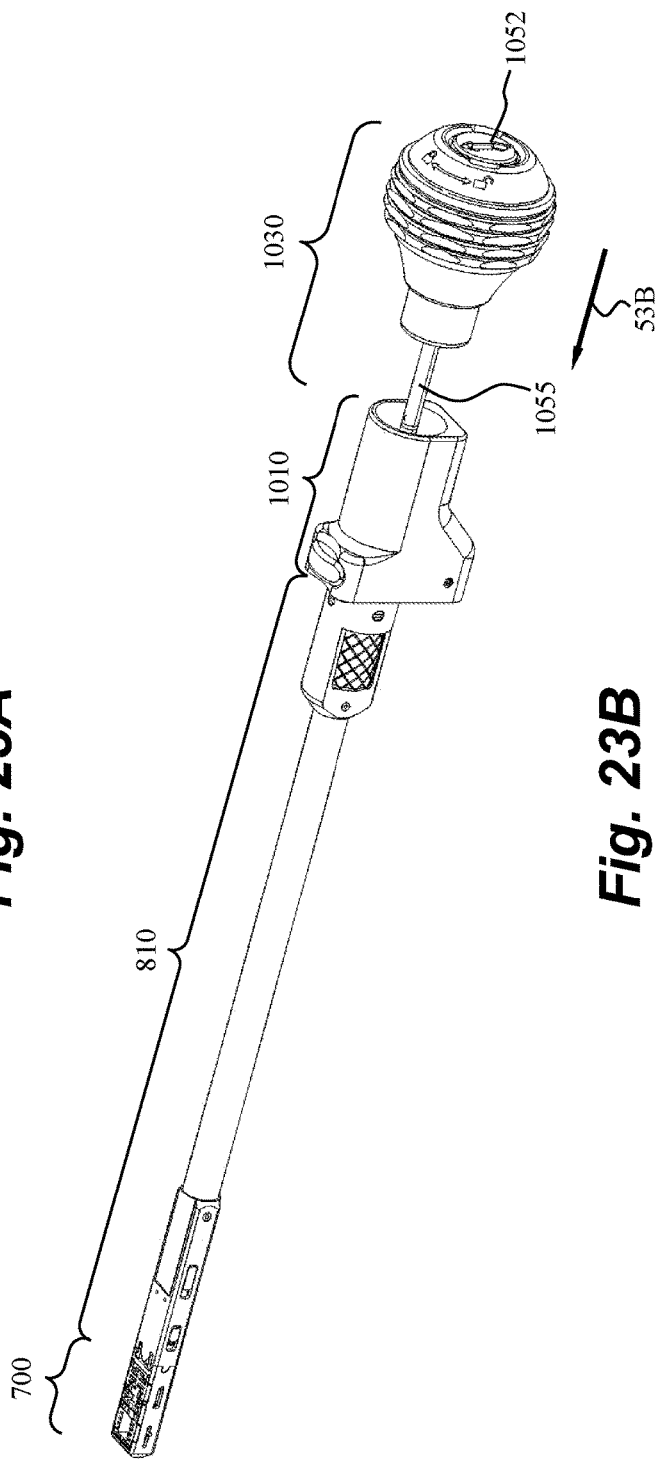

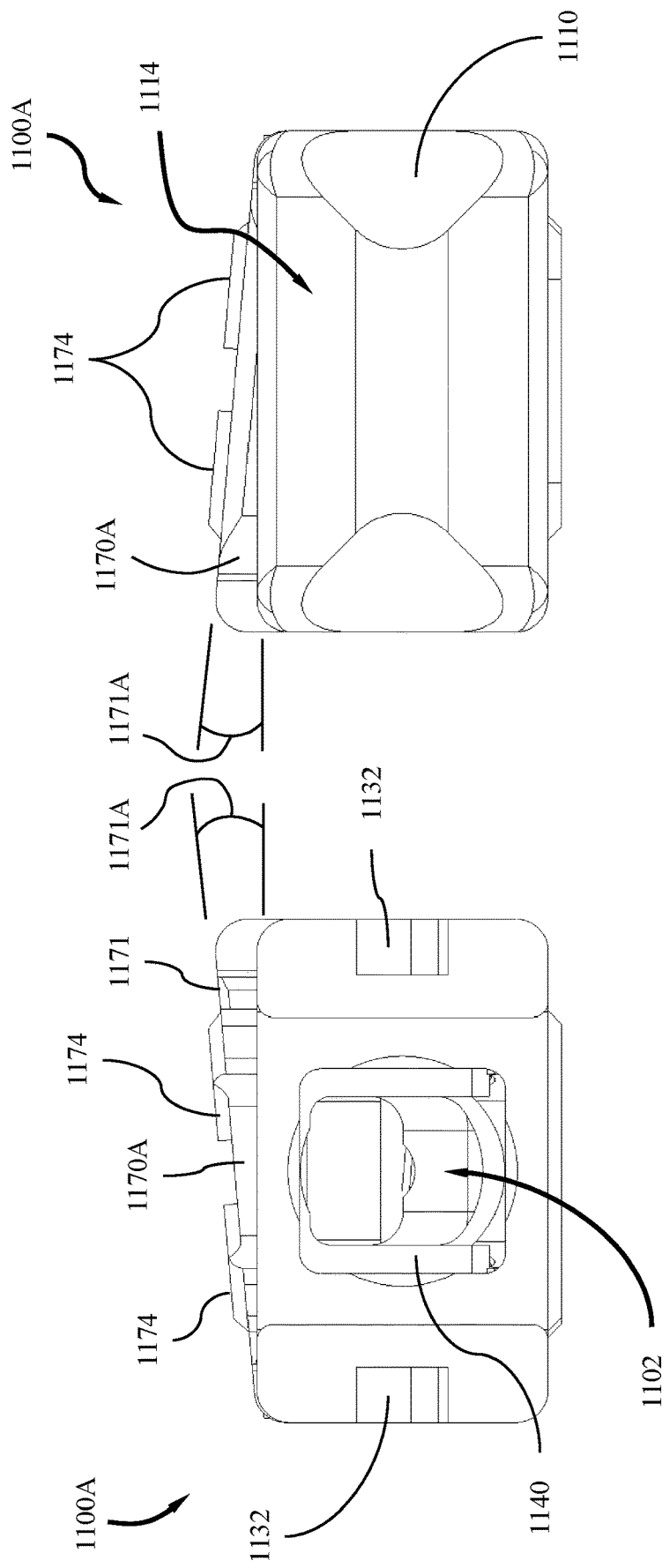

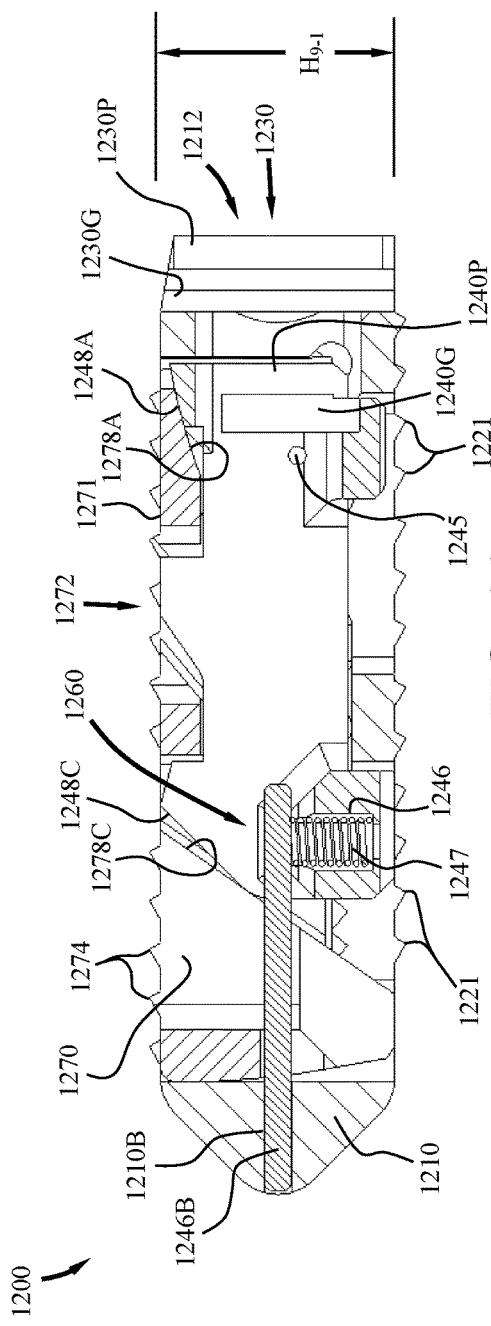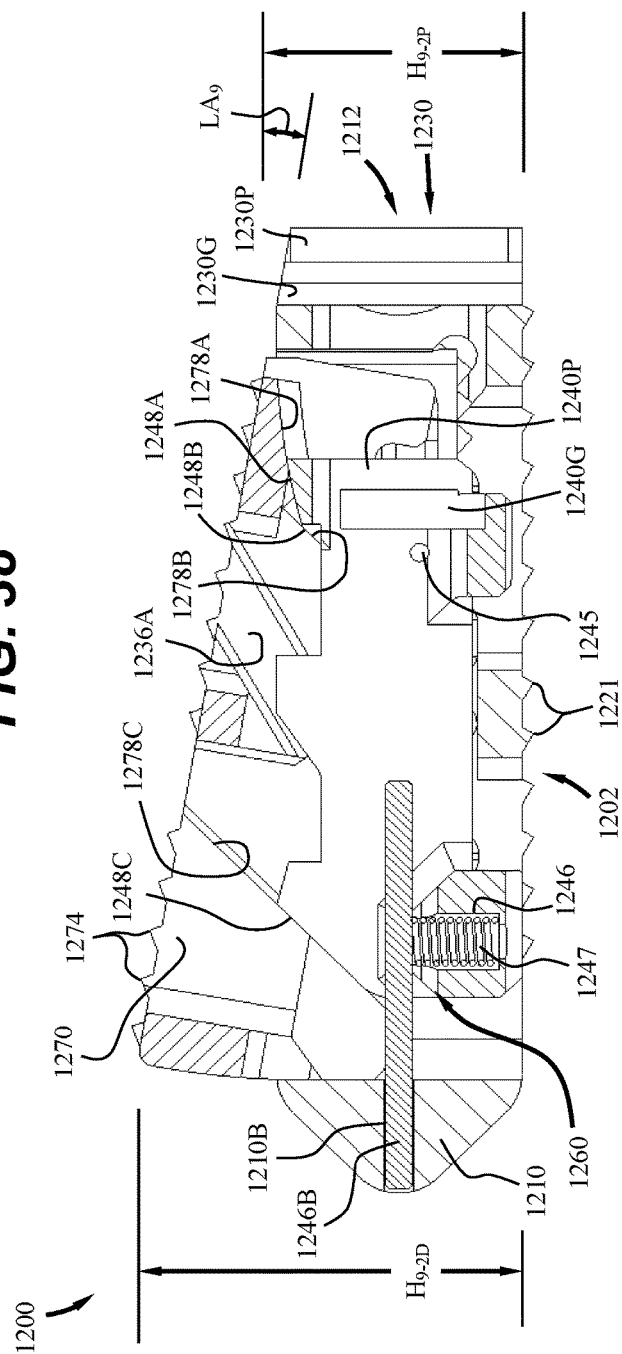

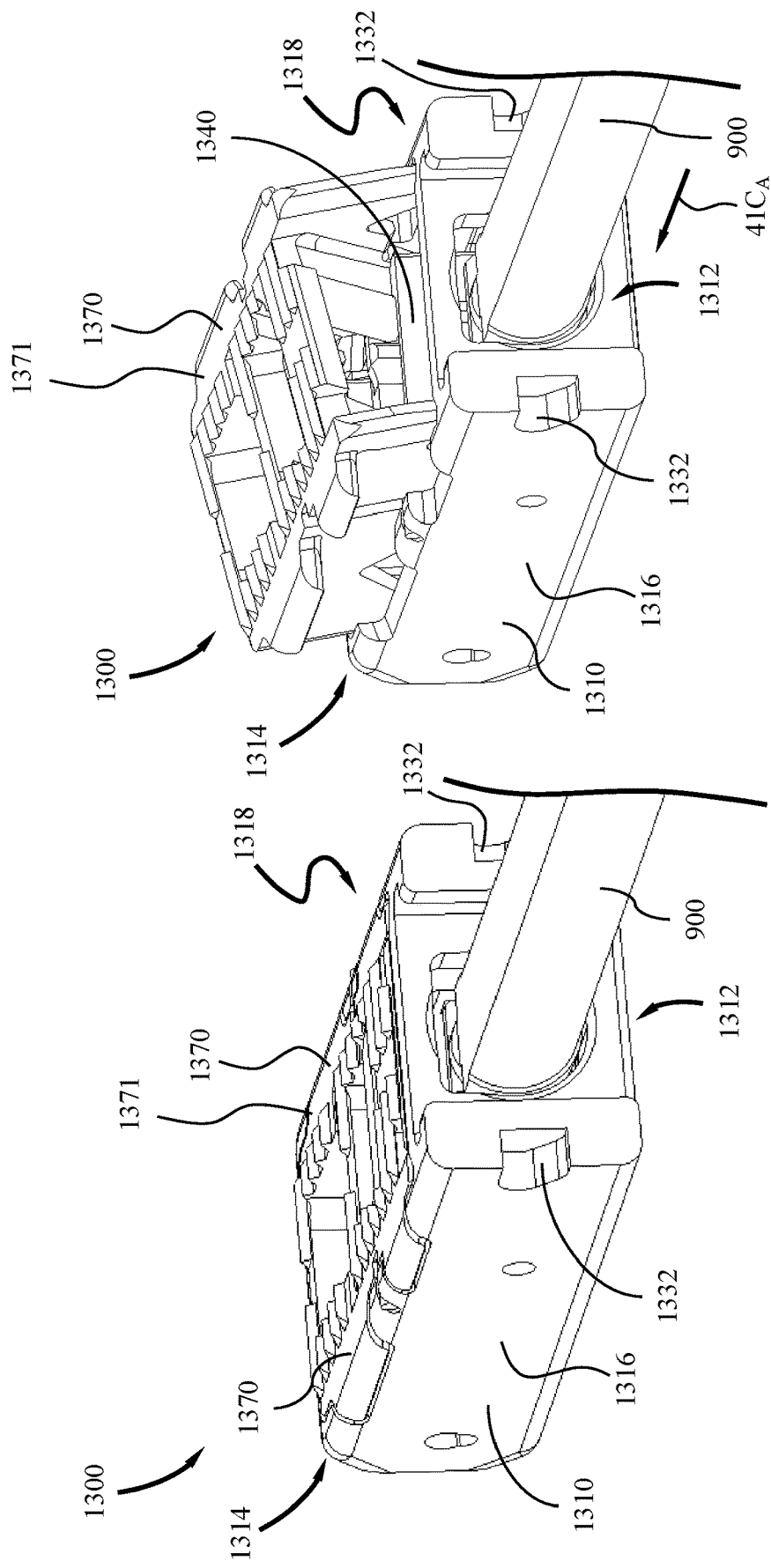

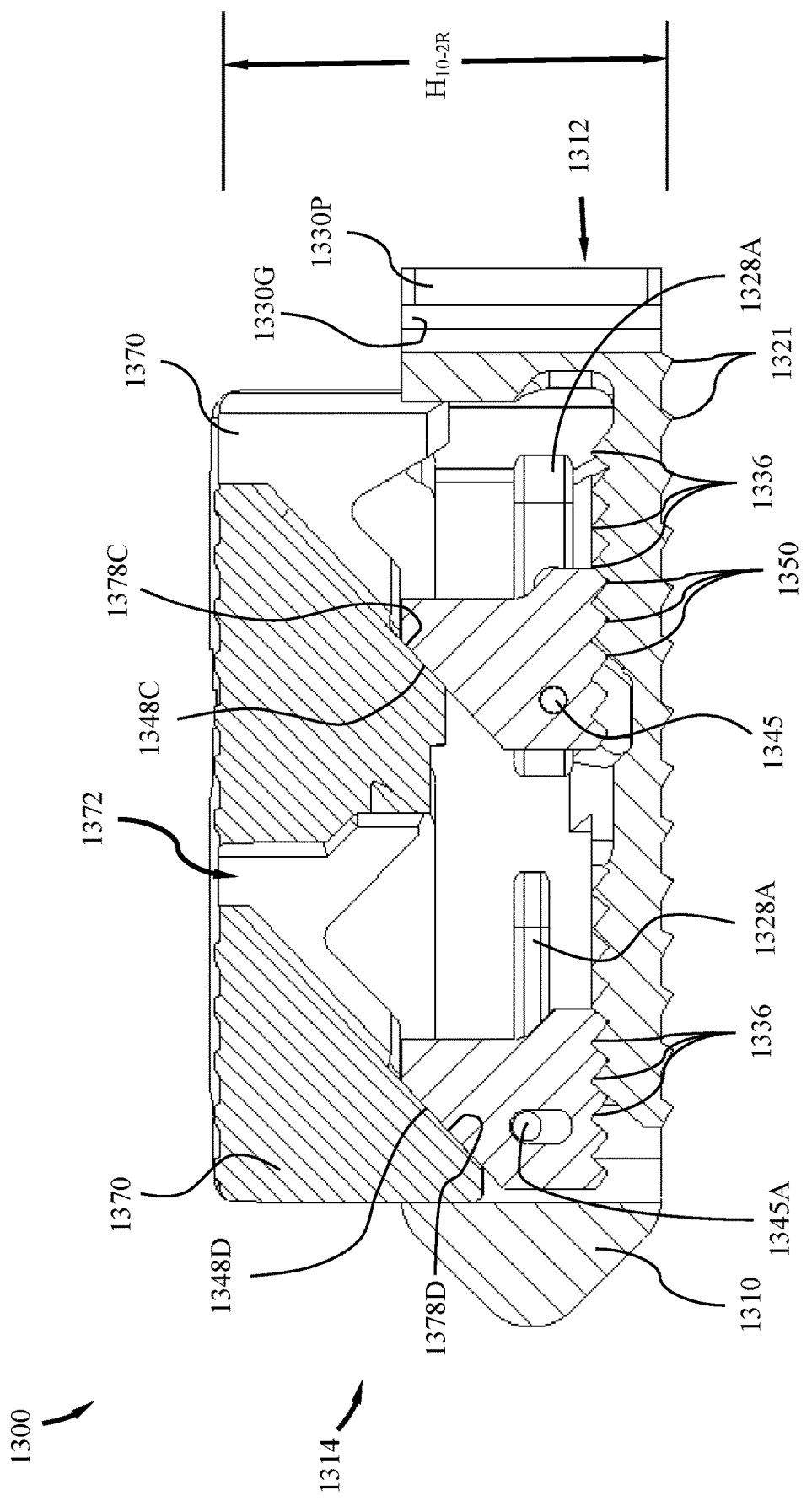

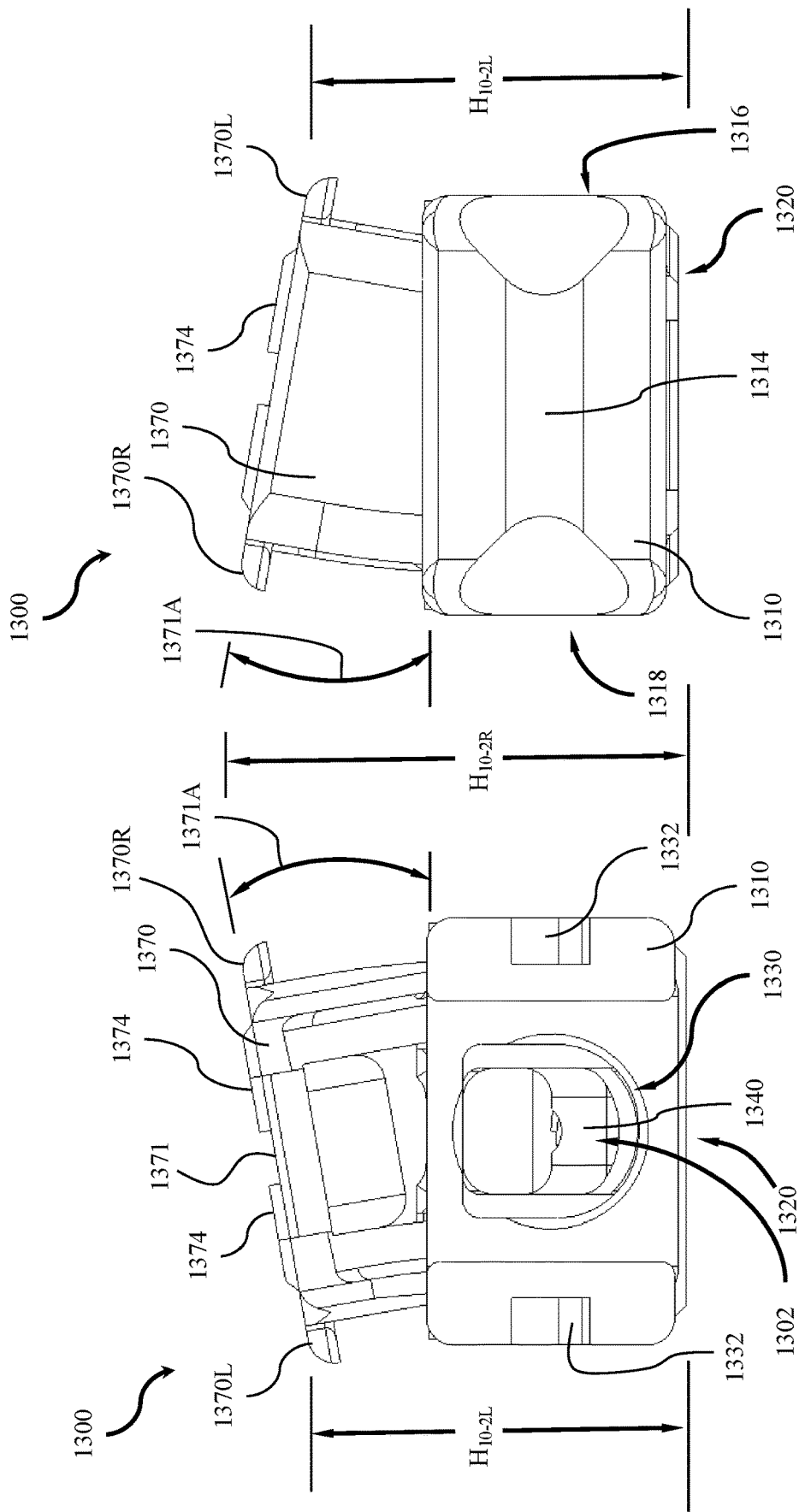

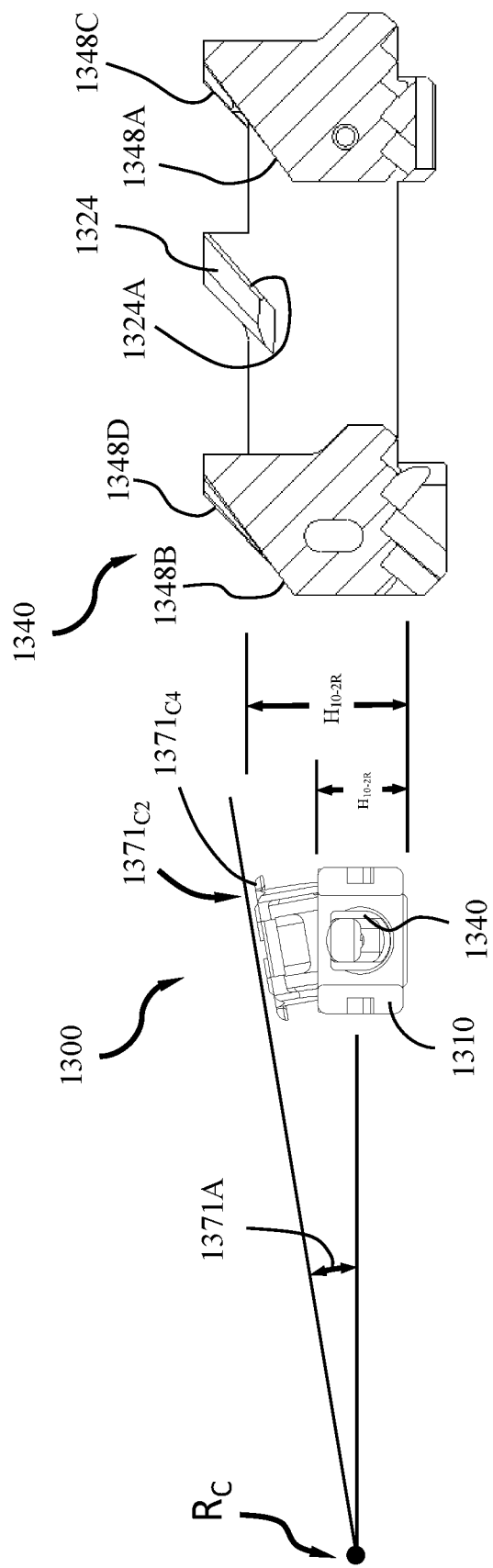

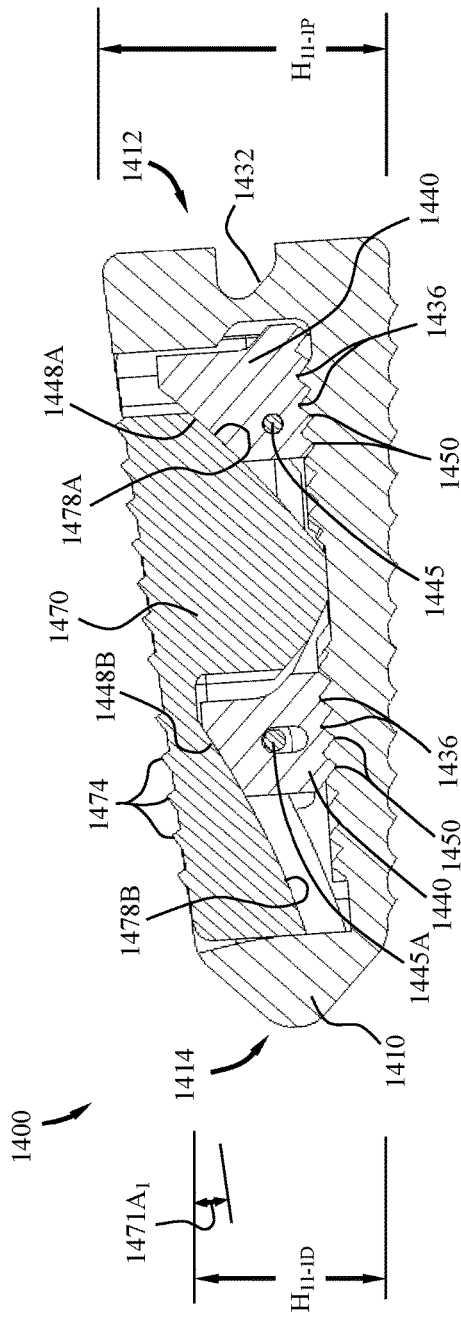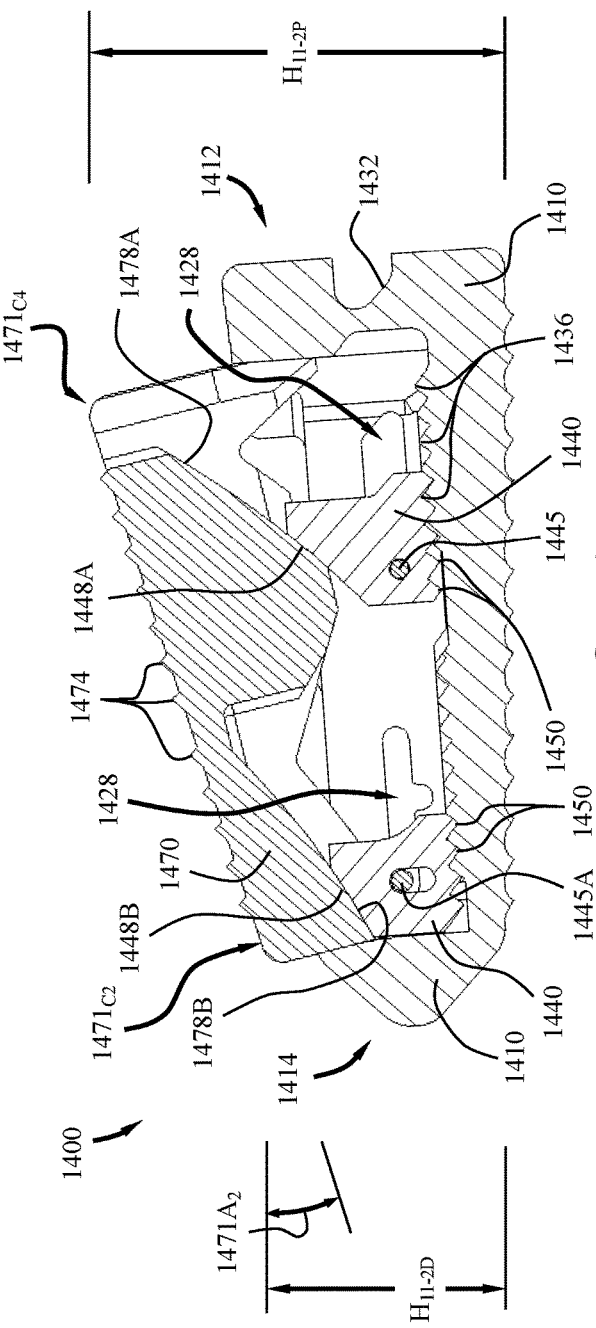

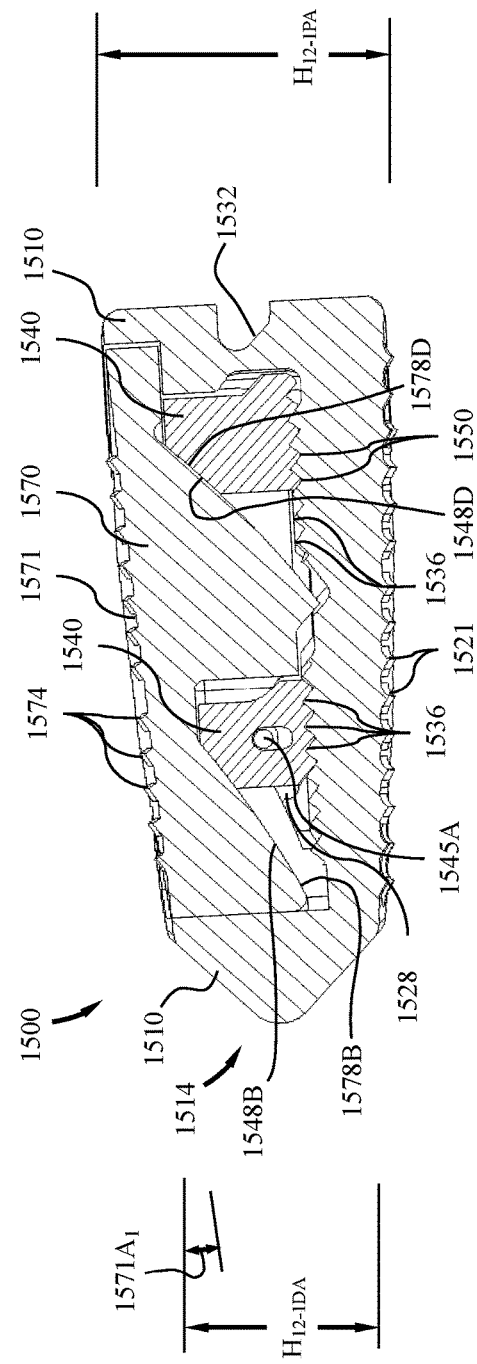
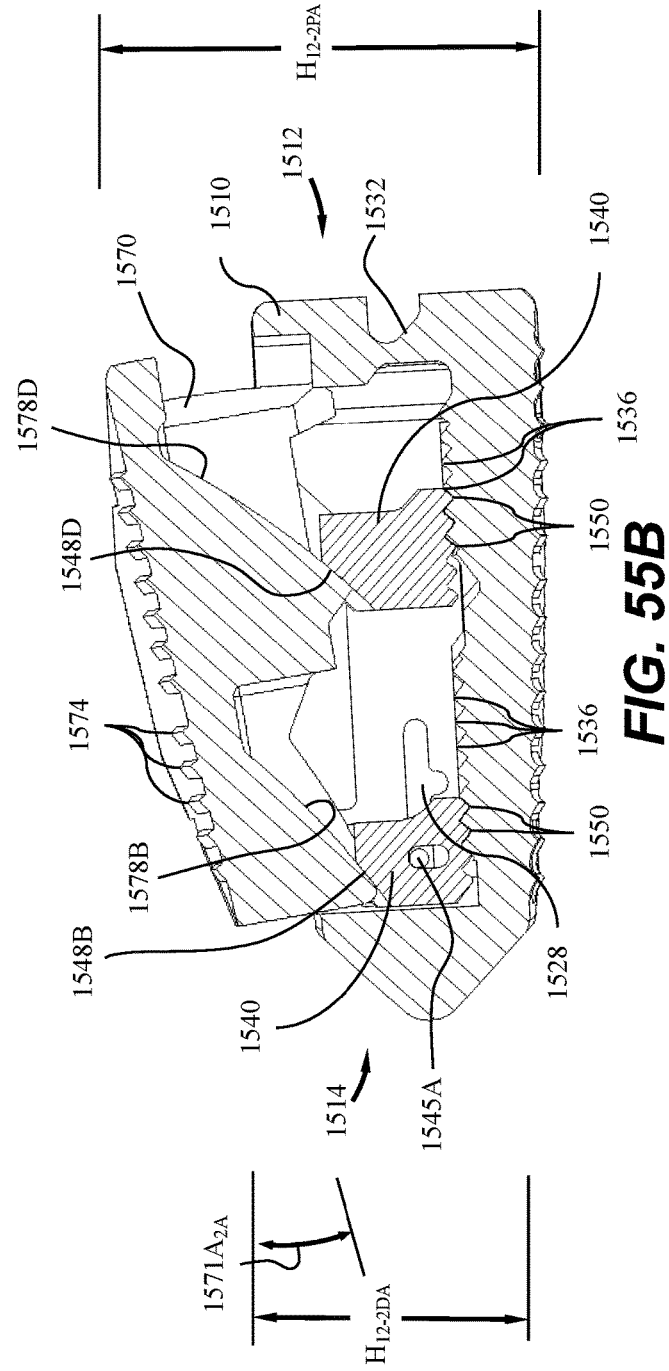
FIG. 55A
FIG. 55B

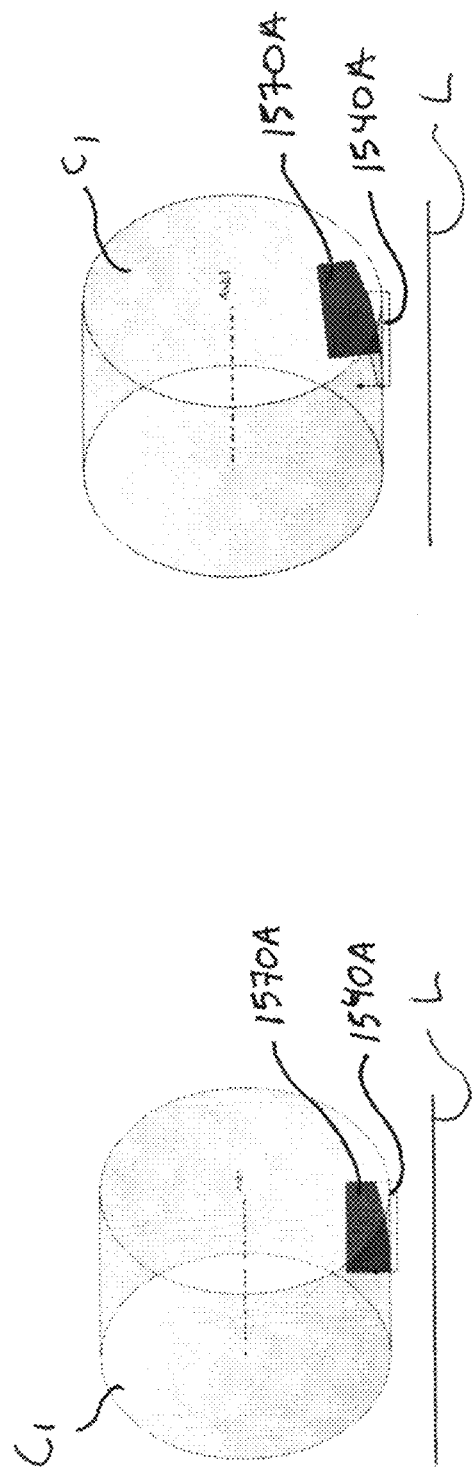
FIG. 58A
FIG. 58B
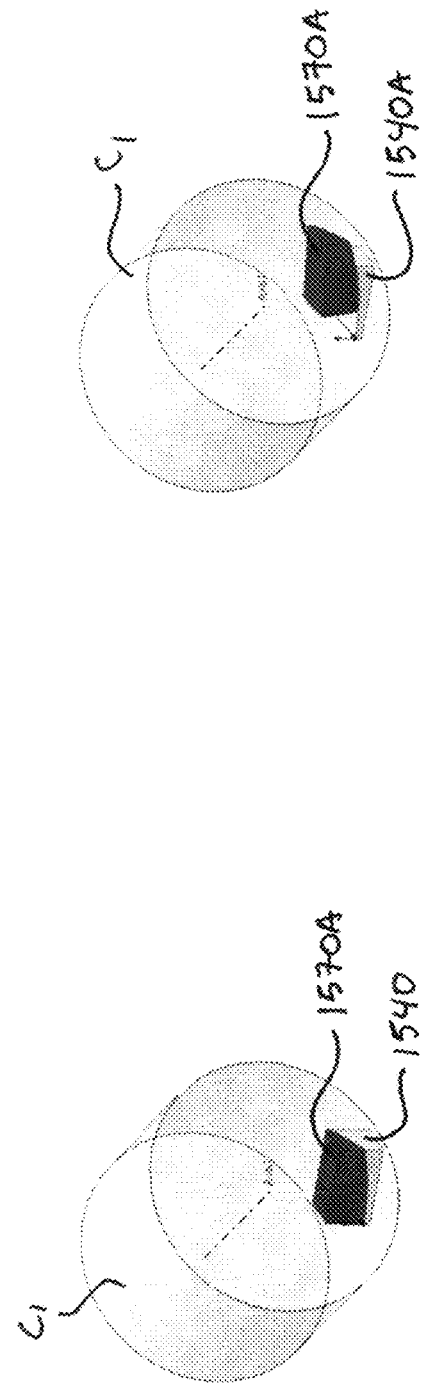
FIG. 59A
FIG. 59B

INTERVERTEBRAL DEVICES AND RELATED METHODS

This application claims benefit of priority to provisional application, Ser. No. 62/194,149, filed Jul. 17, 2015 and entitled, "Intervertebral Devices and Related Methods," and is incorporated herein by reference in its entirety.

BACKGROUND

Field of this Disclosure

This disclosure relates generally to medical devices, and more particularly, to medical devices utilized for procedures performed on or near the spine.

Description of the Related Art

Degenerative disc diseases are common disorders that can impact all or a portion of a vertebral disc, a cushion-like structure located between the vertebral bodies of the spine. Degenerative disc diseases may lead, for example, to a disc herniation where the vertebral disc bulges out or extrudes beyond the usual margins of the disc and the spine. Disc herniation, in particular, is believed to be the result of excessive loading on the disc in combination with weakening of the annulus due to such factors as aging and genetics. Such degenerative disc diseases are also associated with spinal stenosis, a narrowing of the bony and ligamentous structures of the spine. Although disc herniation can occur anywhere along the perimeter of the disc, it occurs more frequently in the posterior and posterior-lateral regions of the disc, where the spinal cord and spinal nerve roots reside. Compression of these neural structures can lead to pain, parasthesias, weakness, urine and fecal incontinence and other neurological symptoms that can substantially impact basic daily activities and quality of life.

Temporary relief of the pain associated with disc herniation, or other degenerative disc diseases, is often sought through conservative therapy, which includes positional therapy (e.g. sitting or bending forward to reduce pressure on the spine), physical therapy, and drug therapy to reduce pain and inflammation. When conservative therapy fails to resolve a patient's symptoms, surgery may be considered to treat the structural source of the symptoms. When surgery fails to resolve a patient's symptoms, more drastic measures may include disc replacement surgery or vertebral fusion.

There are numerous implantable devices that have been developed for disc replacement and vertebral fusion. Such implantable devices, also referred to as cage systems, may be deployed to replace the vertebral disc and fuse the adjacent vertebrae, relieving pain and providing increased mobility to the patient. However, known implantable devices and methodologies have drawbacks. For example, many of the implantable devices currently available do not allow for an ample amount of materials, such as certain therapeutic agents that encourage bone growth, to be positioned within and around the devices and adjacent vertebral bones. Such bone growth materials allow for a higher level of fusion of the adjacent vertebrae, providing increased stabilization and minimize the likelihood of further issues in the future. Further, many implantable intervertebral devices require complex manipulation of delivery systems for implanting the device itself, and other systems for deployment of such therapeutic agents. Many of the implantable intervertebral devices available provide a single lifting activity or function. For example, they may be fixed in a certain geometric configuration, having a fixed height, or a fixed angular relationship between a top surface and a bottom surface of an intervertebral device, which limits the procedure available for positioning the device within a patient. Also, many implantable devices are large structures that are not easily utilized in a minimally invasive procedure. Rather, they may require surgical procedures allowing greater access, which subjects the patient to higher risks of disease and prolonged infection.

There is a need for implantable devices intended for replacement of a vertebral disc, which allow for ample placement of bone growth material that may lead to better fusion between adjacent vertebral bones. There is a further need for implantable intervertebral devices that include delivery systems that provide increased functionality, such delivery systems utilized for deployment of the intervertebral device within a patient as well as therapeutic agents to encourage bone growth and healing. There is also a need for an intervertebral device that is configured to include a top planar surface that is further adapted to include portions that move at one of a plurality of rates as the intervertebral device is expanded, such that the top planar surface forms a desired complex angle with respect to the bottom planar surface as the intervertebral device is expanded. Accordingly, the intervertebral device may be adapted to correspond to any suitable approach to the spine, including but not limited to, anterior lumbar interbody fusion (ALIF) access where the vertebral disc is accessed from an anterior abdominal incision; posterior lumbar interbody fusion (PLIF) access where the vertebral disc is accessed from a posterior incision; transforaminal lumbar interbody fusion (TLIF) access where the disc is accessed from a posterior incision on one side of the spine; transpsoas interbody fusion (DLIF or XLIF) access where the disc is accessed from an incision through the psoas muscle on one side of the spine; oblique (posterior) lumbar interbody fusion (OLLIF) access where the disc is accessed from an incision through the psoas muscle obliquely; or any other desired access. There is still a further need for such implantable devices to be provided during minimally invasive procedures, reducing the risk of infection and allowing for quicker healing of the patient.

BRIEF SUMMARY

Consistent with the present disclosure, an expandable intervertebral device may comprise a base element, a first body portion slidably attached to the base and configured to move in at least a first direction with respect to the base, the first body portion including a first plurality of curvilinear surfaces, a second body portion slidably attached to the base and configured to move in at least a second direction with respect to the base, the second body portion including a second plurality of curvilinear surfaces, each of the first plurality of curvilinear surfaces configured to couple with a respective one of the second plurality of curvilinear surfaces, such that the second body portion at least rotates with respect to the base as the first body portion moves in the first direction. In certain embodiments the first body portion may include a first engaging element and the second body portion may include a second engaging element, the second engaging element configured to couple to the first engaging element. In other embodiments the first and second engaging elements are configured such that the coupling of the first and second engaging elements prevents movement of the second body portion in a third direction with respect to the base when a compression force is applied between the top surface of the second body portion and the bottom surface of the base. In yet other embodiments the third direction may be substantially opposite to the second direction.

In certain embodiments the device may include a longitudinal access and the second body portion may include an axis of rotation, the axis of rotation of the second body portion being parallel to the longitudinal axis of the device. While in other embodiments the device may include a longitudinal access and the second body portion may include an axis of rotation, the axis of rotation of the second body portion being perpendicular to the longitudinal axis of the device. In still other embodiments the device may include a longitudinal access and the second body portion may include an axis of rotation, the axis of rotation of the second body portion neither being perpendicular nor parallel to the longitudinal axis of the device.

In still other embodiments each of a first pair of the first curvilinear surfaces of the first body portion are similar, while in other embodiments each of a second pair of the first curvilinear surfaces of the first body portion are similar, the second pair being different from the first pair, and in yet other embodiments each of the first plurality of curvilinear surfaces are different.

In other embodiments the device includes a delivery system, which may have an attachment assembly including a lumen therethrough, the attachment assembly may be configured to removably attach to the base element and position the device. In still other embodiments the delivery system may further include an expansion tool having an elongate shaft, a distal end of the elongate shaft may be configured to pass through the lumen of the attachment assembly and removably attach to the first body portion, the expansion tool being configured to translate the elongate shaft and the first body portion attached thereto. In yet other embodiments the delivery system may further include an insertion assembly having an elongate member, the elongate member of the insertion assembly may be slidably coupled to the lumen of the attachment tool, a distal end of the elongate member configured to translate through the lumen of the attachment tool.

In certain other embodiments the base, first body portion, and second body portion may be configured to define a void central to the base, first body portion and second body portion, the distal end of the elongate member configured to translate within the void. In certain embodiments a central longitudinal axis of the base, first body portion, and second body portion passes through the void.

In other embodiments the second body portion includes a top surface having a first corner portion, a second corner portion, a third corner portion and a fourth corner portion, each of the first corner portion, second corner portion, third corner portion, and fourth corner portion moving at a corresponding one of a plurality of rates as the second body portion moves in the second direction, the plurality of rates being selected such that the top surface forms an angle with respect to the bottom surface as the second body portion moves in the second direction. In yet other embodiments the rate of one of the first corner portion and the second corner portion is the same as the rate of one of the third corner portion and the fourth corner portion, while in other embodiments each of the plurality of rates are different, such that the top surface of the second body portion forms a complex angle with respect to the bottom surface of the base.

In another aspect, a method includes providing an intervertebral device having a height and a delivery system, the delivery system including an attachment assembly having a lumen, an expansion tool having a shaft, and an insertion tool having an elongate member, attaching the intervertebral device to a distal end of the attachment assembly and positioning the intervertebral device between adjacent vertebrae, inserting the expansion tool within the lumen of the attachment assembly, a distal end of the expansion tool removably attaching to the intervertebral device, and translating the expanding tool resulting in a change in the height of the intervertebral device. In other embodiments the method may further include detaching the expansion tool from the intervertebral device and removing the expansion tool from the lumen of the delivery system, positioning a therapeutic agent within the lumen of the attachment assembly, translating the elongate member of the insertion tool within the lumen of the attachment assembly, translation of the elongate member resulting in translation of the therapeutic agent, such that a portion of the therapeutic agent is positioned within the intervertebral device. In yet other embodiments the insertion tool further may include a guide assembly having a tubular member, the step of positioning the therapeutic agent may include positioning the therapeutic agent within the lumen of the tubular member of the guide assembly, and the step of translating the elongate member of the insertion tool may include the step of translating the tubular member of the guide assembly within the lumen of the attachment assembly.

BRIEF DESCRIPTION OF THE DRAWINGS

Reference will be made to embodiments of the disclosure, examples of which may be illustrated in the accompanying figures. These figures are intended to be illustrative, not limiting. Although certain aspects of the embodiments are generally described in the context of these embodiments, it should be understood that it is not intended to limit the scope to these particular embodiments. In the drawings:

FIG. 4 is a side partial section view of the exemplary intervertebral device of FIG. 1.

FIG. 5 is another side partial section view of the exemplary intervertebral device of FIG. 1.

FIG. 8 is a top view of an element of the portion of the exemplary intervertebral device of FIG. 7.

FIG. 9 is a partial section view of the element depicted in FIG. 8.

FIGS. 12A-C are perspective views of certain elements of the portion of the exemplary delivery device of FIG. 7.

FIGS. 16A-46B are perspective views of a portion of the element FIG. 14, the portion engaging an element of an exemplary intervertebral device.

FIG. 17 is a partial cut view of a portion of the element of FIG. 14.

FIG. 18 is a partial section view of a portion of the element of FIG. 14.

FIG. 19 is a perspective view of a guide assembly, as part of a delivery tool.

FIG. 20 is a perspective view of an insertion assembly, as part of a delivery tool.

FIG. 21 is a partial section view of a portion of the insertion assembly of FIG. 20.

FIG. 22 is another partial section view of a portion of the insertion assembly of FIG. 20.

FIG. 23A is a perspective view of the guide assembly of FIG. 19, coupled to an exemplary attachment assembly.

FIG. 23B is a perspective view of the guide assembly of FIG. 19 and the insertion assembly of FIG. 20 coupled to an exemplary attachment assembly.

FIG. 26 is a top view of another exemplary intervertebral device.

FIG. 27 is a partial section view of the exemplary intervertebral device of FIG. 26.

FIG. 28 is another partial section view of the exemplary intervertebral device of FIG. 26.

FIG. 29 is a yet another partial section view of the exemplary intervertebral device of FIG. 26.

FIG. 30 is still another partial section view of the exemplary intervertebral device of FIG. 26.

FIGS. 31A and 31B are end views of another exemplary intervertebral device.

FIG. 34 is a top view of yet another exemplary intervertebral device.

FIG. 35 is a partial section view of the exemplary intervertebral device of FIG. 34.

FIG. 36 is another partial section view of the exemplary intervertebral device of FIG. 34.

FIG. 37 is yet another partial section view of the exemplary intervertebral device of FIG. 34.

FIG. 38 is a side elevation cut view of the intervertebral device of FIG. 34.

FIG. 39 is another side elevation cut view of the intervertebral device of FIG. 34.

FIG. 40 is still another side elevation cut view of the intervertebral device of FIG. 34.

FIGS. 41B and 41C are perspective views of the exemplary intervertebral device of FIG. 41A.

FIGS. 42 and 43 are side elevation cut views of the exemplary intervertebral device of FIG. 41A.

FIGS. 44 and 45 are additional side elevation cut views of the exemplary intervertebral device of FIG. 41A.

FIGS. 46A and 46B are end elevation views of the intervertebral device of FIG. 41A.

FIG. 47 is a graph depicting certain geometric properties of the exemplary intervertebral device of FIG. 41A.

FIG. 48 is a side elevation cut view of an element of the exemplary intervertebral device of FIG. 41A.

FIGS. 53A-53B are side section views of the exemplary intervertebral device of FIG. 51A.

FIGS. 55A and 55B are partial section views along a first longitudinal axis of the exemplary intervertebral device of FIG. 54A.

FIGS. 56A-60 are graphical views of portions of the intervertebral device of FIG. 54A.

DETAILED DESCRIPTION

Figure 1:
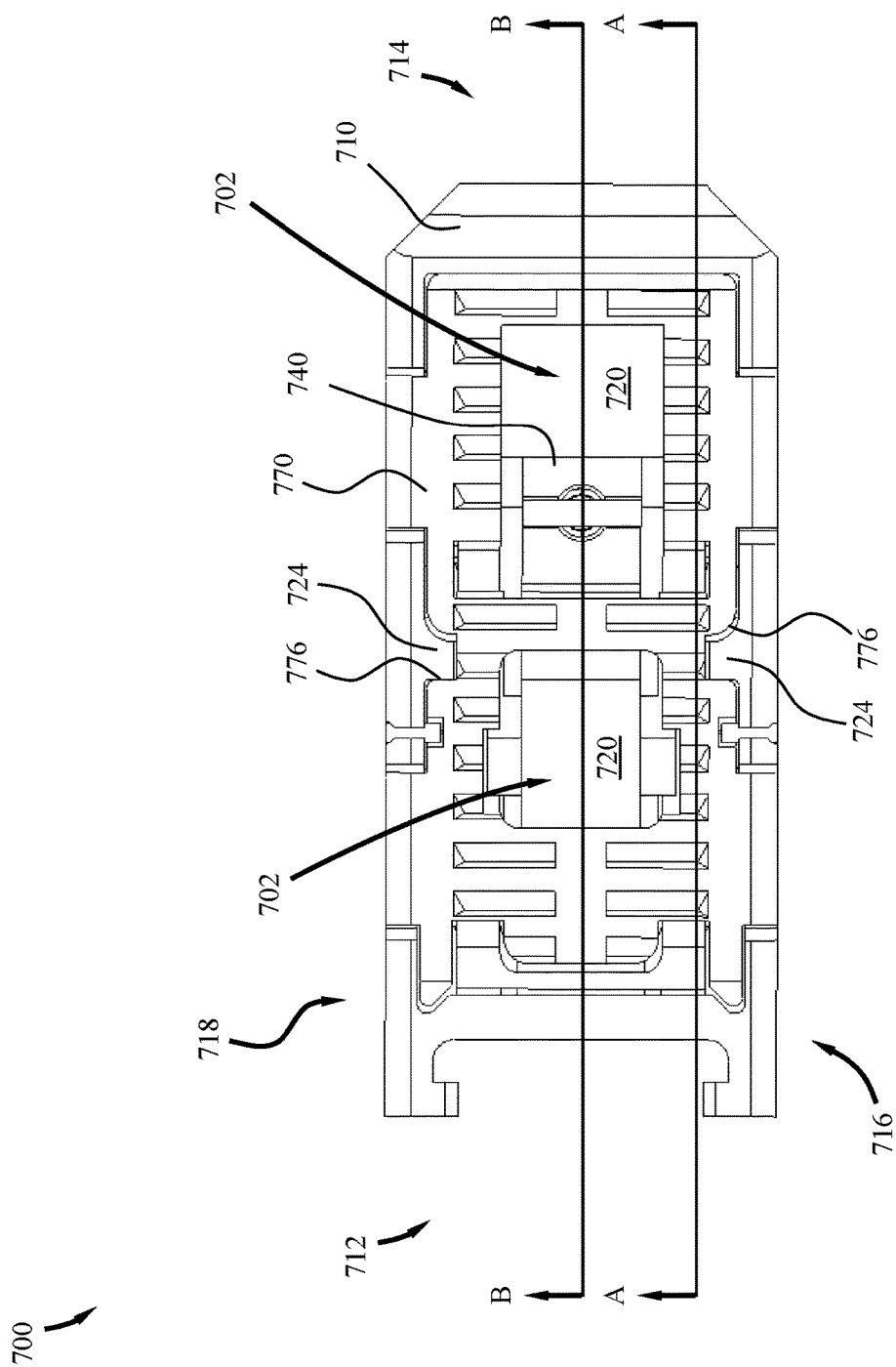
FIG. 1 is a top view of an exemplary intervertebral device.

Intervertebral devices and systems, and methods of their use, are disclosed having configurations suitable for placement between two adjacent vertebrae, replacing the functionality of the disc therebetween. Intervertebral devices and systems contemplated herein are implantable devices intended for replacement of a vertebral disc, which may have deteriorated due to disease for example. The intervertebral devices and systems disclosed or contemplated herein are configured to allow for ample placement of therapeutic agents therein, including bone growth enhancement material, which may lead to better fusion between adjacent vertebral bones. The delivery systems described herein provide increased functionality, such delivery systems utilized for deployment of an intervertebral device within a patient as well as deployment of therapeutic agents to encourage bone growth and healing, such systems being less complex. Also, such intervertebral devices described or contemplated herein are configured to include a top planar surface that is further adapted to include portions that move at one of a plurality of rates as the intervertebral device is expanded, such that the top planar surface forms a desired complex angle with respect to the bottom planar surface as the intervertebral device is expanded. The top planar surface, or element thereof, may be configured to rotate about a rotational axis to achieve the desired complex angle. Certain intervertebral devices may be configured such that the top planar surface rotates about a rotational axis that is perpendicular to a longitudinal axis of the intervertebral device. Alternatively, other intervertebral devices may be configured such that the top planar surface rotates about a rotational axis that is parallel to a longitudinal axis of the intervertebral device. Additionally, still other intervertebral devices may be configured such that the tope planar surface rotates about a rotational axis that is neither perpendicular nor parallel to a longitudinal axis of the intervertebral device. The intervertebral devices and systems may be configured for use in minimally invasive procedures, if desired. Accordingly, the intervertebral device may be adapted to correspond to any suitable approach to the spine described or contemplated herein.

The following description is set forth for the purpose of explanation in order to provide an understanding of the various embodiments of the present disclosure. However, it is apparent that one skilled in the art will recognize that embodiments of the present disclosure may be incorporated into a number of different systems and devices.

The embodiments of the present disclosure may include certain aspects each of which may be present in one or more medical devices or systems thereof. Structures and devices shown below in cross-section or in block diagram are not necessarily to scale and are illustrative of exemplary embodiments. Furthermore, the illustrated exemplary embodiments disclosed or contemplated herein may include more or less structures than depicted and are not intended to be limited to the specific depicted structures. While various portions of the present disclosure are described relative to specific structures or processes with respect to a medical device or system using specific labels, such as "locked" or "therapeutic agents", these labels are not meant to be limiting.

The expandable intervertebral devices described herein may be made from any suitable biocompatible material, including but not limited to metals, metal alloys (e.g. stainless steel) and polymers (e.g. polycarbonate), and may be formed using any appropriate process, such as screw-machining or molding (e.g. injection molding). The intervertebral devices herein may be sized for minimally invasive procedures having operating lumens at about 12 mm or less. For illustration purposes only, any expandable intervertebral device described or contemplated herein may have a height in the range from about 6 mm to about 16 mm, and a length in the range of from about 20 to about 40 mm, and a width in the range of from about 8 mm to about 16 mm. The intervertebral devices described or contemplated herein may be positioned between adjacent vertebrae through any suitable procedure, such as through a posterior lumbar interbody approach or through a transforaminal lumbar interbody approach, for example. Each of the intervertebral devices described or contemplated herein may have a collapsed configuration and an expanded configuration. The intervertebral devices may include a top planar surface and a bottom planar surface, such that when in the collapsed configuration the top planar surface and the bottom planar surface define a first angular relationship and when in the expanded configuration the top planar surface and the bottom planar surface may define a second angular relationship. As the intervertebral device transitions between the collapsed configuration and the expanded configuration, the top planar surface and the bottom planar surface may define one of a plurality of angular relationships. The second angular relationship may be The various intervertebral device embodiments described or contemplated herein may include first, second, and third elements. The first element may also be referred to as a base element. The second element may also be referred to as a sliding element or a first body portion. The third element may also be referred to as a lifting element or a second body portion.

Reference will now be made in detail to the present exemplary embodiments, which are illustrated in the accompanying drawings.

Figure 2:
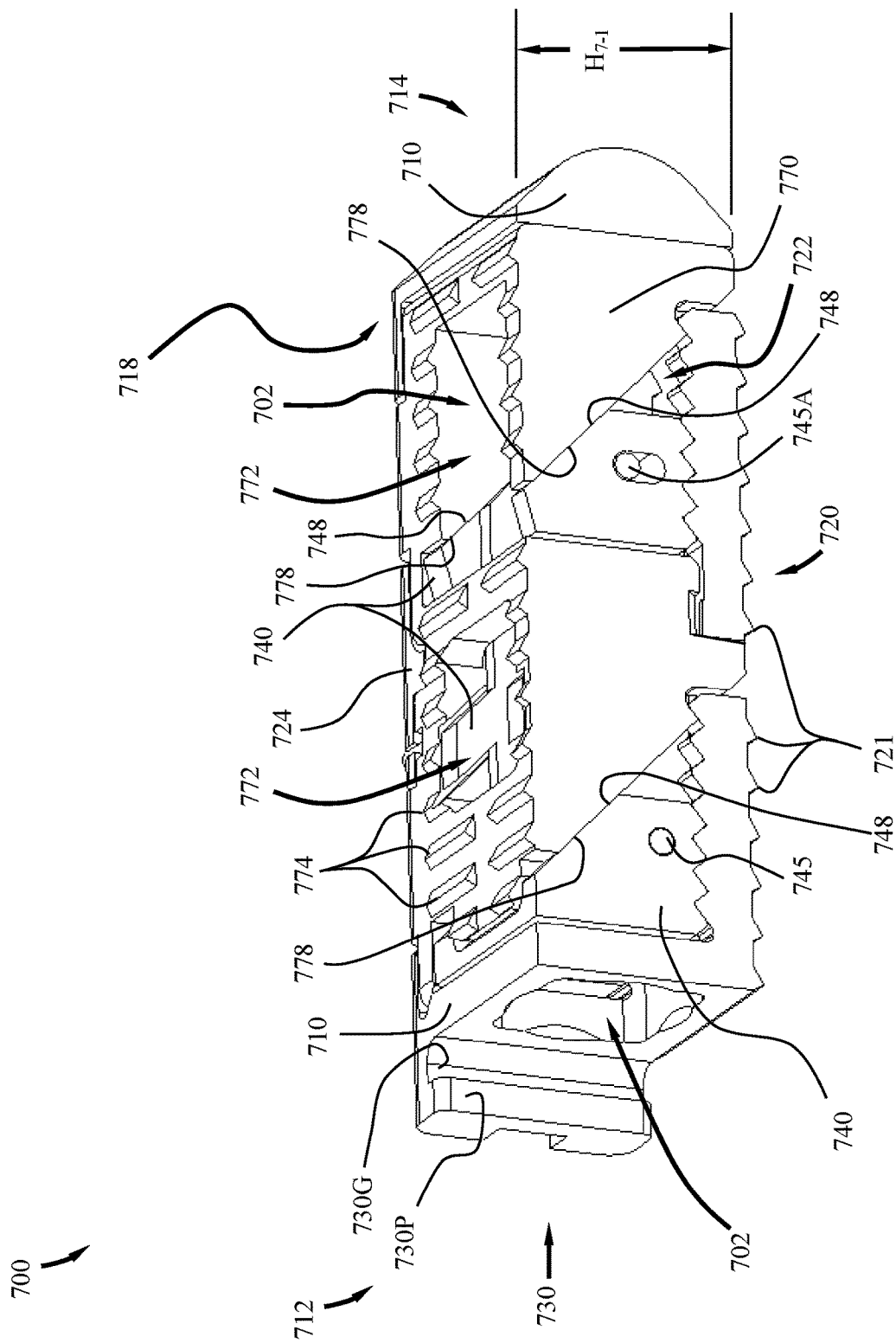
FIG. 2 is a perspective partial section view of the exemplary intervertebral device of FIG. 1.
Figure 3:
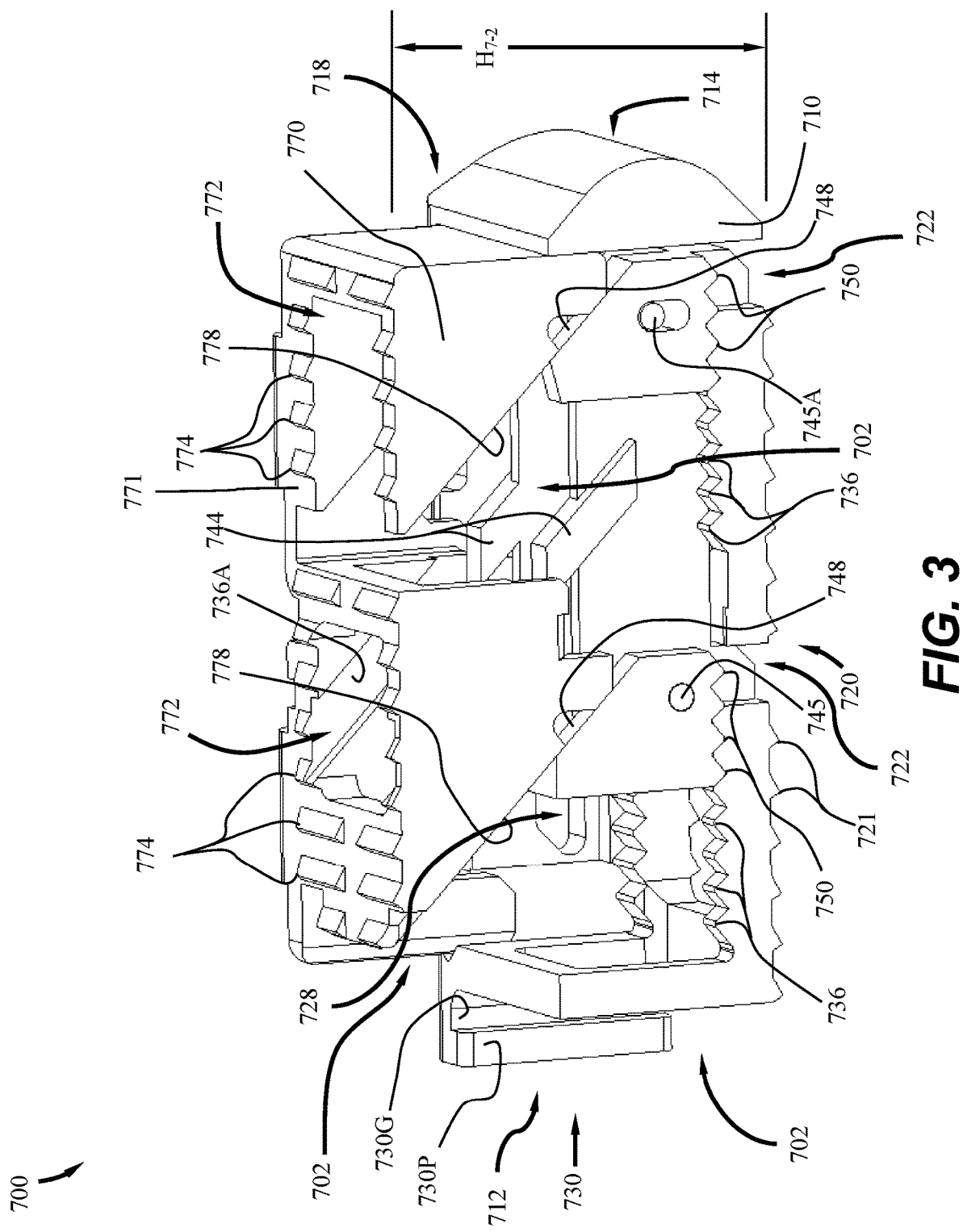
FIG. 3 is another perspective partial section view of the exemplary intervertebral device of FIG. 1.

Turning to FIG. 1, an exemplary intervertebral device 700 includes a first or base element 710, a second element or sliding element 740, and a third element or lifting element 770. The second or sliding element 740 may also be referred to as a first body portion 740, and the third element 770 may also be referred to as a second body portion 770. Turning also to FIGS. 2 and 3, in which perspective views of the exemplary intervertebral device 700 is depicted in cut view along section A-A of FIG. 1. As with other intervertebral devices described or contemplated herein and as better understood in light of the discussion below, the elements 710, 740, 770 cooperate such that the intervertebral device 700 geometric height, $H_7$, may have a minimum, collapsed configuration, as generally depicted in FIG. 2, and a maximum, expanded configuration, as generally depicted in FIG. 3.

The first element 710, also referred to as base 710, or base element 710, is configured to provide a base or outer structure for the intervertebral device 700, and includes a first or proximal end 712, and a second or distal end 714, and two side portions, a first side portion 716 and an opposing side portion 718. A bottom portion 720 may include one or more openings 722 allowing for therapeutic agents to pass therethrough. It should be readily understood that the second and third elements 740, 770 may also include similar openings for transmission of such therapeutic agents, for example. The proximal end 712, may include an opening 730 for passing a portion of one or more tools utilized for delivery of said therapeutic materials, or for expanding, contracting, or locking the intervertebral device 700 in a specific configuration, as discussed below in greater detail with respect to delivery system 800.

The intervertebral device 700 may be expanded or contracted to any suitable height, $H_7$, between a first collapsed height $H_{7-1}$ and a second expanded height $H_{7-2}$, with reference to FIGS. 2 and 3, respectively. For example, the intervertebral device 700 may be expanded from a first position, having the height of $H_{7-1}$ in FIG. 2, to a second position, having the height of $H_{7-2}$ in FIG. 3, or another position therebetween, and locked in that position. The proximal end 712 may also include structures, such as protrusions 730P and grooves 730G, which may allow for attachment points to a delivery system (not shown), as described below with respect to delivery system 800 of FIG. 8. Such attachment points may also form the basis for at least initially positioning the intervertebral device 700, for example between two adjacent vertebrae, within a patient. As described in greater detail below, the delivery system 800 may include tubular members through which therapeutic agents may be introduced, for example, to internal spaces within the intervertebral device 700, and exiting through the one or more openings 722 of the element 710, or similar openings of the remaining elements 740, 770. In this way, such agents or materials may contact surrounding tissues, such as bone tissue.

The third element 770 is slidably interfaced to the first element 710 such that the third element 770 at least slides vertically with respect to the first element 710. The third element 770 may include one or more openings 772 in a top portion or surface 771 thereof to allow for passage or introduction of therapeutic elements or bone growth enhancing materials therethrough. The top portion 771 may include one or more protrusions 774 that may aide in holding the top portion 771 immobile with respect to adjacent structures or biological tissue, such as vertebrae structures for example. While only a few protrusions 774 are identified, additional or less protrusions 774 may be utilized. As with the elements themselves 710, 740, 770, such protrusion structures 774 may be constructed from any biocompatible material and in any suitable form and may be applied to any embodiment described or contemplated herein. Additionally, sidewalls 716, 718 of element 710 may include one or more protrusions (not shown), and a bottom portion 720 of base 710 may include one or more protrusions 721. Protrusions 721 may, for example, may be similar to protrusions 774, which may aide in holding a bottom portion 720 immobile with respect to adjacent structures or biological tissue, such as vertebrae structures for example.

Turning specifically to FIG. 1, the element 710 may include a pair of positioning structures or protrusions 724, which may be configured or adapted to move within one of a pair of corresponding channels 776 of the third element 770, to ensure that the element 770 moves in a specific direction with respect to the element 710. Accordingly, the channel 776 and associated protrusion 724 may be configured to form any desirable angle with respect to a longitudinal axis of element 710. As depicted, the channel 776 of element 770 is substantially perpendicular to a longitudinal axis of element 710 and, therefore, the element 770 moves in a direction substantially perpendicular to the longitudinal axis of element 710.

Turning back to FIGS. 1-3, a void or space 702 is defined by the first, second, and third elements 710, 740, 770 of the intervertebral device 700, the void 702 increasing as the device 700 transitions from a collapsed configuration to an expanded configuration. In this way, once the device 700 is deployed therapeutic agents may be positioned within the void 702 from the first end 712 to the second end 714. Such agents may further flow out of the open space via additional openings, such as openings 772 and 722, positioned about the elements 710, 740, 770.

The third element 770 may include a plurality of sloped surfaces 778 that are configured or adapted to contact a respective one of a plurality of sloped surfaces 748 of second element 740. Accordingly, as the second element or sliding element 740 translates between the first end 712 and the second end 714 of the base element 710, the sloped surfaces 748 contact and slide along corresponding respective sloped surfaces 778 of the third element 770 resulting in movement of the third element 770 in a vertical direction, e.g. defined by channels and wall structures between the first element 710 and the third element 770. Additionally, the movement may be controlled by the sloped surfaces themselves, as discussed below with respect to intervertebral device 1100, among others. As depicted, translation of sliding element 740 from the first end 712 toward the second end 714 results in movement of the element 770 in a vertical direction away from the base element 710. Translation of the sliding element 740 in a direction from the second end 714 toward the first end 712 results in movement of the element 740 in a vertical direction toward the base element 710. As should be readily understood, the sloped surfaces 778, 748 could be configured to be opposite to what is depicted, such that the intervertebral device 700 increases in height as the sliding element 740 transitions from a distal position to a more proximal position.

The first element or base element 710 may further include a plurality of engaging elements 736 protruding from a top inner surface of the bottom portion 720 of element 710. Second element 740 may include a plurality of engaging elements 750, at least one of the elements 750 engaging a respective one of the plurality of engaging elements 736 of the base element 710. While depicted as being integral to the respective elements 710, 740, the engaging elements 736, 750 may be individual parts attached or affixed to the surfaces of the base element 710 and sliding element 740, respectively. The engaging elements 736, 750 are depicted as having similar shapes, e.g., triangular portions, however in other configurations, the shapes can be dissimilar, or may be nonsymmetrical along its vertical central axis, passing through the tip of each element 736, 750.

The intervertebral device 700 is configured such that applying a linear or axial force to the sliding element 740 to translate the element 740 between the first and second ends 712, 714 of base member 710, results in each engaging element 750 sliding up and over a corresponding engaging element 736, and engaging an adjacent engaging element 736 in the direction of the movement of sliding element 740. Accordingly, sliding element 740, while primarily moving along the longitudinal axis of the base element 710, also moves vertically in accordance with the geometry outline and coupling of the engaging elements 750, 736 of the sliding element 740 and base element 710, respectively. As depicted, the engaging elements 750, 736 are positioned within the intervertebral device 700 to better allow for free movement of the various elements 710, 740, 770, prior to application of one or more therapeutic agents, for example.

The intervertebral device 700 may include a plurality of pins 745 coupled to sliding member 740 and extending through corresponding openings 728 in the side portions 716, 718 of base element 710. With the intervertebral device 700 in the collapsed configuration, as depicted in FIG. 2, the sliding element 740 is nearer the first end 712, the pins 745 being nearer the first end 712, as well. With the intervertebral device 700 in the expanded configuration, as depicted in FIG. 3, the sliding element 740 is nearer the distal end or second end 714, the pins 745 being nearer the second end 714, as well. The openings 728 of the first element 710 are spaced to allow some vertical travel of the sliding element 740 and pins 745 in accordance with the geometrical shapes, e.g. height, of the engaging elements 750, 736. It is noted that by adjusting the slope of each side surface of the engaging elements 750, 736 the translational force to move the sliding element 740 in the presence of a compression force between the top portion 771 of element 770 and the bottom portion 720 of the base element 710 may differ in accordance with the corresponding element 750, 736 sloped surfaces. The slopes of each side surface of the engaging elements 750, 736, which may be linear or may be nonlinear, may be configured to encourage movement of the sliding element 740 in a first direction along the longitudinal axis of the base 710 with respect to the sliding element 740 in a second opposite direction. In any case, the engaging elements 750, 736 are configured, e.g., with suitable sloped surfaces or the like, to become locked or immovable when a compression force exists between the third element 770 and the base element 710.

Turning specifically to FIG. 3, the sliding element 740 may include a protrusion 744 configured or adapted to slidably interface with a corresponding recessed portion or groove 736A along the inner wall of the third element 770. The protrusion 744 cooperates with recessed portion 736A such that when the sliding element 740 translates in a proximal direction, in a direction toward proximal end 712 of the intervertebral device for example, the surfaces of the protrusion 744 may engage surfaces of the recessed portion 736A to encourage the third element 770 to move vertically toward the first element 710.

In the presence of a linear force applied to sliding element 740 moving the element 740 toward end 714, in a ratcheting manner, for example, the engaging elements 750, 736 continuously engage and disengage with adjacent opposing engaging elements 750, 736. As the element 740 translates, the third element 770 moves vertically to increase the overall height, $H_7$, of the device 700. With a compression force applied between the third element 770 and the base element 710, e.g. when the device 700 is positioned between adjacent tissue surfaces, such as two adjacent vertebrae, the engaging elements 750, 736 of the sliding element 740 and base element 710, respectively, engage and prevent the sliding element 740 from further translating. For illustration purposes only, the sliding element 740 of the intervertebral device 700 may be translated through the use of a tool, such as exemplary delivery system 800 described below, the protrusion 730P and groove 730G of the base element 710 adapted to interface with the delivery system 800, for example.

Turning to FIGS. 4 and 5, the intervertebral device 700 is depicted in elevation cut view along section B-B, a longitudinal centerline, of FIG. 1. The intervertebral device 700 is depicted in a collapsed configuration in FIG. 4 and an expanded configuration in FIG. 5. In particular, the sliding element 740 includes a retention device 760 to aide in maintaining contact between the engaging element 750, 736 of the sliding element 740 and base element 710, respectively. The retention device 760 includes a pin 745A and a spring 747, the spring 747 seated in a corresponding bore 746. As depicted, the pin 745A may extend from a first opening 723 in side portion 716 to a second opening 723 in side portion 718 (not shown). The pin 745A includes a protrusion 762 that extends from a central longitudinal axis of the pin 745A toward the bottom 720 of the first element 710. In operation, as the sliding element 740 translates between the two ends 712, 714, the engaging elements 750, 736 repeatedly engage and disengage resulting in the sliding element 740 repeatedly moving vertically away from and toward to the bottom portion 720 of the base element 710. As the sliding element 740 moves away from the base element 710 the ends of the pin 745A engage the top surfaces of the corresponding openings 723 in respective side portions 716, 718, acting to compress the spring 747. As the engaging elements 750 of the sliding element 740 pass over the corresponding engaging elements 736 of the base element 710 the spring imparts a force upon the sliding element 740 to encourage re-engagement of the adjacent engaging elements 750, 736. In this way, the engaging elements 750 are biased to remain coupled to corresponding engaging elements 736 during each movement of the sliding element 740, particularly in a no-load situation, where the force between the third element 770 and the first element 710 is minimal, for example. Accordingly, when a compression force is applied between the top surface 771 of the third element 770 and the bottom surface 720 of the base element 710, engaging elements 750, 736 maintain the current position of all three elements 710, 740, 770 and, ultimately, the current height, $H_7$, of the intervertebral device 700.

Figure 6:
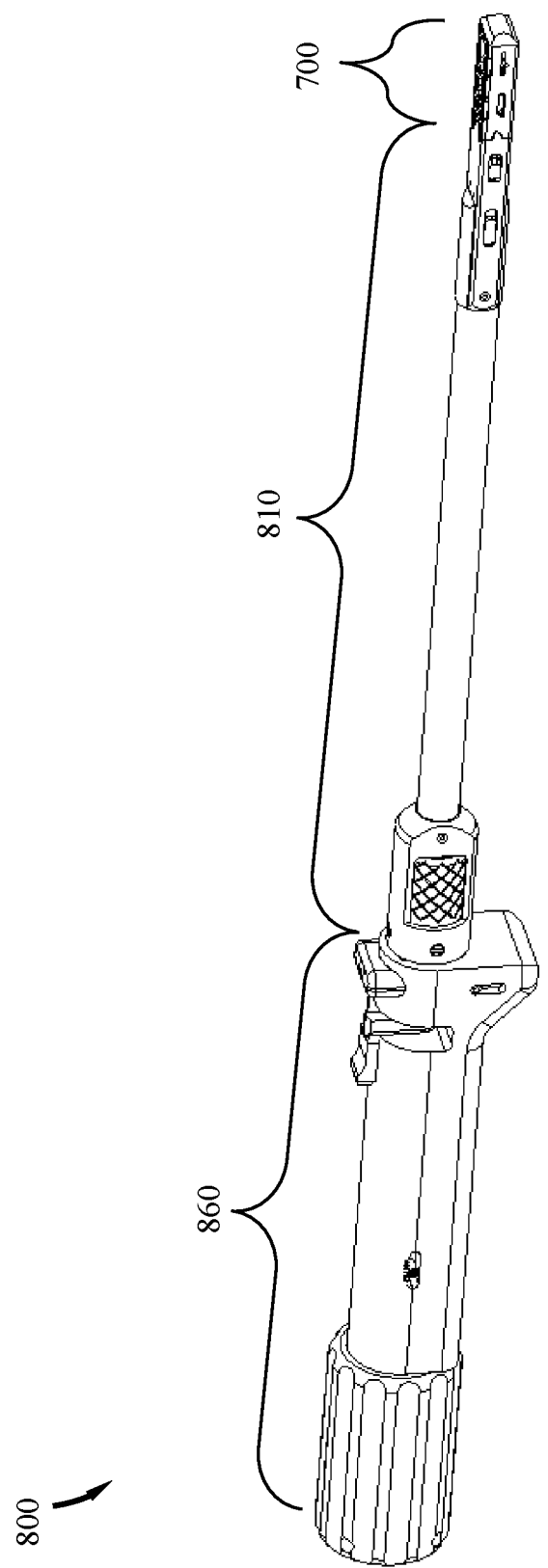
FIG. 6 is a perspective view of an exemplary delivery device.
Figure 7:
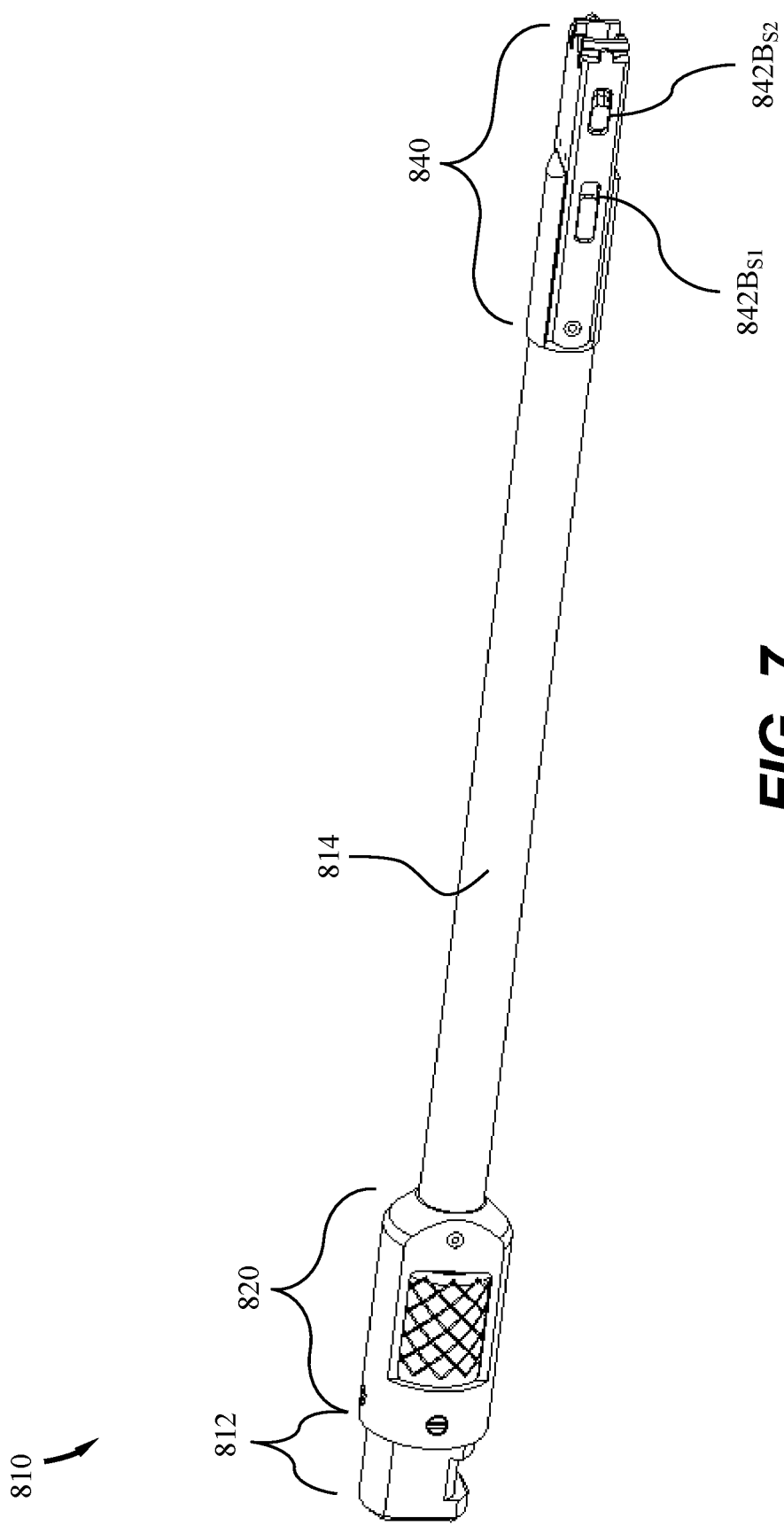
FIG. 7 is a perspective view of a portion of the exemplary delivery device of FIG. 6.

Turning to FIG. 6, a delivery system 800 for positioning and operating intervertebral device 700, or other intervertebral devices described or contemplated herein, includes an attachment assembly 810 and an expansion tool 860. The attachment assembly 810 is utilized for attaching an intervertebral device, such as intervertebral device 700, to the delivery system 800. The expansion tool 860 is utilized for setting a height of the intervertebral device 700 once the device 700 has been deployed, between adjacent vertebrae for example. Turning to FIG. 7, the attachment assembly 810 may include an interface unit 812, a control assembly 820, a grasper unit 840, and an elongate member 814 that extends from the control assembly 820 to the grasper unit 840. The interface unit 812 is configured to attach the attachment assembly 810 to the expansion tool 860, as is discussed in greater detail below. The elongate member 814 may be of any suitable length to allow for placement of an intervertebral device at a desired location within a patient, while allowing for control from a point external to the patient. The elongate member 814 may include one or more lumens or members therein for controlling the grasper unit 840 or the intervertebral device 700, or for transmission of therapeutic agents to a corresponding void within the intervertebral device, such as void 702 of the device 700.

Turning to FIGS. 8-11, operation of the grasper unit 840 will be described in greater detail. The grasper unit 840 includes a housing 842 having first and second pairs of slots $842A_{S1}$, $842A_{S2}$, $842B_{S1}$, $842B_{S2}$, and a control ring 844 operational coupled to first and second arms 846A, 846B. The elongate member 814 may be fixedly coupled to the housing 842 via pins 815, for example. An elongate member 816 passes through a lumen of the elongate member 814, and includes a threaded portion 816T that is rotationally coupled to threaded portion 844T of the control ring 844. Rotational movement of the elongate member 816 is transformed into axial movement of the control ring 844 through treaded portions 816T, 844T. First arm 846A includes first and second protrusions $846A_{P1}$, $846A_{P2}$ positioned within the first pair of slots $842A_{S1}$, $842A_{S2}$, respectively, and a third protrusion $846A_{P3}$ at a distal tip of the arm 846A. Similarly, second arm 846B includes first and second protrusions $846B_{P1}$, $846B_{P2}$ positioned within the second pair of slots $842B_{S1}$, $842B_{S2}$, respectively, and a third protrusion $846B_{P3}$ at a distal tip of the arm 846B. With momentary reference to FIG. 7, slots $842B_{S1}$, $842B_{S2}$ are depicted as part of the grasper unit 840. Slots $842A_{S1}$, $842A_{S2}$ are similar to slots $842B_{S1}$, $842B_{S2}$, respectively, and are located on the opposite side of grasper unit 840. As depicted in FIG. 8, arm 846A includes a raised portion 848A configured to engage a surface of housing 842. More specifically, the raised portion 848A includes a surface $848A_S$ configured to engage a surface $843A_S$ of the housing. In similar fashion, arm 846B includes a raised portion 848B having a surface $848A_S$ configured to engage a surface $843A_S$ of the housing 842. Accordingly, as the housing 842 moves distally relative to the arms 846A, 846B, a distance between the protrusions $846A_{P3}$, $846B_{P3}$ increases.

Figure 10:
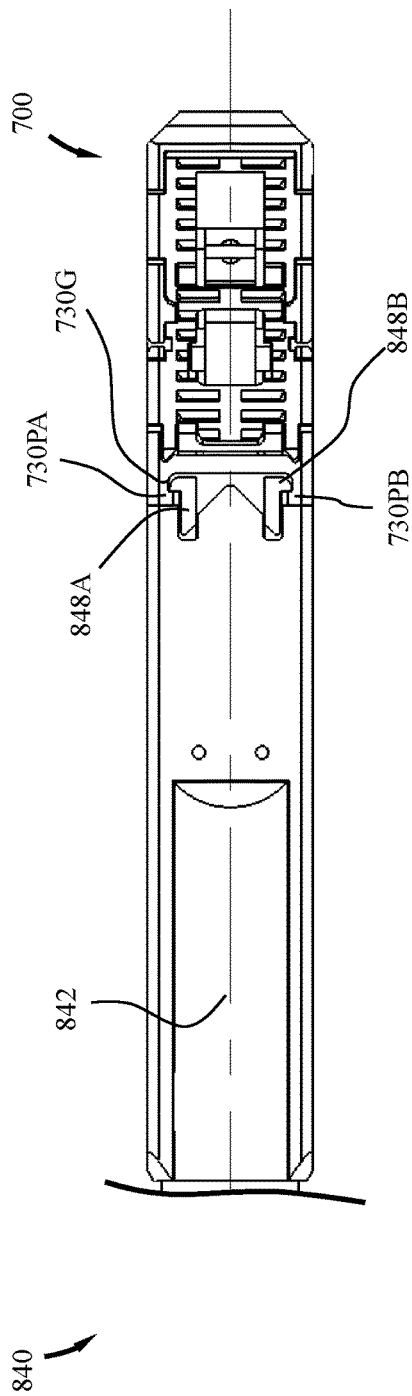
FIG. 10 is another top view of the element of the portion of the exemplary intervertebral device of FIG. 7.
Figure 11:
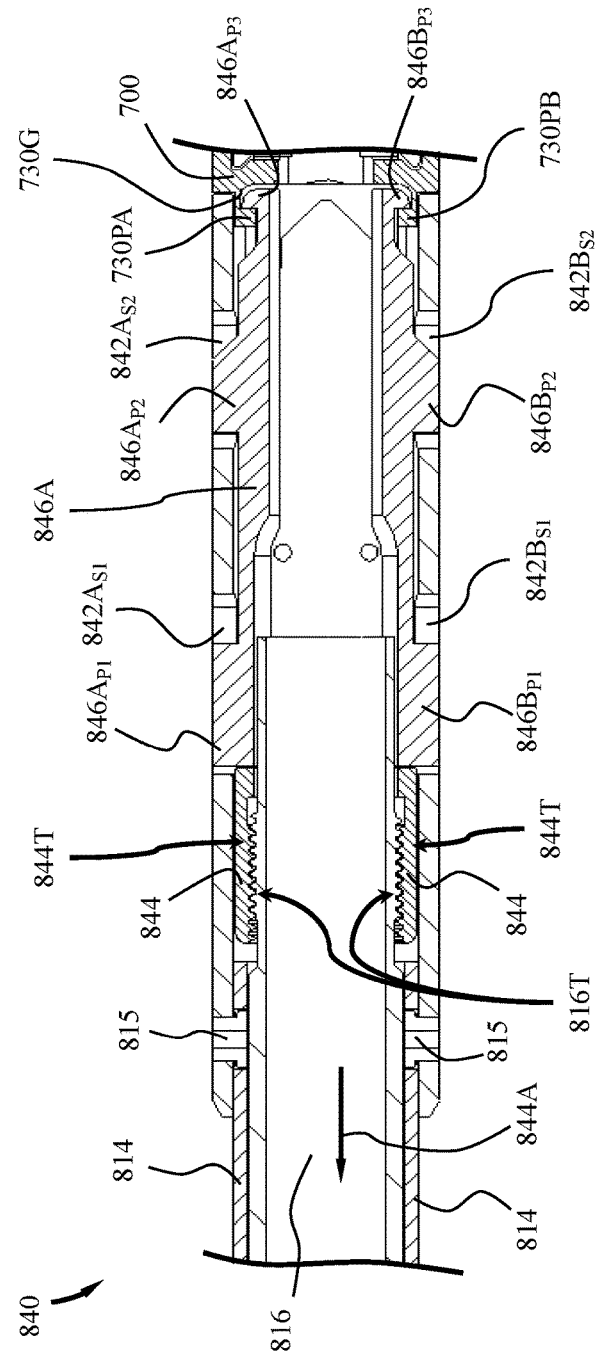
FIG. 11 is another partial section view of the element depicted in FIG. 8.

FIGS. 8 and 9 depict the arms 846A, 846B in an open configuration, while FIGS. 10 and 11 depict the arms 846A, 846B in a closed configuration, the arms 846A, 846B being closer to each other in the open configuration than in the closed configuration. In operation, rotation of the elongate member 816 in a first direction results in axial movement of the control ring 844 as indicated by arrow 844A. Since the control ring 844 is coupled to the arms 846A, 846B, the arms move in the same direction as the control ring, and the surfaces $848A_S$, $848B_S$ cooperate with surfaces $843A_S$, $843B_S$ of housing 842 to move the arms apart from each other, e.g., transitioning to a closed configuration for example. Continued axial movement of the control ring results in moving the arms 846A, 846B axially to clamp onto the proximal features 730PA and 730PB. Rotation of the elongate member 816 in a second direction opposite to the first direction, results in axial movement of the control ring 844 in a direction opposite to that indicated by arrow 844A. As the control ring 844 moves distally with respect to housing 842, as well as arms 846A, 846B, distal surfaces of protrusions 846A$_{P2}$, 846B$_{P2}$ engage or cooperate with distal portions of slots 842A$_{S2}$, 842B$_{S2}$, respectively, to deflect the arms inward. Accordingly, the more the arms 846A, 846B move distally with respect to the housing 842, the more the distal protrusions 846A$_{P3}$, 846B$_{P3}$ move distally and toward to each other, disengaging from the attachment point, and being free from the profile of the protrusions 730PA and 730PB, of the intervertebral device 700. While actuation of the arms 846A, 846B has been described in terms of interfering with slots 842 other methodologies may be used. For example, the housing may include pins that travel in slots within the arms 846A, 846B (not shown), the slots configured to interfere and deflect the arms 846A, 846B as they translate distally or proximately. Alternatively, the pins may be attached to the arms 846A, 846B, and configured to move within corresponding slots in the housing to achieve the desired deflection.

Turning to FIGS. 12A-12C, the interaction between the control ring 844, arms 846A, 846B, and the elongate member 816 is depicted. The control ring 844 includes first and second "T" slots 845, each coupled to a proximal end of one of the arms 846A, 846B, as depicted in FIG. 12B. The coupling point between the slots 845 and the arms 846A, 846B allows for the distal protrusions 846A$_{P3}$, 846B$_{P3}$ to move toward and away from each other to enable a position for coupling between the arms 846A, 846B and the intervertebral device 700. FIG. 12C depicts the control ring 844 rotatably coupled to the elongate tube 816.

Figure 13:
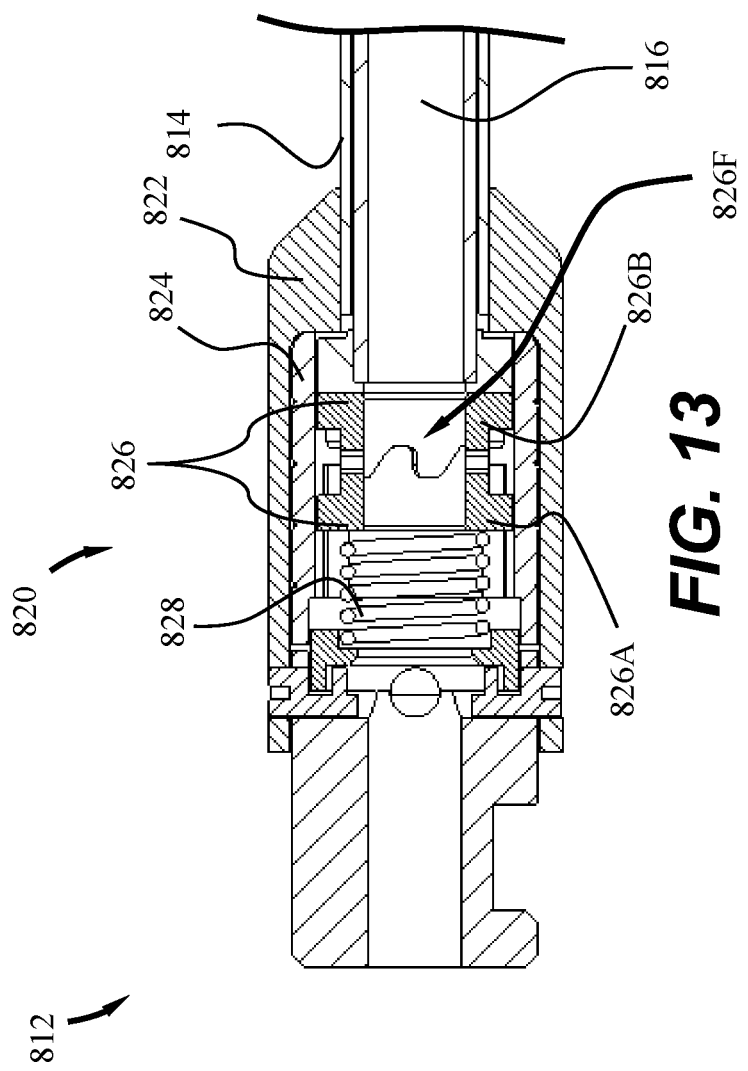
FIG. 13 is a partial section view of a portion of the exemplary delivery device of FIG. 6.

Turning to FIG. 13, the interface unit 812 is fixedly attached to the control assembly 820, and the control assembly 820 is fixedly attached to elongate member 814. The control assembly 820 includes a rotatable control 824, a clutch assembly 826, and a spring 828. The rotatable control 824 is rotationally attached to a clutch member 826A, as part of a clutch assembly 826. A clutch member 826B is fixedly attached to elongate member 816. The spring 828 provides a force to encourage coupling between clutch member 826A and clutch member 826B at fingers 826F. The fingers 826F are configured such that rotation of the rotatable control 824 in a first direction results in constant engagement of the fingers, and rotation of the rotatable control 824 in a second direction opposite to the first direction results in the fingers of clutch member 826A slipping past the fingers of clutch member 826B once the rotational torque becomes greater than the force applied by the spring 828 on the clutch member 826A. In this way, rotation of the rotatable control 824 in the second direction results in the arms 846A, 846B coupling to the attachment point of the intervertebral device 700, without over-tightening the connection which may result in undue stress in the delivery system 800 or the intervertebral device 700, or both. It should be understood that the interface of the fingers 826F may be adapted to provide a desired rotational torque such that the fingers of the clutch members 826A, 826B slip.

Figure 14:
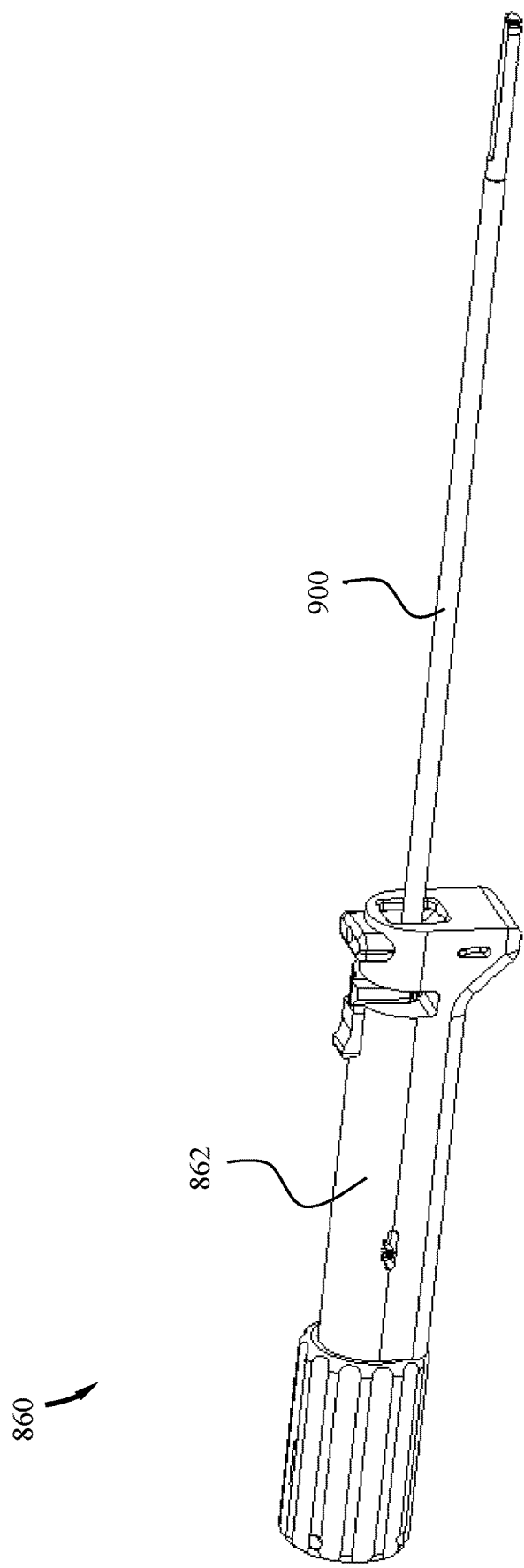
FIG. 14 is a perspective view of an expansion tool of the exemplary delivery device of FIG. 6.

Turning to FIG. 14, the expansion tool 860 includes a handle or handle portion 862 and an elongate shaft 900 rotatably coupled to the handle 862. The expansion tool 860 is utilized for moving the second element, for example the second element 740 of the intervertebral device 700, along a longitudinal axis of the first element 710 to set a height of the intervertebral device 700 once the device 700 has been deployed, between adjacent vertebrae for example.

Figure 15A:
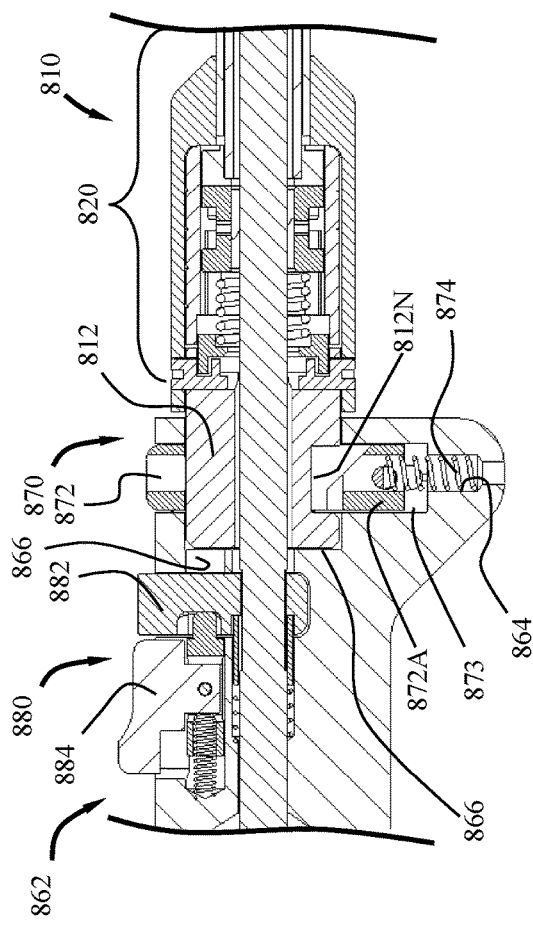
FIGS. 15A-15B are partial section views of portions of the delivery device of FIG. 6.
Figure 15B:
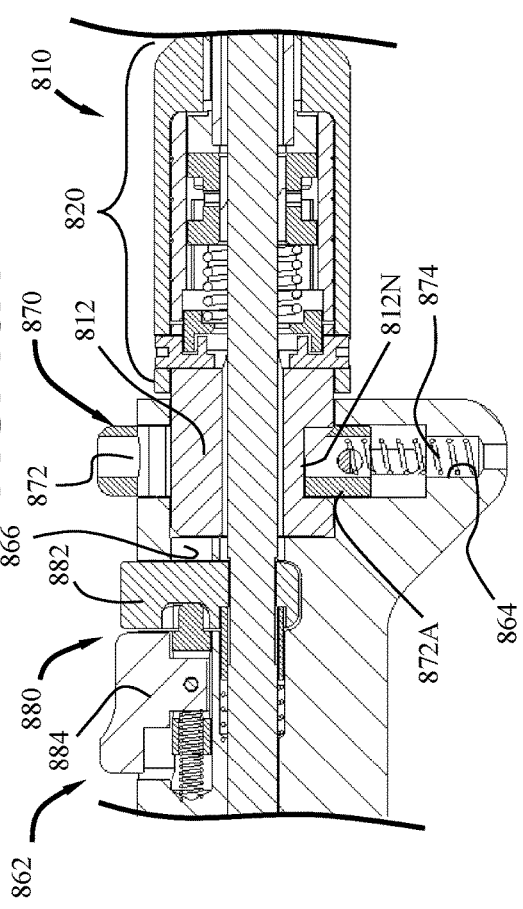

Turning to FIGS. 15A and 15B, handle portion 862 is depicted in section view and includes an interface assembly 870 and an attachment control 880. The interface assembly 870 is configured to attach or interface the handle portion 862 with the attachment assembly 810. More specifically, the interface assembly 870 interfaces with the interface element 812 of the attachment assembly 810. The interface assembly 870 includes a pushbutton 872 in a slotted portion 873 of the handle 862. The pushbutton 872 is biased by a spring 874, which is positioned within a bore 864 of the handle 862. With specific reference to FIG. 15A, when the pushbutton 872 is depressed, compressing the spring 874, the interface element 812 of the attachment assembly 810 may be positioned within an opening 866 within the handle 862. The interface element 812 includes a notch 812N sized to be equal to or greater than a width of the pushbutton 872, such that once the interface element 812 is positioned within the opening 866 the pushbutton 872 may be released and a portion 872A of the pushbutton 872 is positioned within the notch 812N, as depicted in FIG. 15B.

Attachment control 880 is utilized to engage the second element, for example second element 740, with the elongate shaft 900. The control 880 includes a lever 882 rotatably coupled to the shaft 900, the lever 882 being configured to rotate the shaft to enable engagement of the shaft 900 with the second element 740. The control 880 may further include a slide lock 884, which is configured to lock the lever control 882 such that the shaft 900 is maintained in a desired rotational orientation, during operation of an intervertebral device for example.

Figure 16A:
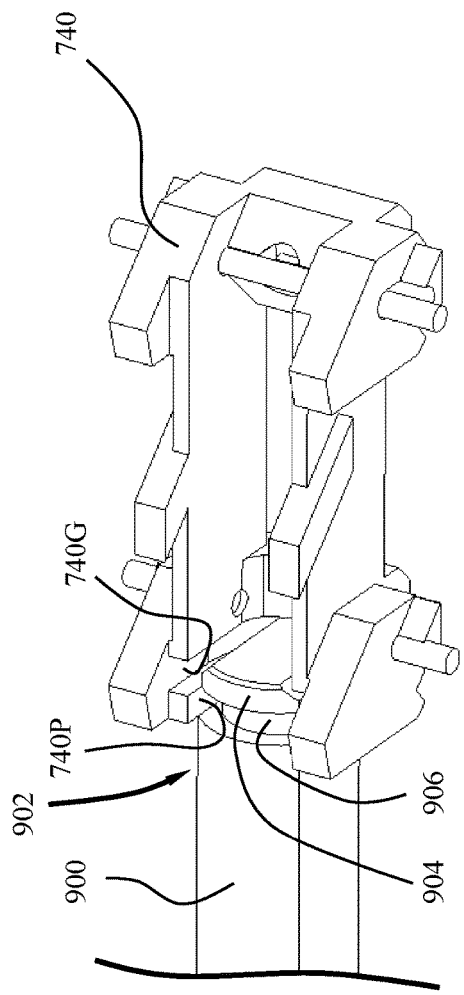
Figure 16B:
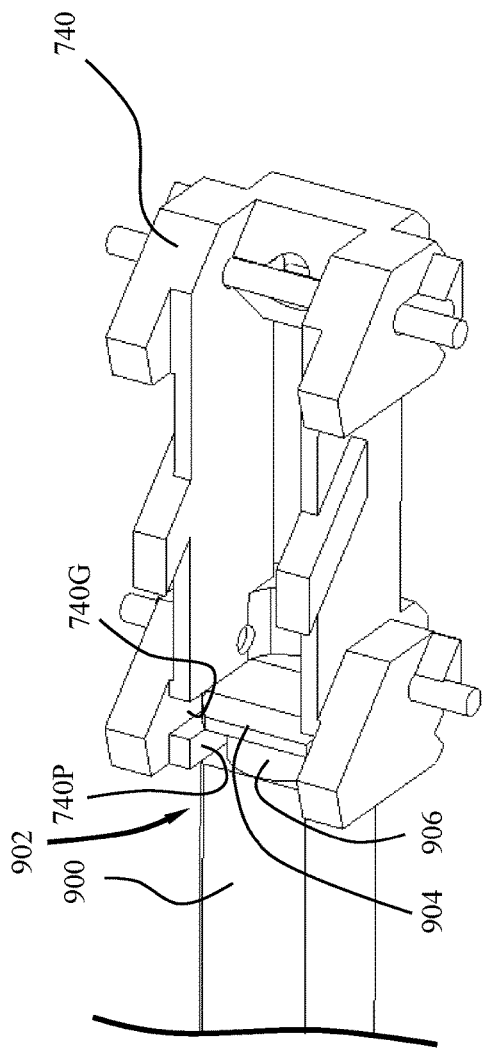

Turning to FIGS. 16A and 16B, a distal end 902 of elongate shaft 900 includes a protrusion 904 adjacent to a groove 906. The protrusion 904 may be adapted to fit a corresponding groove 740G at a proximal end of the sliding element 740. As depicted in FIG. 16A, the shaft 900 is angled or rotated along its axis such that the protrusion 904 freely enters the proximal end of the sliding element 740. Once inserted, the shaft 900 may be rotated, through operation of the attachment control 880 for example, such that the protrusion 904 is positioned within the groove 740G and held in place through the cooperation of the protrusion 904 and a protrusion 740P at the proximal end of sliding or third element 740, as depicted in FIG. 46B. The groove 740G of the sliding element 740 cooperates with the protrusion 904 of the shaft 900 to rigidly attach the shaft 900 to the element 740. Once the shaft 900 is rigidly attached to the sliding element 740 a user can translate the sliding element 740 through corresponding translation of the shaft.

Turning to FIGS. 17 and 18, the handle 862 may also include an axial control 890 configured to translate the shaft 900 in proximal and distal directions, in a manner similar to how the elongate member 816 translates, for example. The axial control 890 includes a rotational control 892 rotationally coupled to a short shaft 894, the short shaft 894 having threaded portion 894T that interfaces with corresponding threaded portion 862T of the handle 862, the short shaft 894 being coupled to the shaft 900. FIG. 17 depicts handle 862 without the rotational control 892. Shaft 900 is axially coupled, not rotationally coupled, to the short shaft 894. Accordingly, the axial control 890 converts rotational movement of the rotational control 892 into axial movement of the shaft 900. As the rotational control 892 is rotated in a first direction the short shaft 894 rotates and moves distally within the handle portion 862, which acts to move shaft 900 distally. As the rotational control 892 is rotated in a second direction the short shaft 894 rotates and moves proximally within the handle portion 862, which acts to move shaft 900 proximally. For example, translation of the shaft 900 results in the translation of the sliding element 740, further resulting in the sliding element 740 moving between the ends 712, 714 of the base member 710. As the sliding element 740 translates or moves between the ends 712, 714, the element 770 moves in a vertical direction with respect to the base element 710 to change the overall height, $H_7$, of the intervertebral device 700.

As depicted, the axial control 890 may utilize a clutch 826C, similar to clutch 826 of the control assembly 820. Such a clutch system may act to limit the axial force of the shaft 900, which may limit damage to the intervertebral device, or to the patient.

Figure 19:
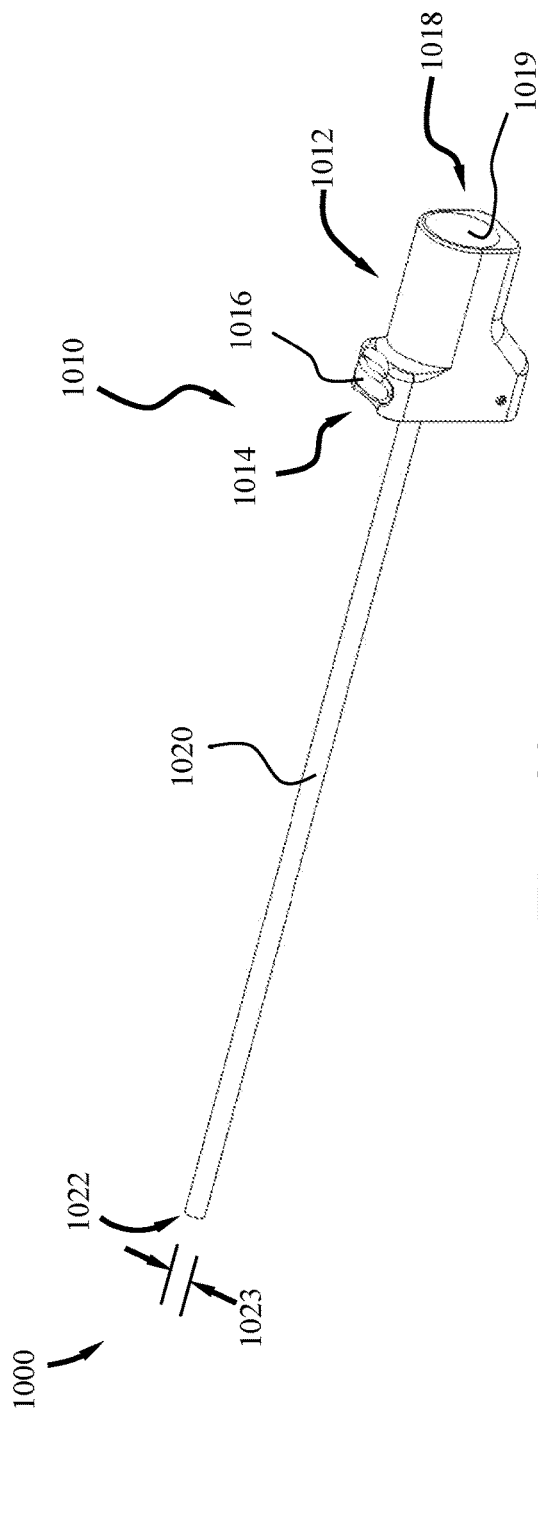
Figure 20:
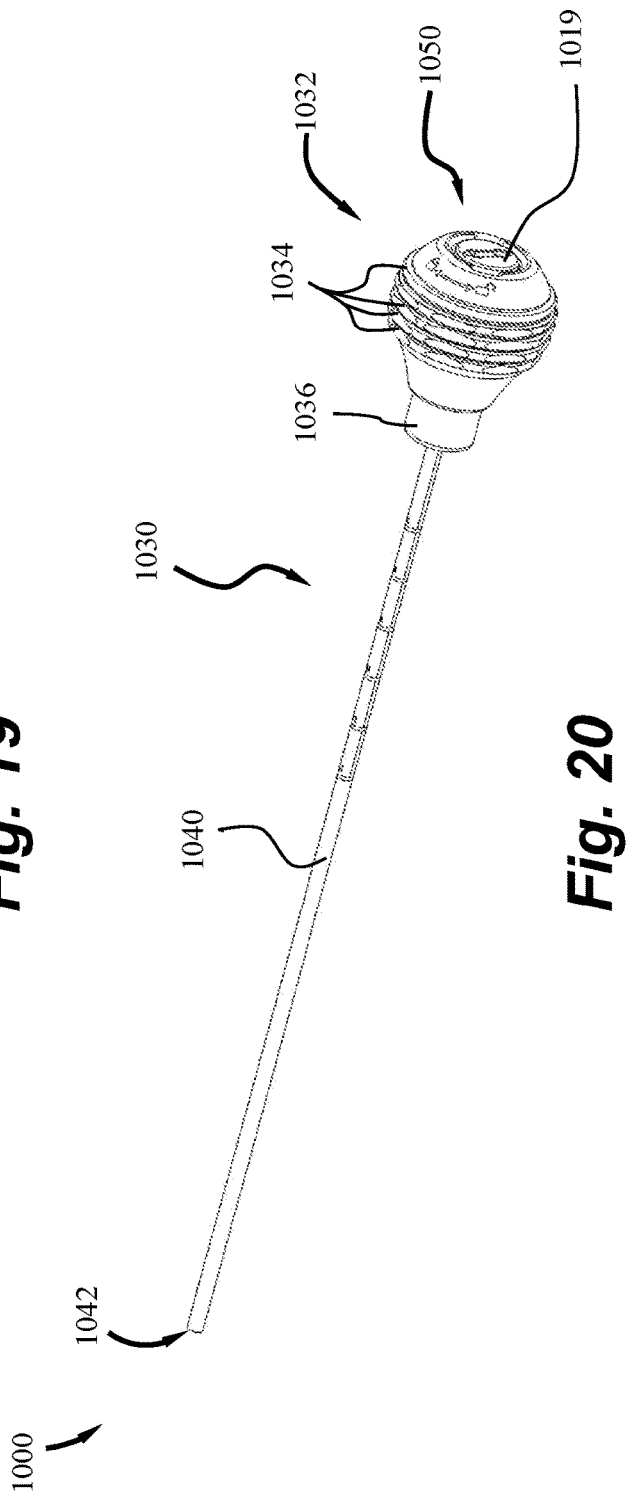

Turning to FIG. 19, the delivery system 800 may further include a delivery tool configured to deliver therapeutic agents, such as those therapeutic agents described or contemplated herein, to an intervertebral device, such as those intervertebral devices described or contemplated herein, which may be positioned or deployed between adjacent vertebra. The delivery tool 1000 may include a guide assembly 1010 and an insertion assembly 1030, as better viewed in FIG. 20. The guide assembly 1010 may include a handle portion 1012 and a tubular member 1020, the tubular member having one end fixedly attached to the handle portion 1012. The tubular member 1020 may include a lumen 1022 therethrough, the lumen having an inner diameter 1023 and being in fluid communication with a lumen 1018 passing through the handle portion 1012. The lumen 1018 may include an inner diameter sized similar to the lumen 1022 of the tubular member 1020 at or near where the tubular member 1020 is attached to the handle portion 1012, and then may increase such that an inner surface 1019 of the lumen 1018 may be configured to accept a portion of the insertion assembly 1030, as described in greater detail below.

The handle portion 1012 may also include an interface assembly 1014, similar to interface assembly 870 of the expansion tool 860 as part of the delivery system 800, and discussed with respect to FIGS. 15A and 15B above, the interface assembly 1014 configured to attach or interface the handle portion 1012 with the attachment assembly 810 of delivery system 800, for example. More specifically, the interface assembly 1014 may include a pushbutton 1016 and interface with the interface element 812 of the attachment assembly 810 in a similar fashion as interface assembly 870, as described in greater detail above with respect to FIGS. 15A and 15B.

Turning also to FIG. 21, the insertion assembly 1030 is depicted in partial section view and may include a handle portion 1032, shown in bulbous form, and an elongate member 1040, which may be fixedly attached at one end to the handle portion 1032. The elongate member 1040 may include a lumen 1042 therethrough and may include an outer diameter sized to allow the member 1040 to translate within the lumen 1022 of elongate member 1020 of the guide assembly 1010. The insertion assembly 1030 may include a plunger assembly 1050 having a plunger control 1052 coupled to an elongate shaft 1054, which may also be viewed in FIG. 25A, the elongate shaft 1054 sized to translate within the lumen 1042 of tubular member 1040.

The handle portion 1032 may include one or more surface protrusions 1034 which may allow better grip and control of the insertion tool 1030 during use. Handle portion 1032 may also include a cylindrical distal portion 1036, which may be sized to interface with and translate within a portion of the lumen 1018 of handle portion 1012.

With specific reference to FIGS. 21 and 22, the plunger assembly 1050, as part of the insertion assembly 1030, is shown coupled to the guide assembly 1010. The cylindrical distal portion 1036 of the insertion assembly 1030 is slidably positioned within a portion of lumen 1018 of the handle portion 1012 of the guide assembly 1010. As shown, the plunger control 1052 is coupled to shaft 1054 and configured to selectively translate within the lumen 1042 of the elongate member 1040 of the insertion assembly 1030. The plunger assembly 1050 may include a retaining ring 1056, a spring retainer 1058 and a spring 1060. The retaining ring 1056 is fixedly attached to the shaft 1054 and retains the spring retainer 1058 and the spring 1060 about the elongate member when the plunger assembly 1050 is decoupled and removed from the insertion assembly 1030, for sterilization purposes for example. The retaining ring 1056 is fixedly attached to the shaft 1054 and is slidably received within a lumen 1038 of the handle portion 1032. The spring retainer 1058 is slidably coupled to the shaft 1054 and, along with the plunger control 1052, retains the spring 1060. Spring 1060 allows for momentary movement of the plunger assembly 1050, as discussed in greater detail below.

The plunger control 1052 may include one or more tab portions 1052T, which may be slidably coupled with compatible slot portions 1032S of the handle portion 1032. A retaining portion 1032R of the handle portion 1032 may be positioned adjacent to a corresponding slot portion 1032S and may prevent the decoupling and removal of the plunger assembly 1050 from the insertion assembly 1030. Certain slot portions 1032S, such as specific slot portion 1032S1, may be provided without a retaining portion 1032R allowing a user to rotate the plunger assembly 1050 with respect to the insertion assembly 1030, aligning the tabs 1052T with the corresponding slot portions 1032S1 (only one shown in the cross section view of FIGS. 22 and 22) allowing for decoupling and removal of the plunger assembly 1050 from the guide assembly 1010, for purposes of sterilization for example.

The shaft 1054 of the plunger assembly 1050 may translate within the lumen 1042 of the elongate member 1040 of the insertion assembly 1030, and may be utilized to deploy one or more therapeutic agents within an intervertebral device, such as one or more of the intervertebral devices described or contemplated herein. The applied one or more therapeutic agents may fill the internal voids of the intervertebral device, and exit one or more openings thereof, the therapeutic agents coming into contact with surrounding tissue, vertebral tissue for example. To assist in deployment of a therapeutic agent, the plunger control 1052 may be depressed with respect to the remaining of the plunger assembly 1050 and guide assembly 1010, a distal end of the elongate shaft 1054 deploying the therapeutic agent. FIG. 21 depicts the plunger control 1052 in a rest position, and FIG. 22 depicts the plunger control 1052 in a depressed position. While in the depressed position, the plunger control 1052 may compress the spring 1060 between the spring retainer 1058 and the plunger control 1052. When application force is removed from the plunger control 1052, the spring 1060 acts to move the plunger control 1052 back to its resting position, as depicted in FIG. 21. It should be noted that the various characteristics of the plunger assembly 1050 and the insertion assembly 1030 may be modified to provide a desired amount of travel of the elongate shaft 1054 when the plunger control 1052 is depressed, resulting in a corresponding amount of therapeutic agent deployed for example.

Figure 24A:
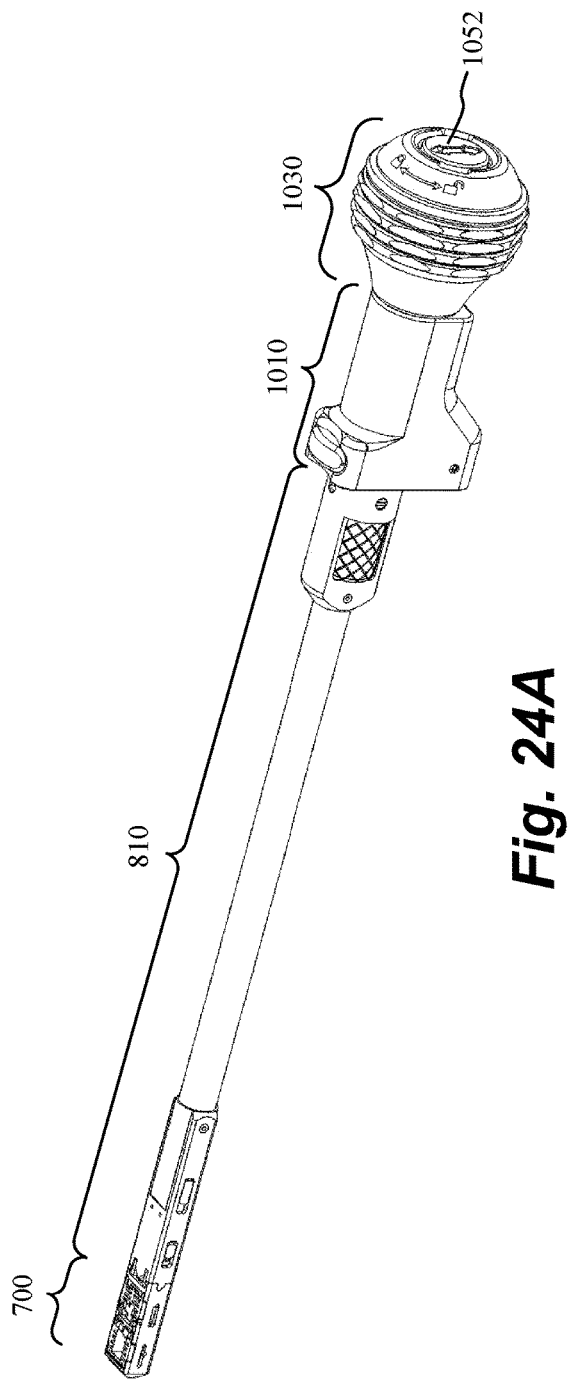
FIG. 24A is another perspective view of the guide assembly of FIG. 19 and the insertion assembly of FIG. 20 coupled to an exemplary attachment assembly.
Figure 24B:
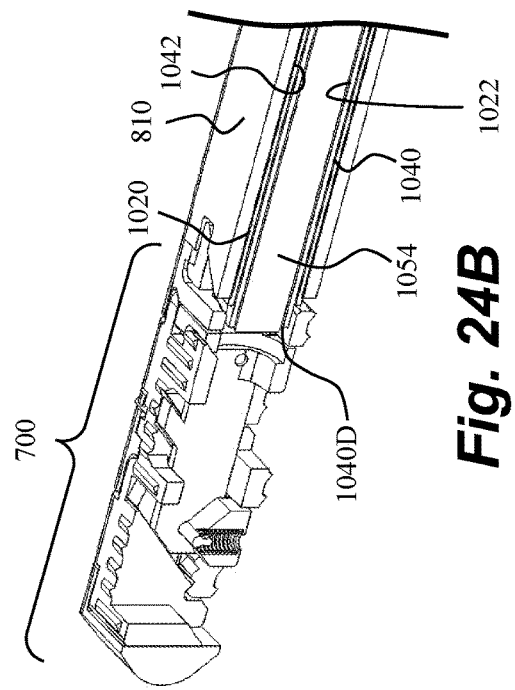
FIG. 24B is a partial section view of a distal portion of a delivery system.
Figure 25A:
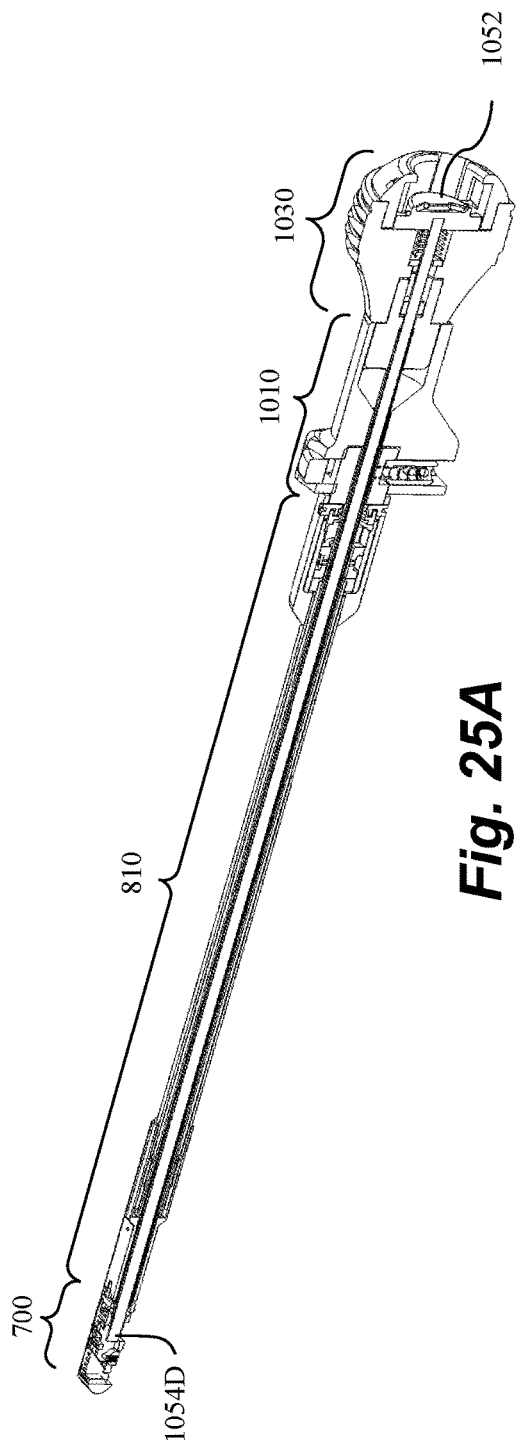
FIG. 25A is a partial section view of the guide assembly of FIG. 19 and the insertion assembly of FIG. 20 coupled to an exemplary attachment assembly.
Figure 25B:
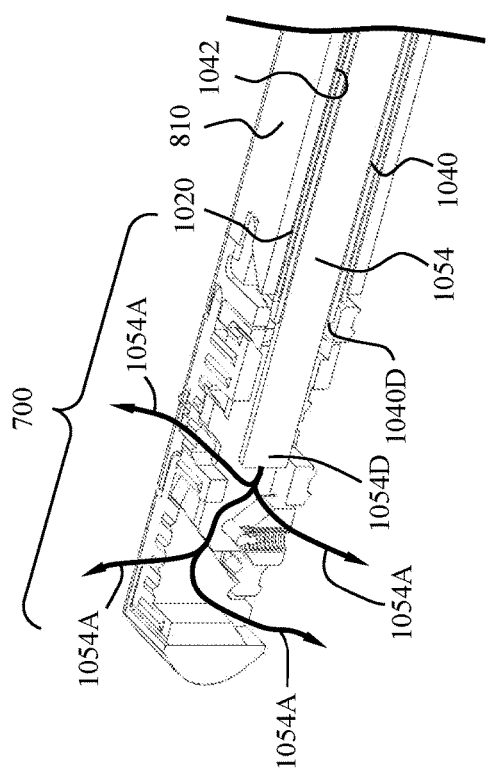
FIG. 25B is another partial section view of a distal portion of a delivery system.

FIG. 23A depicts, for illustration purposes only, the attachment assembly 810 coupled to the intervertebral device 700, the expansion tool 860 being detached from the attachment assembly 810 and the guide assembly 1010 being inserted into the attachment assembly 810 in place thereof. The guide assembly 1010 may be attached or coupled to the attachment assembly 810 in similar fashion as the expansion tool 860 is attached to the attachment assembly 810, as described above. Once the guide assembly 1010 is coupled to the attachment assembly 810, the insertion assembly 1030 may be coupled to the guide assembly 1010, as generally depicted in FIG. 23B. The insertion assembly 1030 may be coupled to the guide assembly 1010 prior to coupling the guide assembly 1010 with the attachment assembly 810, if desired. FIG. 24A depicts the insertion assembly 1030 fully coupled to the guide assembly 1010, the cylindrical distal portion 1036 of the insertion assembly slidably positioned within a portion of the lumen 1018 of the handle portion 1012 of the guide assembly 1010. As depicted in the section view of FIG. 24B, when the insertion assembly 1030 is fully coupled to the guide assembly 1010, a distal end 1040D of the elongate member 1040 may be adjacent to an opening of the intervertebral device 700. Prior to this coupling, the lumen 1022 of the elongate member 1020 of the guide assembly 1010 may be filled with a desired amount of therapeutic agent. For example, a measured amount of the therapeutic agent may be positioned within the lumen 1018 and advanced within lumen 1022 of the elongate member 1020. Insertion or coupling of the insertion assembly 1030 with the guide assembly 1010 may then result in the deployment of a portion of the therapeutic agent within the intervertebral device 700, e.g., within void 702, and out of the various openings of the device 700 and into contact with surrounding biological tissue. The insertion assembly 1030 may be removed from the guide assembly 1010 to allow insertion of additional therapeutic agent material into the lumen 1022 of the elongate member 1020, if desired, the additional material deployed by the plunger assembly 1050 as described immediately above. This process may be repeated as necessary to deploy a desired amount of therapeutic agent within the intervertebral device and surrounding tissue. Turning to FIG. 25A, a sectional view of the attachment assembly 810 is depicted. In this view the plunger control 1052 is depicted in a depressed position, a distal tip 1054D of the elongate shaft 1054 advancing into the intervertebral device 700, e.g., into the void 702. In this way, additional portions of the one or more therapeutic agents positioned within the distal portion of the lumen 1022 of the guide assembly 1010 may be advanced by the distal tip 1054D of the elongate shaft 1054, as generally represented by arrows 1054A in FIG. 25B.

Utilization of the guide assembly 1010 and insertion assembly 1030, in conjunction with the attachment assembly 810, to deploy one or more therapeutic agents to an intervertebral device and surrounding biological tissue is advantageous. Once the intervertebral device is positioned, the expansion tool 860 may be removed and the various structures of the attachment assembly 810 may now be utilized to deploy one or more of the therapeutic agents, as described above. In this way, the attachment assembly 810 may serve multiple functions in operative procedures making such procedures easier to perform, and safer and less costly for the patient.

Figure 26:
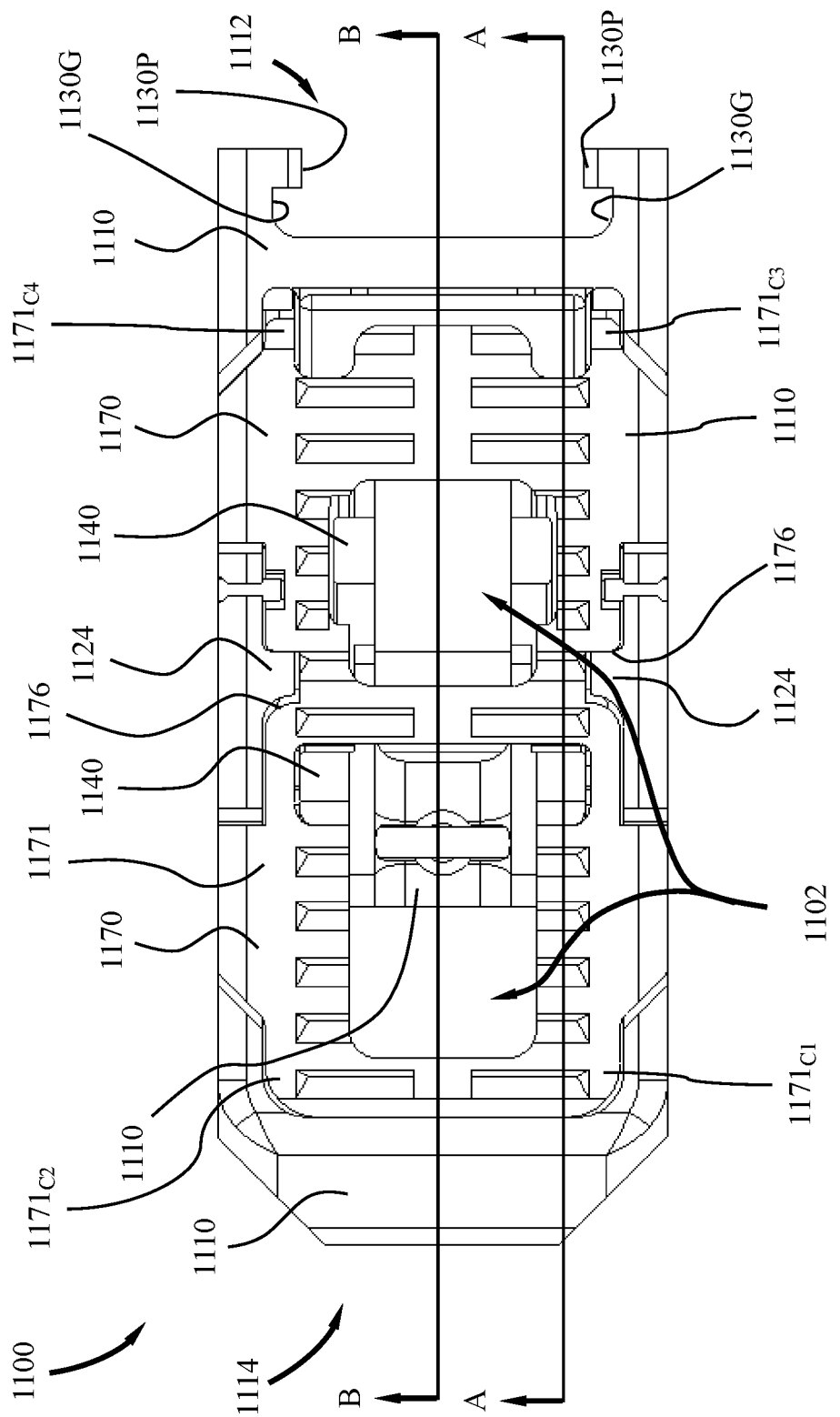

Turning now to FIG. 26, another exemplary intervertebral device 1100 includes a first or base element 1110, a second or sliding element 1140, and a third element 1170. The intervertebral device 1100 is generally similar to other intervertebral devices described or contemplated herein, however, the third element 1170 is adapted to also rotate with respect to the other elements 1110, 1140, in particular, rotate about a line generally perpendicular to a longitudinal access of the intervertebral device 1100. The top surface 1171 may include first, second, third, and forth corner portions $1171_{C1}$, $1171_{C2}$, $1171_{C3}$, $1171_{C4}$, respectively, and $1171_C$ collectively. As discussed in greater detail below, the second element 1140 and the third element 1170 may be adapted such that each of the four corner portions $1171_C$ of the top surface 1171 move at one of a plurality of rates as the second element 1140 translates with respect to the third element 1170. In this way, the third element 1170 may have a top planar surface that rotates, or otherwise is angled, with respect to a bottom planar surface of the base element 1110 as the sliding element 1140 translates from a proximal position to a distal position. Furthermore, as described in greater detail below, a top planar surface of the third element 1170 may be initially angled with respect to a bottom planar surface of the base element 1110, such that when the third element 1170 is elevated, its top planar surface may form a complex angle with respect to a bottom planar surface of the base element 1110. As described with respect to other intervertebral devices, the intervertebral device 1100 includes a proximal end 1112 and a distal end 1114, and the proximal end 1112 may include a structure used for positioning and operating the device 1100, through use of the attachment assembly 810 for example.

Figure 27:
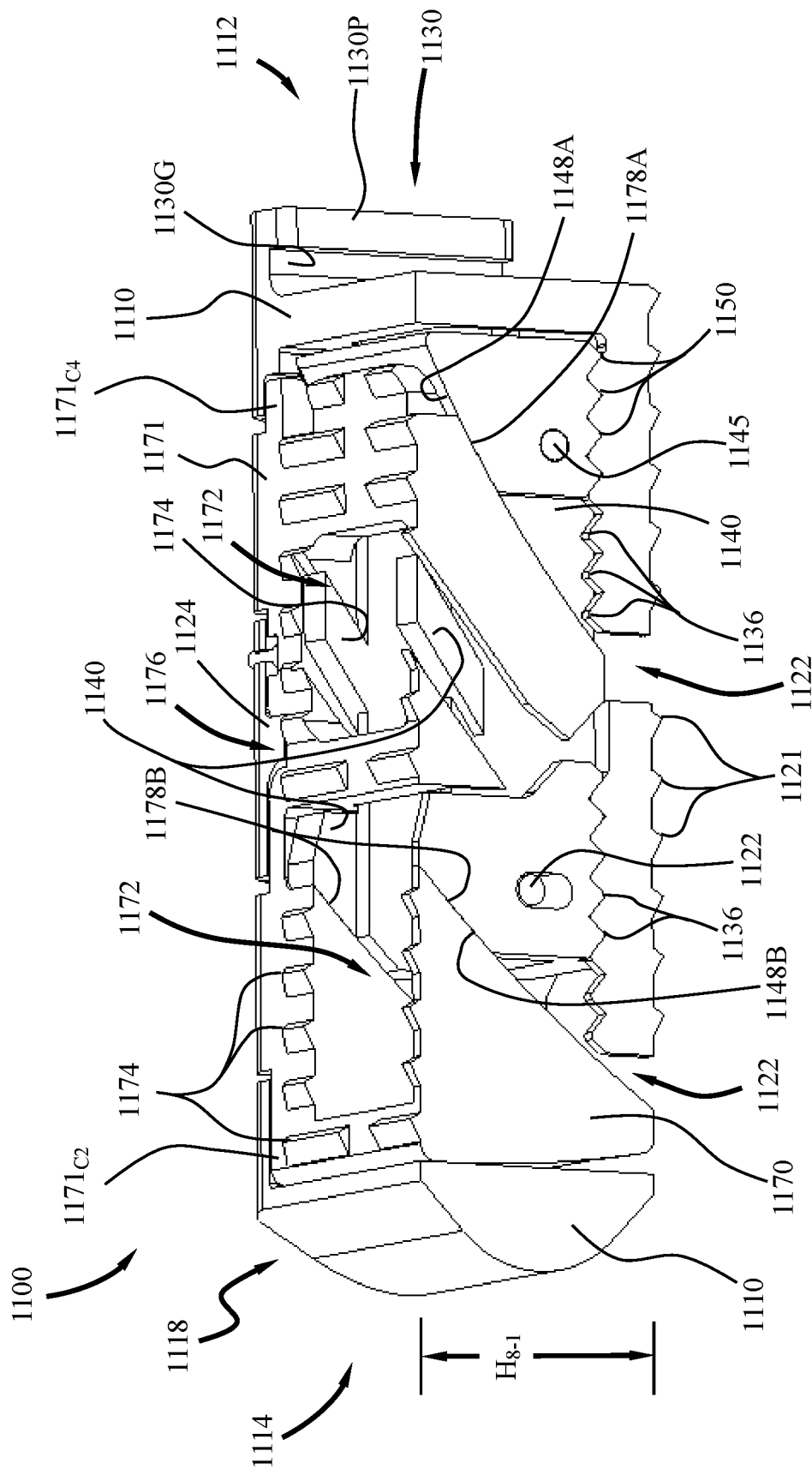
Figure 28:
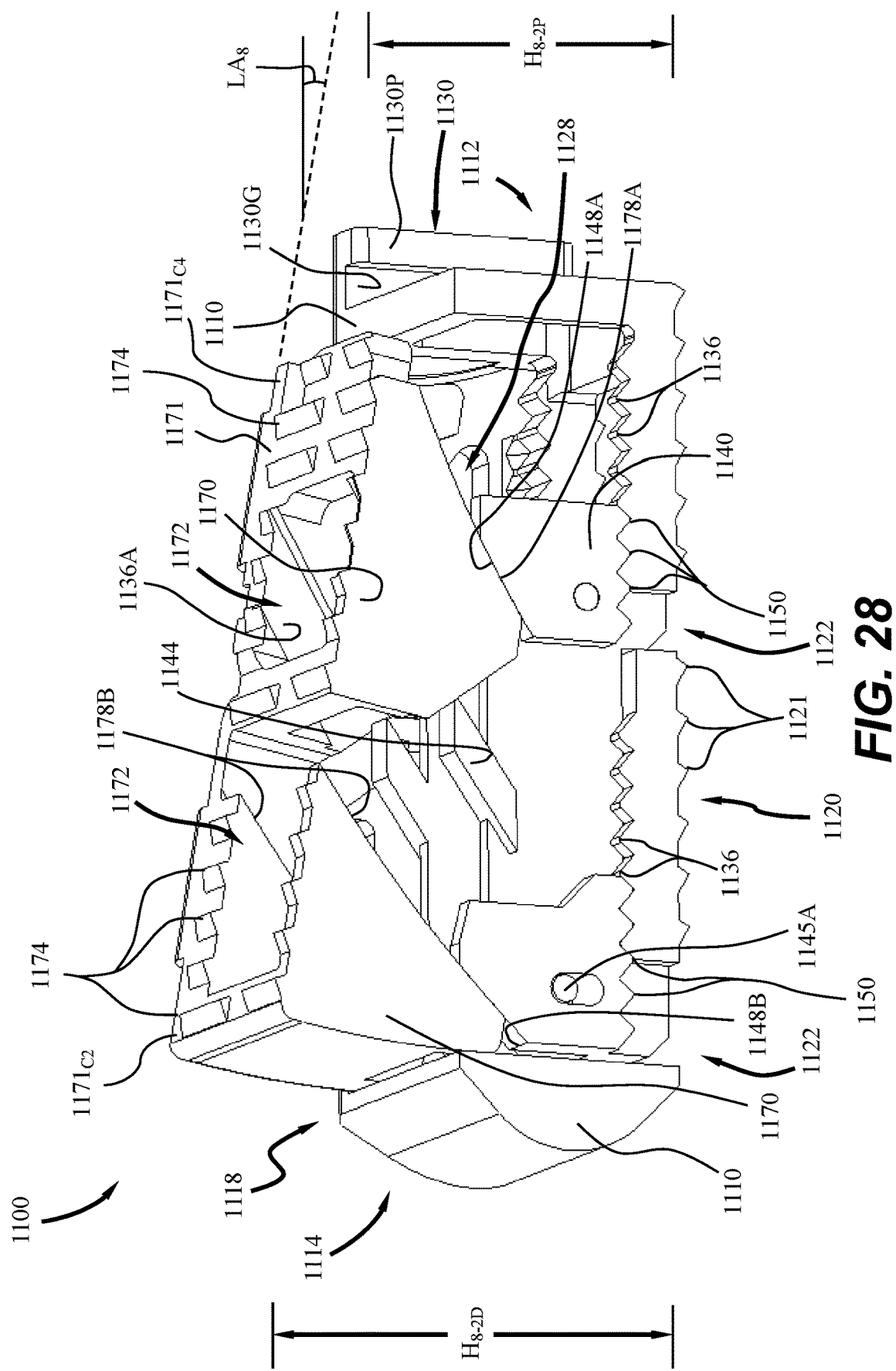

Turning also to FIGS. 27 and 28, in which perspective views of the exemplary intervertebral device 1100 is depicted in cut view along section A-A of FIG. 26. As with other intervertebral devices described or contemplated herein, and better understood in light of the discussion below, the elements 1110, 1140, 1170 cooperate such that the intervertebral device 1100 geometric height, $H_8$, may have a minimum height in a collapsed configuration, as generally depicted in FIG. 27, and a maximum height in an expanded configuration, as generally depicted in FIG. 28.

The first element 1110, also referred to as base 1110 or base element 1110, may be configured to provide a base or outer structure for the intervertebral device 1100, and includes a first end 1112, a second end 1114, and two side portions, a first side portion 1116 (as shown in FIG. 26) and an opposing side portion 1118. A bottom portion 1120 includes one or more openings 1122, allowing for one or more therapeutic agents to pass therethrough, for example. The second and third elements 1140, 1170 may also include similar openings for the same or differing purposes. The proximal end 1112 may include an opening 1130 for passing a portion of one or more tools utilized for delivery of said therapeutic materials, or expanding, contracting, or locking the intervertebral device 1100 in a specific configuration, for example. As with other intervertebral devices described or contemplated herein, utilizing a single connecting point on the device 1100 for interfacing with a tool that can allow for other tools to be easily attached, tools for expanding, contracting or locking the device 1100 in a specific configuration, or tools for delivery of therapeutic materials, provides for a more efficient system, allowing a user to more easily place, position, manipulate, and operate the device 1100.

The intervertebral device 1100 may be expanded or contracted to any suitable height, $H_8$, between a first collapsed height $H_{8-1}$, as depicted in FIG. 27, and second expanded heights $H_{8-2P}$ and $H_{8-2D}$, as depicted in FIG. 28. As described in greater detail below, since the third element 1170 is configured to rotate with respect to the first and second elements 1110, 1140 as the intervertebral device 1100 transitions from a collapsed configuration to an expanded configuration, a distal portion of the third element 1170 may have a second height $H_{8-2D}$ and a proximal portion of the third element 1170 may have a second height $H_{8-2P}$. For example, the intervertebral device 1100 may be expanded from a first position, having a height of $H_{8-1}$ as depicted in FIG. 27, to a second position, having a maximum distal height of $H_{8\text{-}2D}$ and a maximum proximal height of $H_{8\text{-}2P}$ as depicted in FIG. 28, or another position therebetween, and locked in that position.

The proximal end 1112 may also include structures, such as protrusions 1130P and grooves 1130G, which may allow for attachment points to a delivery system (not shown), as described above with respect to delivery device 800 of FIG. 6, for example. Such attachment points may also form the basis for at least initially positioning the intervertebral device 1100, for example between two adjacent vertebrae. As described in greater detail above, the delivery system 800 may include tubular members through which tools to operate the device 1100, i.e., expand or contract the intervertebral device 1100, or deliver one or more therapeutic agents may be introduced, for example, to internal spaces within the intervertebral device 1100 and exiting through the one or more openings 1122 of the element 1110 or one or more openings 1172 of element 1170, or additional similar openings of the elements 1110, 1140, 1170. In this way, such therapeutic agents or materials may contact surrounding tissues, such as bone tissue, encouraging healing. The tubular members to perform these functions may be the same tubular member or different tubular members.

As with other intervertebral devices described or contemplated herein, the third element 1170 may be slidably interfaced to the first and second elements 1110, 1140 such that the third element 1170 at least slides vertically with respect to the first and second elements 1110, 1140. The third element 1170 may include one or more openings 1172 in the top portion or surface 1171 thereof to allow for passage or introduction of therapeutic elements or bone growth enhancing materials therethrough. The top portion 1171 may include one or more protrusions 1174 that may aide in holding the top portion 1171 immobile with respect to adjacent structures or biological tissue, such as vertebrae structures for example. While only a few protrusions 1174 are identified, additional or less protrusions 1174 may be utilized. Such protrusion structures 1174 may be constructed from any biocompatible material and in any suitable form. Additionally, sidewalls 1116, 1118 of element 1110 may include one or more protrusions (not shown), and a bottom portion or surface 1120 of base 1110 may include one or more protrusions 1121. Protrusions 1121 may be, for example, similar to protrusions 1174, which may aide in holding a bottom portion 1120 immobile with respect to adjacent structures or biological tissue, such as vertebral structures for example.

The first element 1110 may include a positioning structure or protrusion 1124, which may be configured or adapted to move within a corresponding channel 1176 to ensure the third element 1170 moves in a specific direction with respect to the base element 1110. In this case, the protrusion 1124 and corresponding channel 1176 may be curvilinear to allow for rotation of the third element 1170 with respect to the second element 1140 as the second element 1140 translates.

As with other intervertebral devices described or contemplated herein, a void or space 1102 is defined by the first, second, and third elements 1110, 1140, 1170 of the intervertebral device 1100, the void 1102 increasing as the device 1100 transitions from a collapsed configuration to an expanded configuration. In this way, once the device 1100 is deployed, one or more therapeutic agents may be positioned within the void 1102. As described above, such therapeutic agents may further flow out of the void 1102 via additional openings, such as openings 1172 and 1122, positioned about the elements 1110, 1140, 1170.

In operation, the third element 1170 of intervertebral device 1100 at least rotates with respect to the first and second elements 1110, 1140. As with other intervertebral devices described or contemplated herein, the intervertebral device 1100 utilizes interfacing, interacting or mating surfaces between the second and third elements 1140, 1170, however the surfaces of the intervertebral device 1100 may be curvilinear to encourage at least rotational movement of the third element 1170 with respect to the first and second elements 1110, 1140. Such curvilinear surfaces may allow for portions of the third element 1170 to move at different rates with respect to other portions thereof, while maintaining constant or near constant surface contact between the curvilinear surfaces of the third element 1170 and the second element 1140. More specifically, the third element 1170 may include a plurality of curvilinear surfaces 1178 that are configured or adapted to come in contact along a respective one of a plurality of curvilinear surfaces 1148 of second element 1140. Curvilinear surfaces 1178 may include a first pair of curvilinear surfaces 1178A and a second par of curvilinear surfaces 1178B and these curvilinear surfaces may interface with corresponding curvilinear surfaces 1148A, 1148B of the second element 1140, respectively. Accordingly, as the second element or sliding element 1140 translates between the first end 1112 and the second end 1114 of the base element 1110, the curvilinear surfaces 1148 of the second element 1140 contact and slide along corresponding respective curvilinear surfaces 1178 of the third element 1170 resulting in movement of the element 1170 in at least a vertical direction.

For purposes herein, the term "curvilinear surfaces" includes surfaces of any length down to a point surface. Accordingly, and for illustration purposes only, one or more of the curvilinear surfaces 1148 of the sliding element 1140 may be point surfaces, or otherwise surfaces having dimensions that minimalize into a point contact, that contact and interact with a respective one of the curvilinear surfaces 1178 of the third element 1170. Alternatively, one or more of the curvilinear surfaces 1178 may be point surfaces, or otherwise surfaces having dimensions that minimalize into a point contact, that contact and interact with a respective one of the curvilinear surfaces 1148 of the sliding element 1140. It should be noted that increase contact surface area between the curvilinear surfaces 1148, 1178 may lead to increased strength.

As depicted, translation of sliding element 1140 from the first end 1112 toward the second end 1114 results in movement of the element 1170 in at least a vertical direction away from the base element 1110, the third element 1170 rotating with respect to the first and second elements 1110, 1140. Translation of the sliding element 1140 in a direction from the second end 1114 toward the first end 1112 results in movement of the element 1170 in at least a vertical direction toward the base element 1110, the third element 1170 once again rotating with respect to the first and second elements 1110, 1140, the top surface 1171 of the third element 1170 being substantially parallel with the bottom surface 1120 of the first element 1110 when the device 1100 returns to its collapsed configuration.

Curvilinear surfaces 1148A of the second element 1140 and curvilinear surfaces 1178A of the third element 1170 may define a first circle having a radius R1 (not shown), while curvilinear surface 1148B of the second element and curvilinear surface 1178B of the third element 1170 may define a second circle having a radius R2 (not shown), which is greater than the radius R1. First and second circles are concentric allowing for all interfacing surfaces to be in intimate contact during activation. As the second element 1140 moves distally, differences in radii R1 and R2 result in portions of the third element 1170 moving vertically at differing rates. For example, corner portions $1171_{C1}$ and $1171_{C2}$ of the third element 1170 may move vertically at a faster rate than corner portions $1171_{C3}$ and $1171_{C4}$ of the third element 1170, resulting in at least rotational movement of the third element 1170 with respect to the first and second elements 1110, 1140. As shown in FIG. 28, when the second element 1140 is in its most distal position, a maximum height of the third element 1170 is $H_{8-2D}$ and a minimum height of the third element 1170 is $H_{8-2P}$, the top surface 1171 of the third element 1170 forming an angle $LA_8$ with respect to a bottom surface of the base element 1110. For illustration purposes only, the height $H_{8-2D}$ may have a maximum of 12 mm, and the height $H_{8-2P}$ may have a maximum range from between 7 mm to about 12 mm, depending on the desired angle $LA_8$, which may range from between about 0° to about 15°. As should be understood by one of ordinary skill in the art, the radii R1 and R2 may be selected to provide for larger or smaller rates of rotation of the third element 1170 with respect to the first element 1110.

As with other intervertebral devices described or contemplated herein, the first element or base element 1110 may include a plurality of engaging elements 1136 that protrude from a top inner surface of the bottom portion 1120 of element 1110. Second element 1140 may include a plurality of engaging elements 1150, at least one of the elements 1150 engaging a respective one of the plurality of engaging elements 1136. While depicted as being integral to the respective elements 1110, 1140, the engaging elements 1136, 1150 may be individual parts attached or affixed to the surfaces of the base element 1110 and sliding element 1140, respectively. As with the engaging elements 736, 750 of the intervertebral device 700, the engaging elements 1136, 1150 are depicted as having similar shapes, e.g., triangular portions, however in other configurations, the shapes can be dissimilar, or may be nonsymmetrical along its vertical central axis, passing through the tip of each element 1136, 1150.

As with intervertebral device 700, the intervertebral device 1100 may be configured such that applying a linear force to the sliding element 1140 to translate the element 1140 between the first and second ends 1112, 1114 of base member 1110, results in each engaging element 1150 sliding up and over a corresponding engaging element 1136, and engaging an adjacent engaging element 1136 in the direction of the movement of sliding element 1140. Accordingly, sliding element 1140, while primarily moving along the longitudinal axis of the base element 1110, may also move vertically in accordance with the geometry outline and coupling of the engaging elements 1150, 1136 of the sliding element 1140 and base element 1110, respectively.

The intervertebral device 1100 may further include a plurality of pins 1145 coupled to sliding member 1140 and extending through corresponding openings 1128 in the side portions 1116, 1118 of base element 1110, the openings 1128 may be similar to openings 728 of the intervertebral device 700. With the intervertebral device 1100 in the collapsed configuration, as depicted in FIG. 27, the sliding element 1140 is nearer the first end 1112, the pins 1145 being nearer the first end 1112, as well. With the intervertebral device 1100 in the expanded configuration, as depicted in FIG. 28, the sliding element 1140 is nearer the distal end or second end 1114, the pins 1145 being nearer the second end 1114, as well. The openings 1128 of the first element 1110 may be spaced to allow some vertical travel of the sliding element 1140 and pins 1145 in accordance with the geometrical shapes, e.g. height, of the engaging elements 1150, 1136. It is noted that by adjusting the slope or curvilinear shape of each side surface of the engaging elements 1150, 1136 the translational force to move the sliding element 1140 in the presence of a compression force between the top surface 1171 of element 1170 and the bottom portion 1120 of the base element 1110 may differ in accordance with the corresponding element 1150, 1136 shaped surfaces. The geometric shape of each side surface of the engaging elements 1150, 1136, which may be linear or curvilinear, or a combination thereof, may be configured to encourage movement of the sliding element 1140 in a first direction along the longitudinal axis of the base 1110 with respect to movement of the sliding element 1140 in a second opposite direction. In any case, the engaging elements 1150, 1136 are configured, e.g., with suitable shaped surfaces or the like, to become locked or immovable when a compression force exists between the third element 1170 and the base element 1110.

Turning specifically to FIG. 28, the sliding element 1140 may include a protrusion 1144 configured or adapted to slidably interface with a corresponding recessed portion or groove 1136A, 1138A (not shown) of the third element 1170. The protrusion 1144 may cooperate with recessed portion 1136A such that when the sliding element 1140 translates in a distal direction, in a direction toward distal end 1114 of the intervertebral device for example, one or more surfaces of the protrusion 1144 may engage corresponding one or more surfaces of the recessed portion 1136A to encourage the third element 1170 to move vertically and rotationally away from the first element 1110. Additionally, the protrusion 1144 may cooperate with the recessed portion 1136A such that when the sliding element 1140 translates in a proximal direction, in a direction toward the proximal end 1112 of the intervertebral device 1110 for example, one or surfaces of the protrusion 1144 may engage corresponding one or more surfaces of the recessed portion 1136A to encourage the third element 1170 to move vertically and rotationally toward the first element 1110.

As with vertebral device 700, in the presence of a linear force applied to sliding element 1140 moving the element 1140 toward the distal end 1114, in a ratcheting manner, for example, the engaging elements 1150, 1136 continuously engage and disengage with adjacent opposing engaging elements 1150, 1136. As the element 1140 translates, the third element 1170 moves vertically to increase the overall height, $H_8$, of the device 1100. With a compression force applied between the third element 1170 and the base element 1110, e.g. when the device 1100 is positioned between adjacent tissue surfaces, such as two adjacent vertebrae, the engaging elements 1150, 1136 of the sliding element 1140 and base element 1110, respectively, engage and prevent the sliding element 1140 from further translating. For illustration purposes only, the sliding element 1140 of the intervertebral device 1100 may be translated through the use of a tool, such as expansion tool 860 described above for example, the distal portion of the sliding element 1140 including protrusions 1140P and grooves 1140G, as best viewed in FIGS. 29 and 30 discussed immediately below, to interface with the expansion tool 860, for example.

Figure 29:
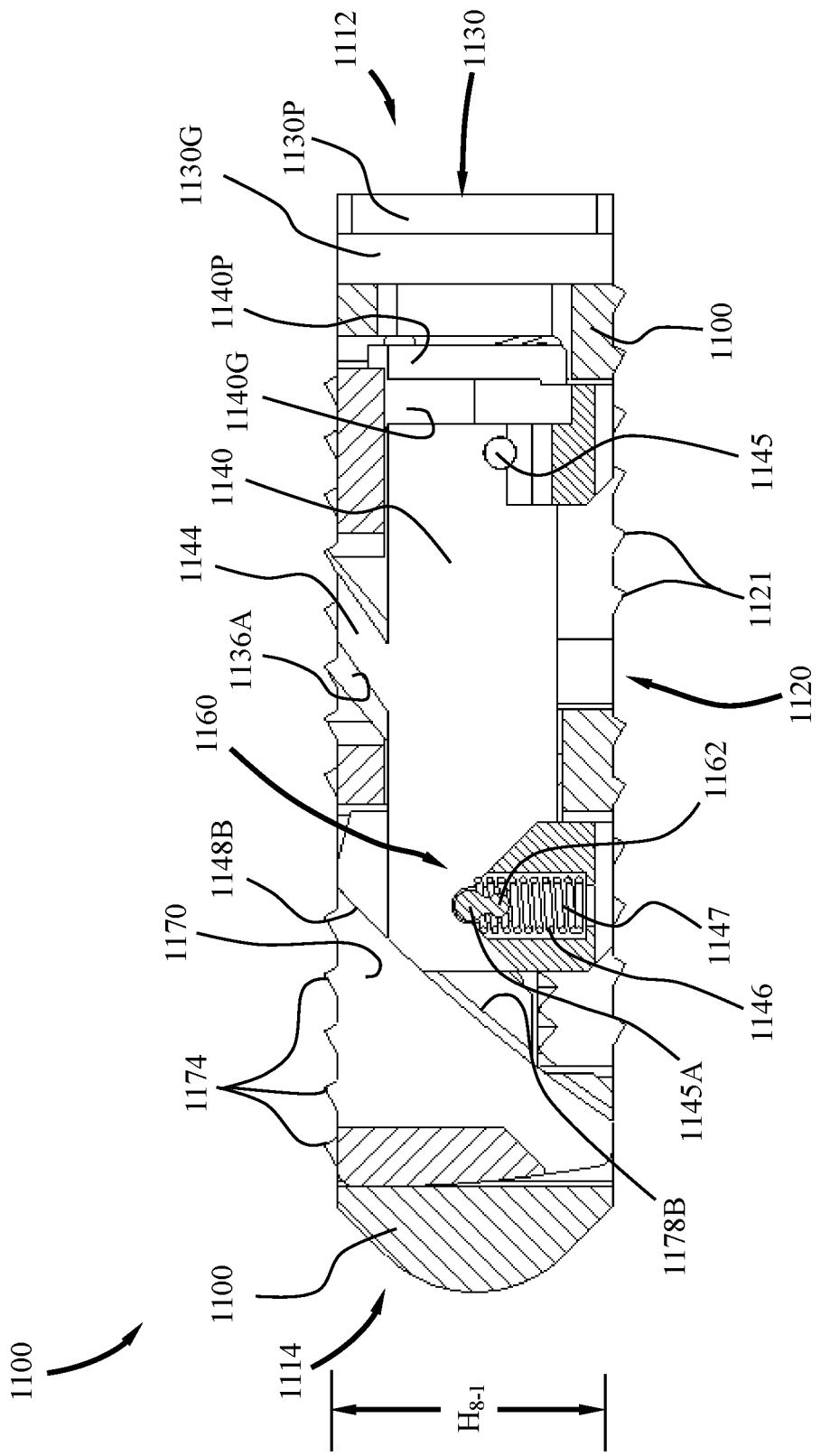
Figure 30:
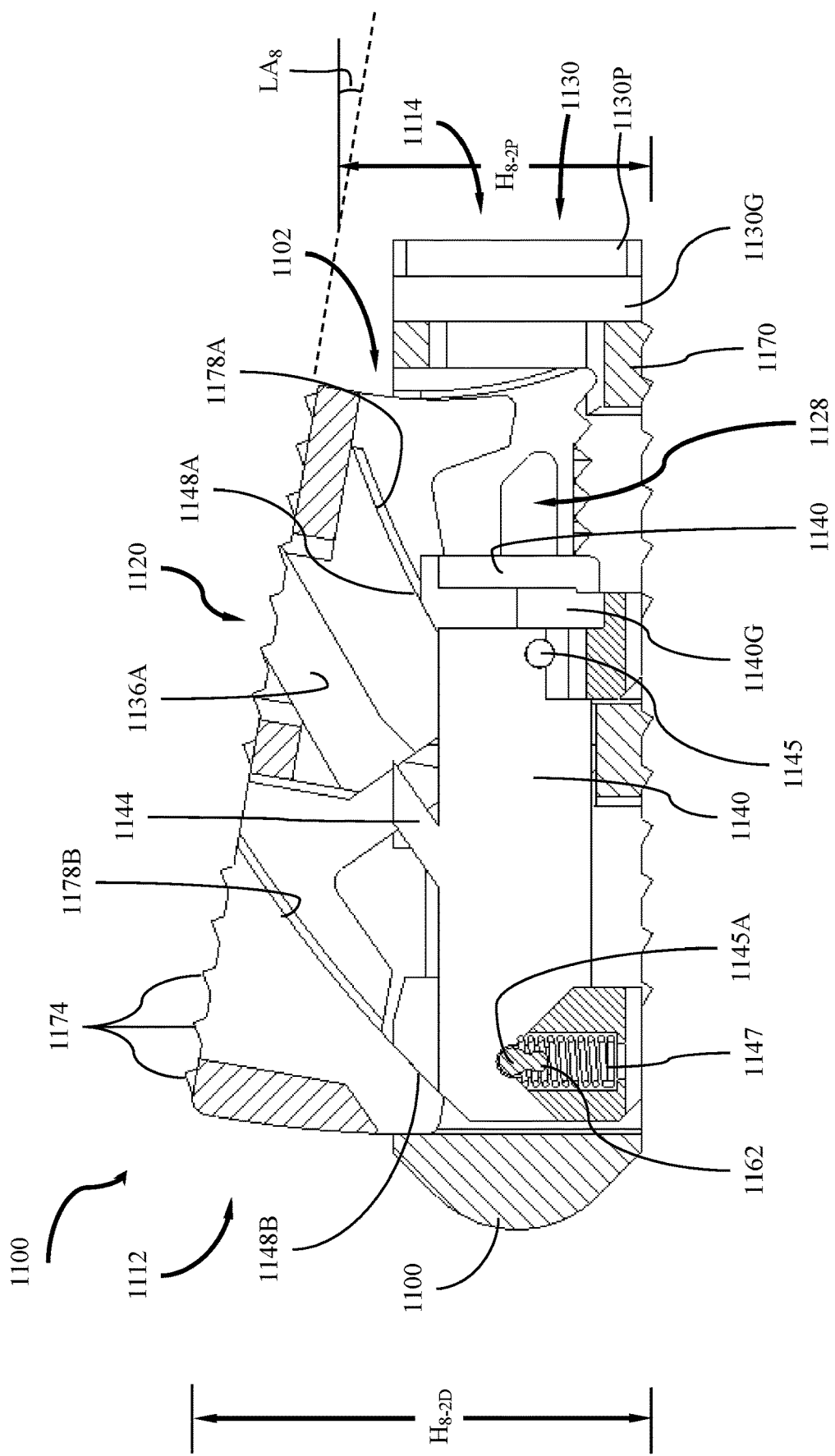

Turning to FIGS. 29 and 30, the intervertebral device 1100 is depicted in an elevation via cross-section along section B-B of FIG. 26. The intervertebral device 1100 is depicted in a collapsed configuration in FIG. 29 and in an expanded configuration in FIG. 30. In particular, the sliding element 1140 may include a retention device 1160 to aide in maintaining contact between the engaging elements 1150, 1136 of the sliding element 1140, as better viewed with respect to FIGS. 27 and 28, and base element 1110, respectively. The retention device 1160 may include a pin 1145A and a spring 1147, both depicted in cross section, the spring 1147 seated in a bore 1146 of the second element 1140. The pin 1145A may extend from a first opening 1123 in side portion 1116 (not shown) of the base element 1100 to a second opening 1123 in side portion 1118 (not shown) of the base element 1100. The pin 1145A may include a central protrusion 1162 that extends from a central longitudinal axis of the pin 1145A toward the bottom 1120 of the first element 1110 within the spring 1147, retaining the pine 1145A to the spring 1147.

In operation, as the sliding element 1140 translates between the two ends 1112, 1114, the engaging elements 1150, 1136 repeatedly engage and disengage resulting in the sliding element 1140 repeatedly moving vertically away from, and toward to, the bottom portion 1120 of the base element 1110. As the sliding element 1140 moves away from the base element 1110 the ends of the pin 1145A may engage the top surfaces of the corresponding openings 1123 in respective side portions 1116, 1118, acting to compress the spring 1147. As the engaging elements 1150 of the sliding element 1140 pass over the corresponding engaging elements 1136 of the base element 1110 the spring 1147 imparts a force upon the sliding element 1140 to encourage re-engagement of the adjacent engaging elements 1150, 1136. In this way, the engaging elements 1150 are biased to remain coupled to corresponding engaging elements 1136 during movement of the sliding element 1140, particularly in a no-load situation, where the force between the third element 1170 and the first element 1110 is minimal, for example. Accordingly, when a compression force is applied between the top surface 1171 of the third element 1170 and the bottom surface 1120 of the base element 1110, engaging elements 1150, 1136 maintain the current position of all three elements 1110, 1140, 1170 and, ultimately, a current distal height, $H_{8-D}$, and a current proximal height, $H_{8-P}$, of the intervertebral device 1100.

It may be desirable to provide intervertebral devices described or contemplated herein, including intervertebral device 1100, for example, with angular top surfaces to better engage surrounding biological tissues, such as adjacent vertebral structures. Such angular top surfaces can allow for such engagement of surrounding biological tissues when positioned with differing methods, including TLIF and PLIF approaches, or other approaches known in the art. Turning to FIGS. 31A and 31B, an alternative intervertebral device 1100A is depicted in a first collapsed configuration. The alternative intervertebral device 1100A is similar to device 1100, including a first element 1110 and a second element 1140, however the intervertebral device 1100A may include a third element 1170A in place of third element 1170. The third element 1170A may be similar to third element 1170 except the third element 1170A may include a top surface 1171 that forms an angle 1171A along its longitudinal axis with respect to a top surface of the first element 1110, as generally depicted. FIG. 31A depicts the intervertebral device 1100A from its proximal end 1112, while FIG. 31B depicts the intervertebral device 1100A from its distal end 1114. FIG. 31A further depicts void 1102 defined by the first, second and third elements 1100, 1140, 1170 and a pair of recesses 1132 that may encourage attachment to a delivery tool, as described in greater detail above.

Figure 32B:
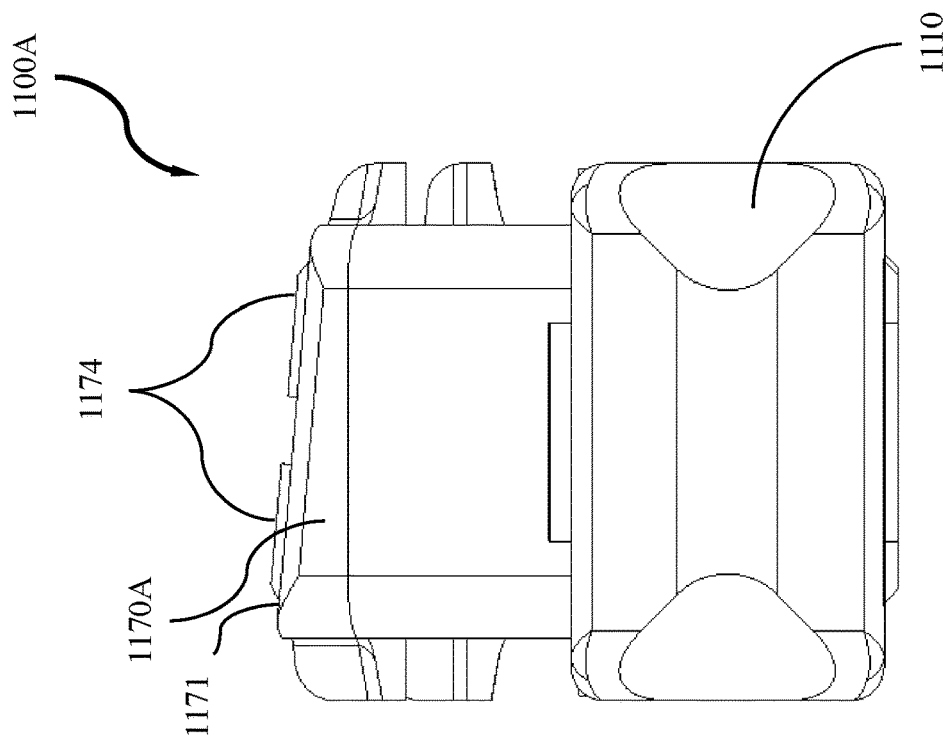
FIGS. 32A and 32B are additional end views of the exemplary intervertebral device of FIGS. 31A and 31B, respectively.
Figure 32A:
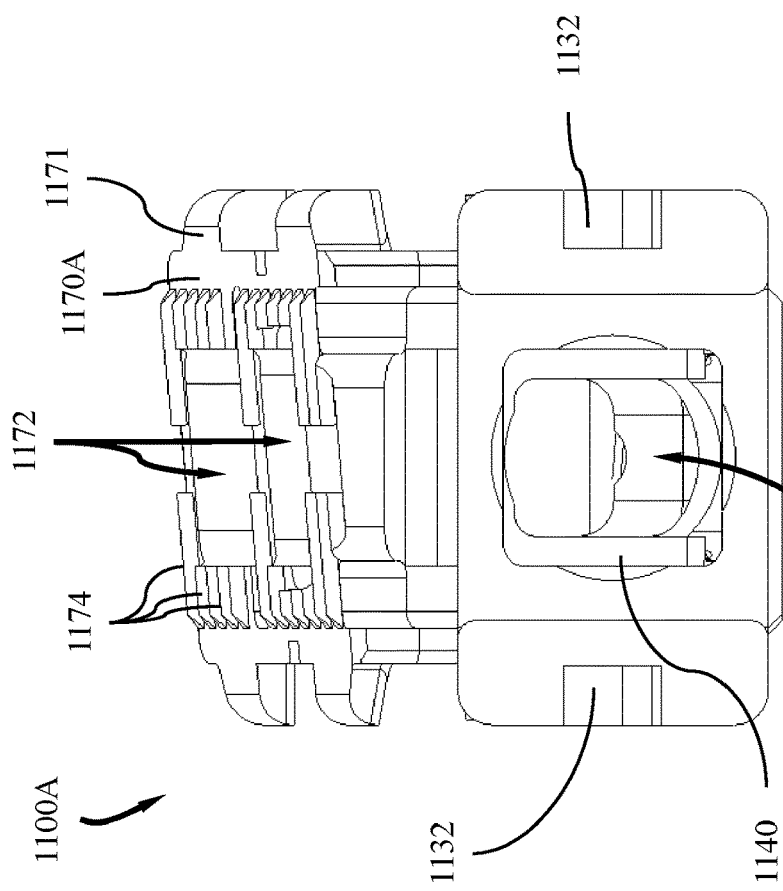

FIGS. 32A and 32B depict the intervertebral device 1100A in its expanded configuration. As shown, since the third element 1170A includes an angled top surface 1171 and the third element 1170A rotates with respect to the second element 1140 as the device 1100A expands, the top surface 1171 of the third element 1170A takes on a planar surface that is angled with respect to both a longitudinal axis and a lateral axis of the intervertebral device 1100A, the angle offset along the longitudinal axis being the angle $LA_8$ as better viewed in FIG. 30, and the angle offset along the lateral axis being the angle 1171A as best viewed in FIGS. 31A-31B.

Figure 33B:
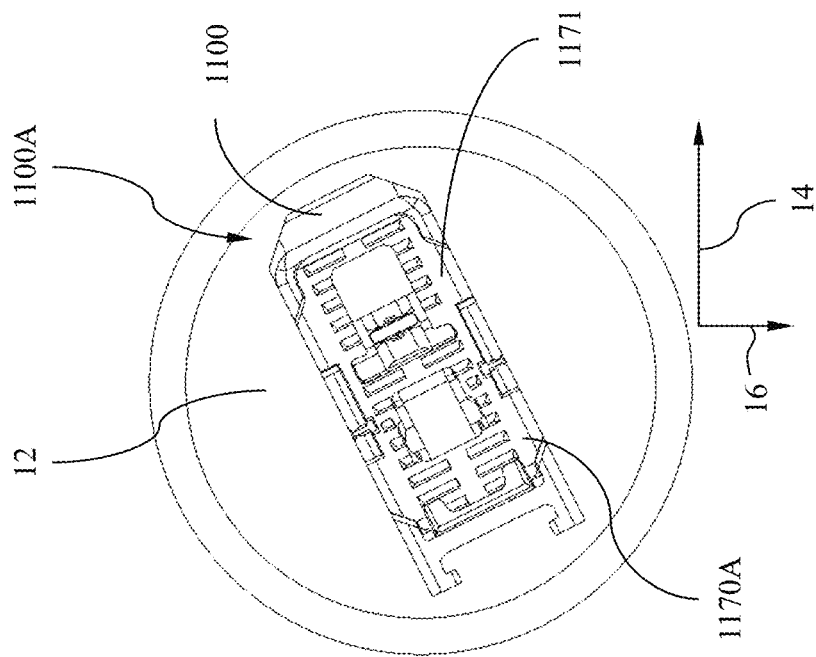
FIG. 33B is a top view of an exemplary placement of an intervertebral device.
Figure 33A:
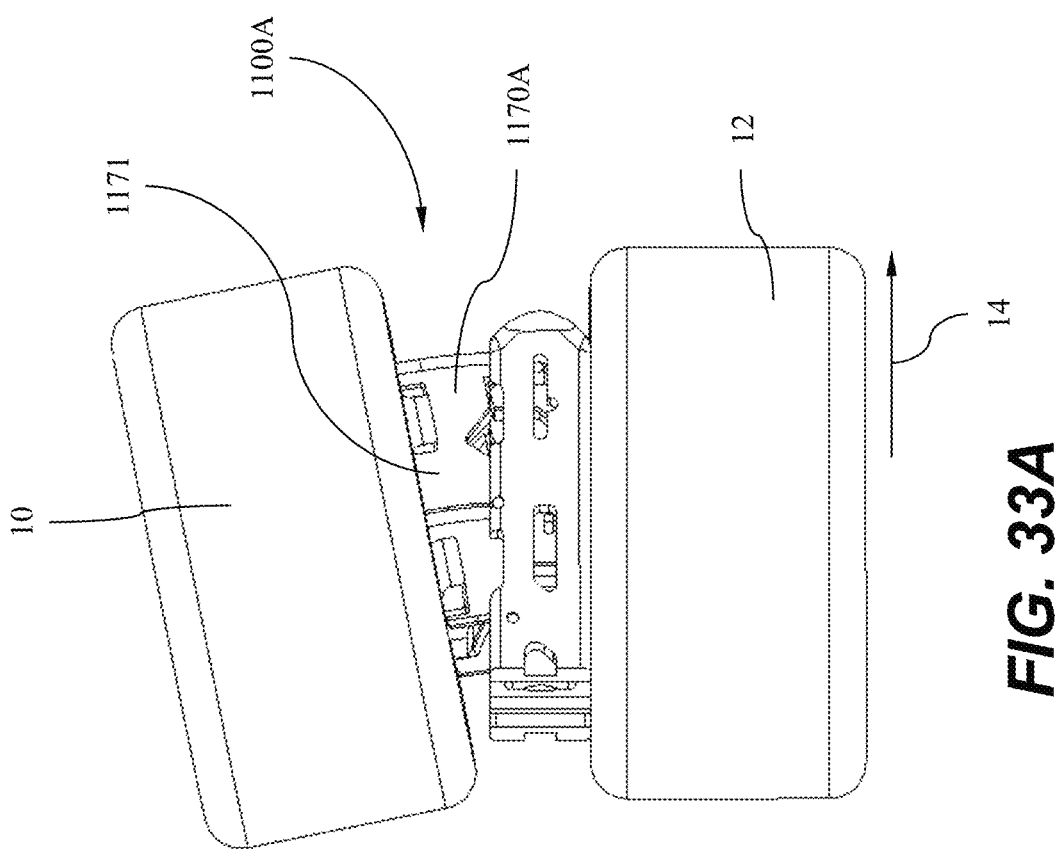
FIG. 33A is a lateral view of an exemplary placement of an intervertebral device.

Turning to FIGS. 33A and 33B, for illustration purposes only, an intervertebral device 1100A is depicted in its expanded configuration between adjacent vertebral bodies 10, 12. As shown, a longitudinal axis of the intervertebral device 1100A is not parallel to either an anterior axis 14 or a lateral axis 16 of the vertebral bodies 10, 12. The angles $LA_8$ and 1171A cooperate to provide a desirable planar top surface 1171 of third element 1170A to anatomically match the natural angular differences between the adjacent vertebral bodies 10, 12. It should be noted that these angles, $LA_8$ and 1171A, may be further manipulated to provide for any approach with respect to adjacent vertebral structures, the angles compensating for any naturally occurring angular offsets therebetween. In this way, the top and bottom surfaces of the intervertebral device 1100A may make better contract with adjacent vertebral bodies, which may allow for stronger bonds between the intervertebral device 1100A and the adjacent vertebral bodies. While depicted and described with respect to certain characteristics of the intervertebral device 1100A, angles $LA_8$ and 1171A may be oriented differently to allow for differing approaches.

Figure 34:
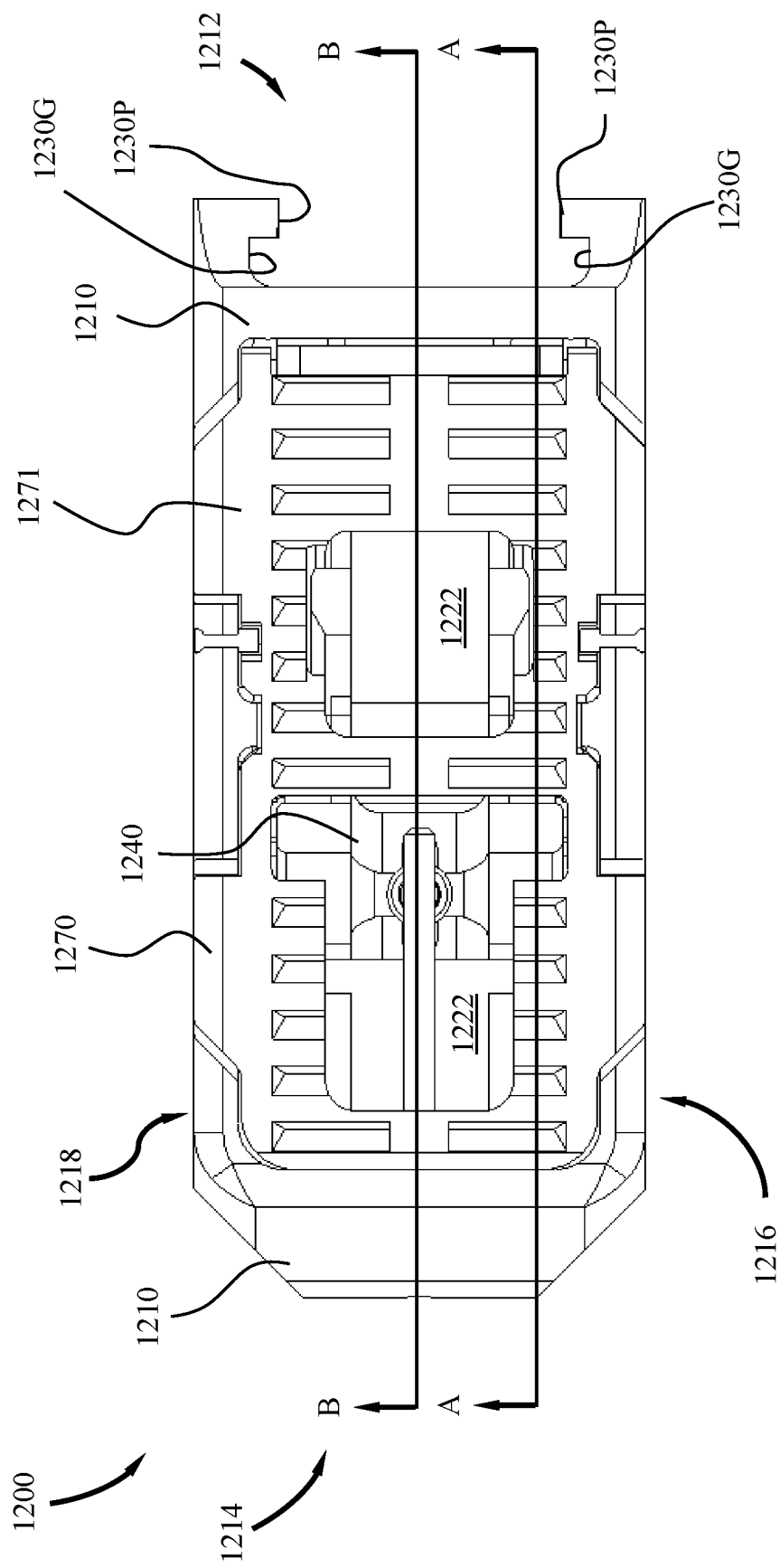

Turning now to FIG. 34, another exemplary intervertebral device 1200 includes a first or base element 1210, a second or sliding element 1240, and a third element 1270. The intervertebral device 1200 is generally similar to intervertebral device 1100, however, the third element 1270 is adapted to move rotationally and linearly with respect to the other elements 1210, 1240. In this way, the third element 1270 may have a top planar surface 1271 that is angled with respect to a bottom planar surface 1220 of the base element 1210, the angled surface being able to further move vertically with respect to the base element 1210 to increase the overall height of the intervertebral device 1200. Furthermore, as described in greater detail above with respect to intervertebral device 1100A, a top planar surface of the third element 1270 may be initially angled with respect to a bottom planar surface of the base element 1210, such that when the third element 1270 is at least elevated, its top planar surface may form a complex angle with respect to a bottom planar surface of the base element 1210. The intervertebral device 1200 includes a proximal end 1212 and a distal end 1214, the proximal end 1212 including geometric structures 1230G, 1230P used for positioning the intervertebral device 1200, as described in greater detail above with respect to other embodiments.

Figure 35:
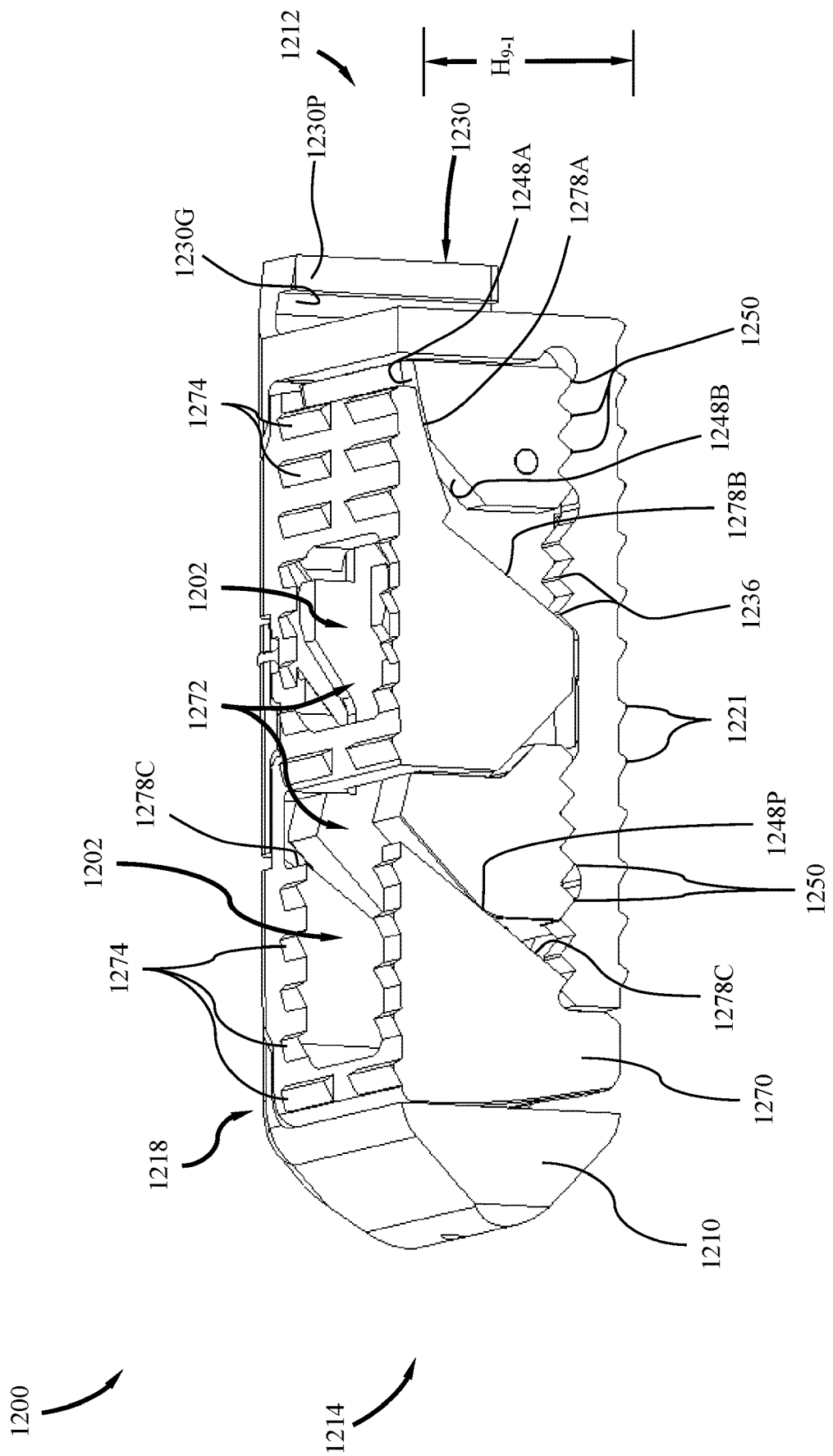
Figure 36:
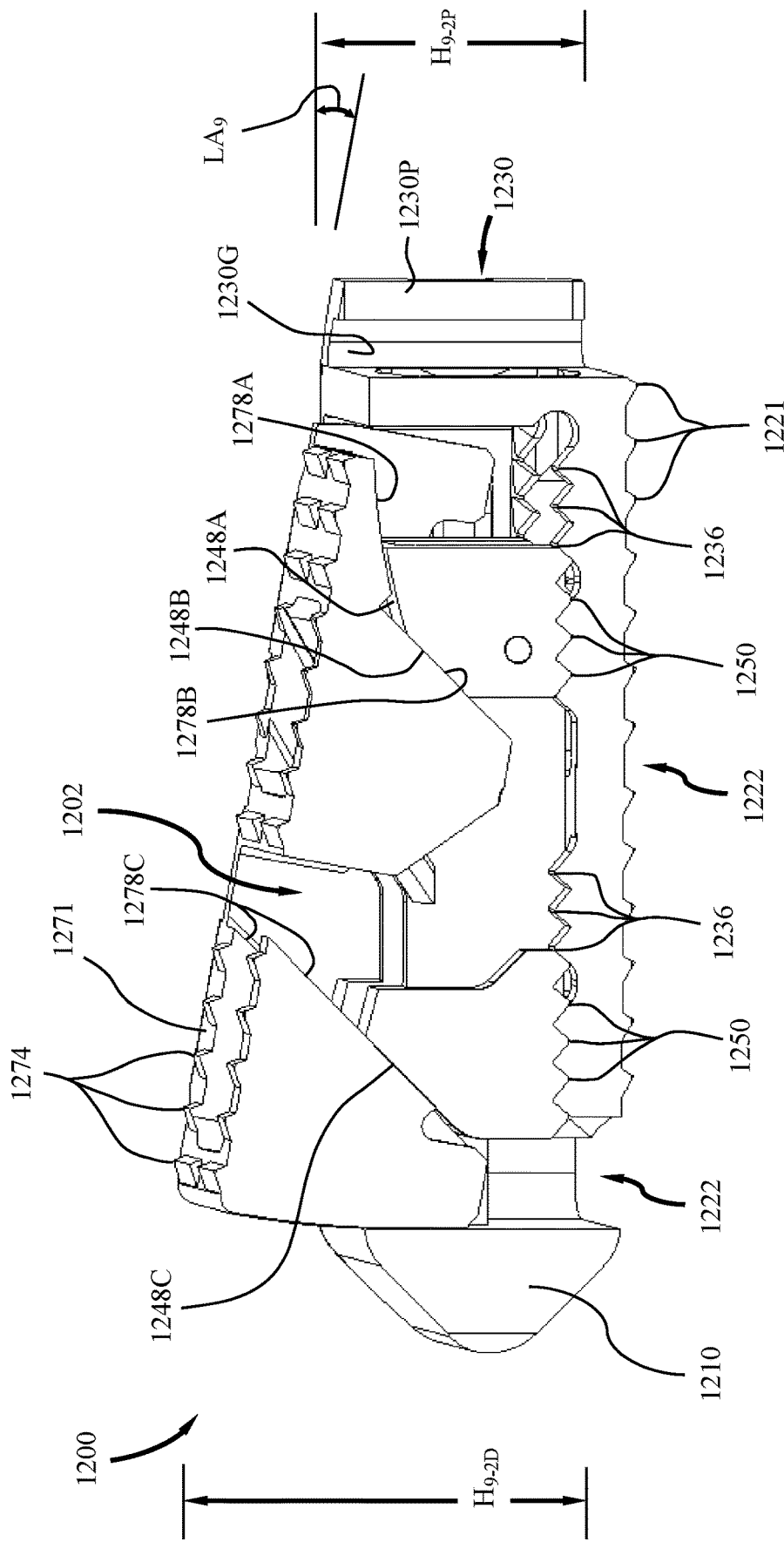
Figure 37:
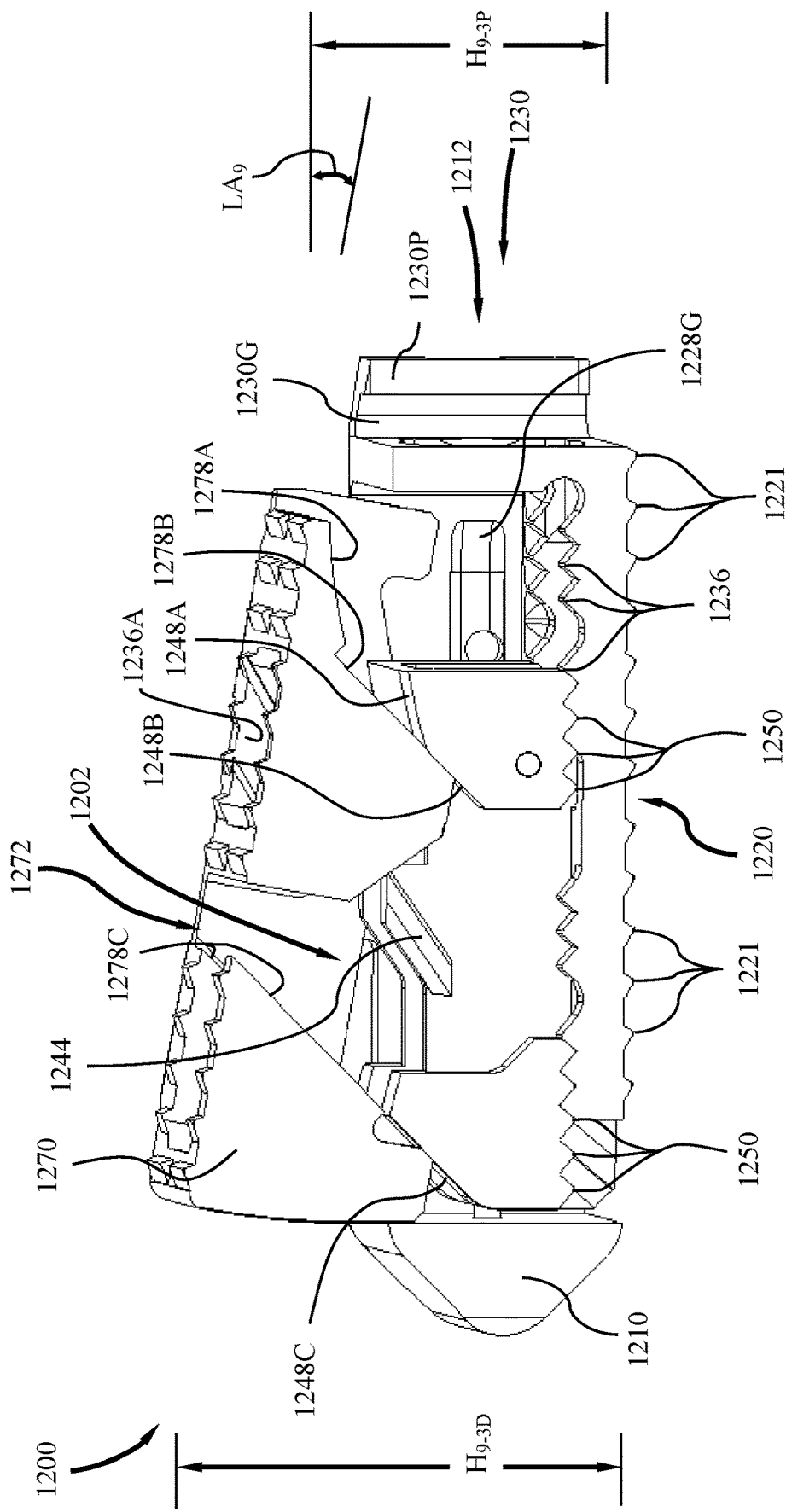

Turning also to FIGS. 35, 36, and 37, a perspective view of the exemplary intervertebral device 1200 is depicted in cut view along section A-A of FIG. 34. As with other intervertebral devices described or contemplated herein and better understood in light of the discussion below, the elements 1210, 1240, 1270 cooperate such that the intervertebral device 1200 geometric height, $H_9$, may have a minimum value when the device 1200 is in a collapsed configuration, as generally depicted in FIG. 35, an intermediate value when the device 1200 is in an intermediate configuration, one example of which is generally depicts in FIG. 36, and a maximum when the device 1200 is in an expanded configuration, as generally depicted in FIG. 37, and discussed in greater detail below.

The first element 1210, also referred to as base 1210 or base element 1210, may be configured to provide a base or outer structure for the intervertebral device 1200, and includes first end 1212, second end 1214, and two side portions, a first side portion 1216 (not shown) and an opposing side portion 1218. A bottom portion 1220 includes one or more openings 1222 allowing for one or more therapeutic agents to pass therethrough, for example. It should be readily understood that the second and third elements 1240, 1270 may also include similar openings for the same or differing purposes. The proximal end 1212 may include an opening 1230 for passing a portion of one or more tools utilized for delivery of said therapeutic materials, or expanding, contracting, or locking the intervertebral device 1200 in a specific configuration, for example. Such one or more tools may include delivery system 800 and the delivery tool 1000.

The intervertebral device 1200 may be expanded or contracted to any suitable height, $H_9$, between a first collapsed height $H_{9-1}$, as depicted in FIG. 35, second expanded heights $H_{9-2P}$ and $H_{9-2D}$, as depicted generally in FIG. 36, and third expanded heights $H_{9-3P}$ and $H_{9-3D}$, as depicted in FIG. 37. As described in greater detail below, since the third element 1270 is configured to rotate and linearly move with respect to the first and second elements 1210, 1240, when the intervertebral device 1200 is in an expanded configuration, a distal portion of the third element 1270 may have a first height $H_{9-3D}$ and a proximal portion of the third element 1270 may have a second height $H_{9-3P}$. For example, the intervertebral device 1200 may be at least rotationally expanded from a first position, having the height of $H_{9-1}$ as depicted in FIG. 35, to a second position, having a distal height of $H_{9-2D}$ and a proximal height of $H_{9-2P}$ as depicted in FIG. 36, and then linearly expanded to a third position, having a distal height of $H_{9-3D}$ and a proximal height of $H_{9-3P}$ as depicted in FIG. 37, or another position therebetween, and locked in that position.

The proximal end 1212 of the intervertebral device 1200 may also include structures, such as protrusions 1230P and grooves 1230G, which may allow for attachment points to a delivery system (not shown), as described above with respect to delivery device 800 of FIG. 6, for example. Such attachment points may also form the basis for at least initially positioning the intervertebral device 1200, for example between two adjacent vertebrae, through an approach described or contemplated herein, or otherwise known in the art. As described in greater detail above, the delivery system 800 may include tubular members through which therapeutic agents may be introduced, for example, to internal spaces within the intervertebral device 1200 and exiting through the one or more openings 1222 of the element 1210 or one or more openings 1272 of the element 1270, or other similar openings of the elements 1210, 1240, 1270. In this way, such therapeutic agents or materials may contact surrounding tissues, such as bone tissue, encouraging healing.

As with other intervertebral devices described or contemplated herein, the third element 1270 may be slidably interfaced to the first and second elements 1210, 1240 such that the third element 1270 at least rotates and/or slides vertically with respect to the first and second elements 1210, 1240. The top portion 1271 may include one or more protrusions 1274 that may aide in holding the top surface 1271 immobile with respect to adjacent structures or biological tissue, such as vertebral structures for example.

While only a few protrusions 1274 are identified, additional or less protrusions 1274 may be utilized. Such protrusion structures 1274 may be constructed from any biocompatible material and in any suitable form and may be applied to any embodiment described or contemplated herein. Additionally, sidewalls 1216, 1218 of element 1210 may include one or more protrusions (not shown), and a bottom portion 1220 of base 1210 may include one or more protrusions 1221. Protrusions 1221 may be, for example, similar to or different from protrusions 1274, and may aide in holding a bottom portion 1220 immobile with respect to adjacent structures or biological tissue, such as vertebral structures.

The element 1210 may include a positioning structure or protrusion 1224, which may be configured or adapted to move within a corresponding channel 1276A to ensure that the element 1270 moves in a specific manner with respect to the base element 1210.

As with other intervertebral devices described or contemplated herein, a void or space 1202 is defined by the first, second, and third elements 1210, 1240, 1270 of the intervertebral device 1200, the void increasing as the device 1200 transitions from a collapsed configuration to an expanded configuration. In this way, once the device 1200 is deployed, one or more therapeutic agents may be positioned within the void 1202, via the delivery system 800 of FIG. 6, for example. Such therapeutic agents may further flow out of the open space via additional openings, such as openings 1272 and 1222, or other openings positioned about the elements 1210, 1240, 1270.

The third element 1270 of intervertebral device 1200 at least rotates and moves linearly with respect to the first and second elements 1210, 1240. As with other intervertebral devices described or contemplated herein, the intervertebral device 1200 utilizes interfacing, interacting or mating surfaces between the second and third elements 1240, 1270, however the surfaces of the intervertebral device 1200 may include both curvilinear and linear portions to encourage at least rotational movement and linear movement of the third element 1270 with respect to the first and second elements 1210, 1240. Such curvilinear and linear surfaces may allow for various portions of the third element 1270 to move at different rates with respect to the first and second elements 1210, 1240, for at least a portion of its operation. The top surface 1271 may include first, second, third, and forth corner portions, $1271_{C1}$, $1271_{C2}$, $1271_{C3}$, $1271_{C4}$, respectively, and 1271C collectively. The second element 1240 and the third element 1270 may be adapted such that each of the four corner portions 1270C of the top surface 1171 move at one of a plurality of rates as the second element 1240 translates a first distance with respect to the third element 1270, and similar rates as the second element 1240 translates a second distance with respect to the third element 1270. More specifically, the third element 1270 may include one or more curvilinear surfaces 1278A and two or more linear surfaces 1278B, 1278C. The curvilinear surface 1278A may be configured or adapted to contact along a respective one of a plurality of curvilinear surfaces 1248A of second element 1240, while the two or more linear surfaces 1278B, 1278C may be configured or adapted to come in contact with a portion of one of a plurality of linear surfaces 1248B, 1248C, respectively. Accordingly, as the second element or sliding element 1240 initially translates between the first end 1212 and the second end 1214 of the base element 1210, the curvilinear surfaces 1248A contact and slide along corresponding respective curvilinear surfaces 1278A of the third element 1270, and the linear surface 1278C may contact and slide along linear surface 1248C at a specific location, such as near location 1248P as best viewed in FIG. 35, resulting in at least rotational movement of the element 1270 with respect to the first and second elements 1210, 1240. The amount of rotational movement can be defined by adjusting the slope of linear surface 1278C with respect to a generalized or averaged slope of curvilinear surface 1278A. While shown as curvilinear, the surface 1278A may be linear if desired, however a curvilinear surface 1278A may allow for better contact between the surfaces 1278A, 1248A and, therefore, better structural support therebetween.

Curvilinear surface 1248A of the second element and curvilinear surface 1278A of the third element 1270 may define a circle having a radius R, which defines a rate of curvature in conjunction with the slope of linear surface 1278C and, ultimately, differing rates of vertical movement along the top surface 1271 of the third element 1270, resulting in a top surface having a slope with respect to the bottom surface 1220 of the first element 1210. Therefore, the portion of the third element 1270 more distal may increase in height at a faster rate than the portion of the third element 1270 more proximal, resulting in rotational movement of the third element 1270 with respect to the base element 1210.

As the second element 1240 translates from the proximal end 1212 and toward the distal end 1214 of the intervertebral device 1200, the third element 1270 rotates with respect to the first and second elements 1210, 1240, until linear surface 1248B comes into contact with surface 1278B, as can be viewed in FIG. 36. At this point, linear surface 1248C may contact linear surface 1278C along a greater portion than what is represented by point 1248P of FIG. 35, for example. As depicted in FIG. 36, an angle $LA_9$ is defined by the top surface 1271 of third element 1270 with respect to the bottom surface 1220 of the base element 1210. Angle $LA_9$ may be the maximum angle achieved, the third element 1270 moving in the vertical direction upon further translation of the second element 1240 toward the distal end 1214 of the intervertebral device 1200, for example. It should be noted that this angle $LA_9$ may be defined through differing curvilinear surfaces. For example, curvilinear surfaces 1278A, 1248A may have different rates of curvature and the linear surfaces 1278C, 1248C may have different slopes compared to what is depicted in FIGS. 65-67, each combination resulting in one of numerous different angles defined by the top surface 1271 of the third element 1270 and bottom surface 1220 of the first element 1210. Such different angles may be greater than or less than angle $LA_9$, for example.

As depicted, when the linear surfaces 1248B, 1248C initially come into contact with corresponding linear surfaces 1278B, 1278C, respectively, the intervertebral device 1200 may have a proximal height $H_{9-2P}$ and a distal height $H_{9-2D}$. At this time, the void 1202 may have increased due to the expansion of the intervertebral device 1200 through initial rotational movement of the third element 1270 with respect to the first and second elements 1210, 1240. As the second element 1240 continues to move toward distal end 1214 of the intervertebral device 1200, the linear surfaces 1248B, 1248C of the second element 1240 move along linear surfaces 1278B, 1278C of the third element 1270, respectively, resulting in at least continued vertical movement of the third element 1270 with respect to the first and second elements 1210, 1240. Moreover, surfaces 1248B, 1278B, 1248C, 1278C may be curvilinear surfaces, such that the third element 1270 continues to rotate, as well as move vertically, with respect to the base element 1210. In this case, the curvilinear surfaces 1248B, 1278B, 1248C, 1278C may be selected to allow for a rate of rotation that is greater than or less than the initial rate of rotation.

With reference to FIG. 37, as the second element 1240 reaches a point closer to the distal end 1214 of the intervertebral device 1200, the third element reaches a maximum height, as compared to the base element 1210, for example. Since the third element 1270 first rotated, then moved vertically, with respect to the first and second elements 1210, 1240, different points along the top surface 1271 of the third element 1270 moved vertically at different rates. These different rates result in a maximum proximal height $H_{9-3P}$ and a maximum distal height $H_{9-3D}$. Since the motion of the third element 1270 from the configuration depicted in FIG. 36 to the expanded configuration of FIG. 37 is primarily vertical with respect to first and second elements 1210, 1240, the angle of the top surface 1271 with respect to the bottom surface 1220 of the first element 1210, $LA_9$, remains relatively constant.

As with other intervertebral devices described or contemplated herein, the first element or base element 1210 may include a plurality of engaging elements 1236 that protrude from a top inner surface of the bottom portion 1220 of element 1210. Second element 1240 may include a plurality of engaging elements 1250, at least one of the elements 1250 engaging a respective one of the plurality of engaging elements 1236. While depicted as being integral to the respective elements 1210, 1240, the engaging elements 1236, 1250 may be individual parts attached or affixed to the surfaces of the base element 1210 and sliding element 1240, respectively. As with the engaging elements 1136, 1150 of the intervertebral device 1100, the engaging elements 1236, 1250 are depicted as having similar shapes, e.g., triangular portions, however in other configurations, the shapes can be dissimilar, or may be nonsymmetrical along its vertical central axis, passing through the tip of each element 1236, 1250.

As with other intervertebral devices described herein, the intervertebral device 1200 is configured such that applying a lateral force to the sliding element 1240 to translate the element 1240 between the first and second ends 1212, 1214 of base member 1210, results in each engaging element 1250 sliding up and over a corresponding engaging element 1236, and engaging an adjacent engaging element 1236 in the direction of the movement of sliding element 1240. Accordingly, sliding element 1240, while primarily moving along the longitudinal axis of the base element 1210, also move vertically in accordance with the geometry outline and coupling of the engaging elements 1250, 1236 of the sliding element 1240 and base element 1210, respectively.

The intervertebral device 1200 may further include a plurality of pins 1245 coupled to sliding member 1240 and extending through corresponding groves 1228G in the side portions 1216, 1218 of base element 1210, the grooves 1228G being functionally similar to openings 728 of the intervertebral device 700. With the intervertebral device 1200 in the collapsed configuration, as depicted in FIG. 35, the sliding element 1240 is nearer the first end 1212, the pins 1245 being nearer the first end 1212, as well. With the intervertebral device 1200 in the fully expanded configuration, as depicted in FIG. 37, the sliding element 1240 is nearer the distal end or second end 1214, the pins 1245 being nearer the second end 1214, as well. The grooves 1228G of the first element 1210 may be spaced to allow some vertical travel of the sliding element 1240 and pins 1245 in accordance with the geometrical shapes, e.g. height, of the engaging elements 1250, 1236. It is noted that by adjusting the slope of each side surface of the engaging elements 1250, 1236 the translational force to move the sliding element 1240 in the presence of a compression force between the top portion 1271 of element 1270 and the bottom portion 1220 of the base element 1210 may differ in accordance with the corresponding element 1250, 1236 sloped surfaces. The slopes of each side surface of the engaging elements 1250, 1236, which may be linear, non-linear, or a combination thereof, may be configured to encourage movement of the sliding element 1240 in a first direction along the longitudinal axis of the base 1210 with respect to the sliding element 1240 in a second opposite direction. In any case, the engaging elements 1250, 1236 are configured, e.g., with suitable sloped surfaces or the like, to become locked or immovable when a compression force exists between the third element 1270 and the base element 1210.

Turning back specifically to FIG. 37, the sliding element 1240 may include a protrusion 1244 configured or adapted to slidably interface with a corresponding recessed portion or groove 1236A along the inner wall of the third element 1270. The protrusion 1244 may cooperate with recessed portion 1236A such that when the sliding element 1240 translates in a distal direction, in a direction toward distal end 1214 of the intervertebral device 1200 for example, one or more surfaces of the protrusion 1244 may engage corresponding one or more surfaces of the recessed portion 1236A to encourage the third element 1270 to move vertically and rotationally away from the first element 1210. Additionally, the protrusion 1244 may cooperate with the recessed portion 1236A such that when the sliding element 1240 translates in a proximal direction, in a direction toward the proximal end 1212 of the intervertebral device 1200 for example, one or more surfaces of the protrusion 1244 may engage corresponding one or more surfaces of the recessed portion 1236A to encourage the third element 1270 to move vertically and rotationally toward the first element 1210.

As with vertebral device 700, in the presence of a linear force applied to sliding element 1240 moving the element 1240 toward end 1214, in a ratcheting manner, for example, the engaging elements 1250, 1236 continuously engage and disengage with adjacent opposing engaging elements 1250, 1236. As the element 1240 translates, the third element 1270 moves vertically to increase the overall height, $H_9$, of the intervertebral device 1200. With a compression force applied between the third element 1270 and the base element 1210, e.g. when the device 700 is positioned between adjacent tissue surfaces, such as two adjacent vertebrae, the engaging elements 1250, 1236 of the sliding element 1240 and base element 1210, respectively, engage and prevent the sliding element 1240 from further translating. For illustration purposes only, the sliding element 1240 of the intervertebral device 1200 may be translated through the use of a tool or system, such as exemplary system 800 described above with respect to intervertebral device 700, the distal portion of the sliding element 1240 including protrusions 1240P and grooves 1240G similar to protrusions 740P and grooves 740G of the intervertebral device 700, adapted to interface with the delivery system 800, for example.

Figure 40:
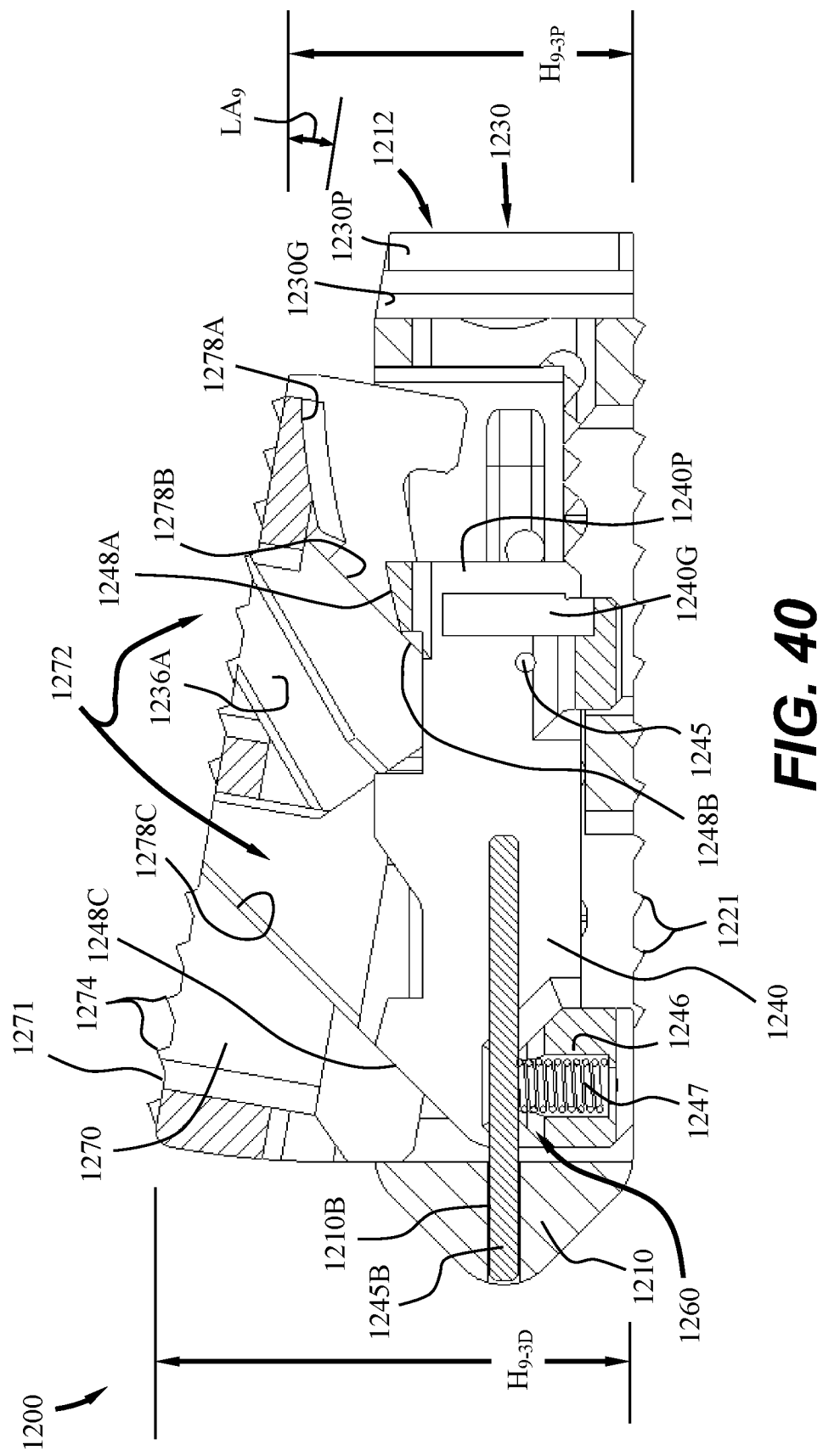

Turning to FIGS. 38-40, the intervertebral device 1200 is depicted in cross-section along section B-B of FIG. 34. The intervertebral device 1200 is depicted in a collapsed configuration in FIG. 38 and in a first expanded configuration in FIG. 39, and a second expanded configuration in FIG. 40. In particular, the sliding element 1240 includes a retention device 1260, as an alternative to the retention device 1160 of intervertebral device 1100, to aide in maintaining contact between the engaging element 1250, 1236 of the sliding element 1240 and base element 1210, respectively. The retention device 1260 includes the pin 1245B and spring 1247, the spring 1247 depicted in cross section and seated in a bore 1246. As depicted, the pin 1245B may extend from a bore 1210B of the first element 1210 to void 1202.

In operation, as the sliding element 1240 translates between the two ends 1212, 1214, the engaging elements 1250, 1236 repeatedly engage and disengage resulting in the sliding element 1240 repeatedly moving vertically away from and toward to the bottom portion 1220 of the base element 1210, as described above with respect to the intervertebral device 1200. As the engaging elements 1250 of the sliding element 1240 pass over the corresponding engaging elements 1236 of the base element 1210 the spring 1247 imparts a force upon the sliding element 1240 to encourage re-engagement of the adjacent engaging elements 1250, 1236. In this way, the engaging elements 1250 are biased to remain coupled to corresponding engaging elements 1236 during each movement of the sliding element 1240, particularly in a no-load situation, where the force between the third element 1270 and the first element 1210 is minimal for examples. Accordingly, when a compression force is applied between the top surface 1271 of the third element 1270 and the bottom surface 1220 of the base element 1210, engaging elements 1250, 1236 maintain the current position of all three elements 1210, 1240, 1270 and, ultimately, the current height, $H_{9\text{-}D}$, $H_{9\text{-}P}$ of the intervertebral device 1200.

As described above with respect to the intervertebral device 1100A of FIGS. 31A and 31B, the third element 1270 may include an angular top surface to better engage surrounding biological tissues, such as adjacent vertebral structures. Such angular top surfaces can allow for such engagement of surrounding biological tissues when positioned with differing methods, including TLIF and PLIF approaches.

The various mating curvilinear surfaces of the second and third elements of the various embodiments described herein may be adapted to provide a top surface of the intervertebral device, e.g., the top surface of the third element, at a desired angle with respect to a bottom surface of the intervertebral device, e.g., the bottom surface of the first element or base element. Such a desired angle may be selected in accordance with the approach taken to insert the intervertebral device between two adjacent vertebrae. In this way, the intervertebral device may be adapted to provide a desired height and angular configuration with respect to a specified approach such that the angular configuration matches the lordotic curvature of the spine, the lumbar or cervical regions of the spine, for example.

Figure 41A:
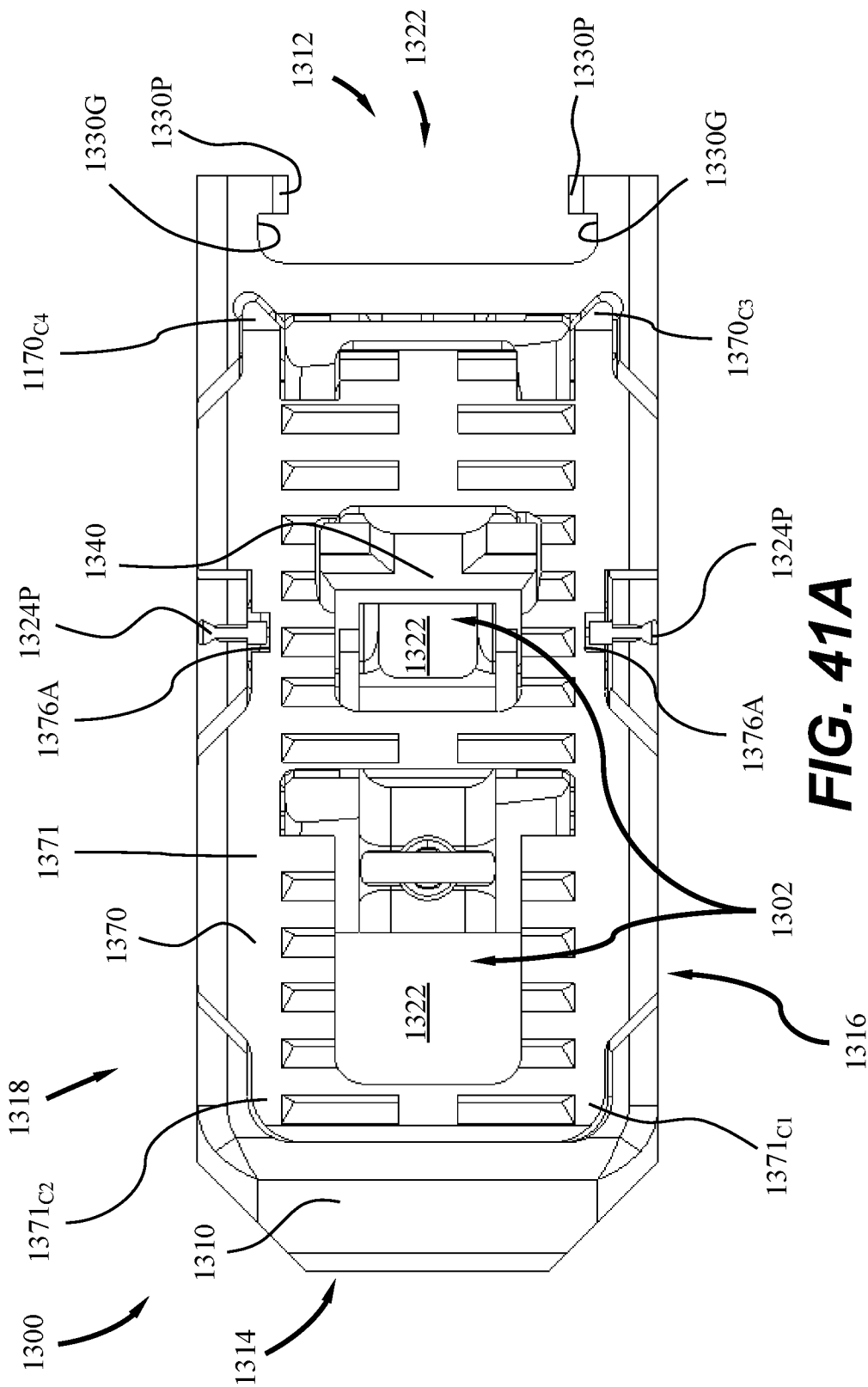
FIG. 41A is a top view of another exemplary intervertebral device.

Turning now to FIGS. 41A, 41B, and 41C, another exemplary intervertebral device 1300 includes a first or base element 1310, a second or sliding element 1340, and a third or lifting element 1370. The intervertebral device 1300 is generally similar to other intervertebral devices described or disclosed herein, however the first, second and third elements 1310, 1340, 1370 cooperate such that the third element 1370 is adapted to laterally rotate with respect to the other elements 1320, 1340 during operation. As with other embodiments described herein, the third element may include a top surface 1371 that may include first, second, third, and forth corner portions, $1371_{C1}$, $1371_{C2}$, $1371_{C3}$, $1371_{C4}$, respectively, and $1371_C$ collectively. The second element 1340 and the third element 1370 may be adapted such that each of the four corner portions 1370C of the top surface 1371 move at one of a plurality of rates as the second element 1340 translates with respect to the third element 1370. More specifically, the first corner portion $1371_{C1}$ and fourth corner portion $1371_{C4}$ may have a first rate, and the second corner portion $1371_{C2}$ and third corner portion $1371_{C3}$ may have a second rate, the second rate being greater than the first rate. In this way, for example, the third element 1370 may have a top planar surface 1371 that is angled with respect to a bottom planar surface 1320 of the base element 1310, as better viewed in FIGS. 41B and 41C, when the interventional device 1300 transitions from a collapsed configuration to an expanded configuration, respectively. Furthermore, as described in greater detail above with respect to intervertebral device 1100A, a top surface 1371 of the third element 1370 may be initially angled with respect to a bottom surface 1320 of the base element 1310 when in a collapsed configuration, such that when the third element 1370 is at least elevated a portion, its top planar surface may form a desired angle with respect to the bottom planar surface 1320 of the base element 1310. The intervertebral device 1300 includes a proximal end 1312 and a distal end 1314, as well as a first lateral side 1316 and a second lateral side 1318. The proximal end 1312 may include geometric structures 1330G, 1330P for positioning the intervertebral device 1300, as described in greater detail above with respect to other embodiments. The first, second, and third elements 1310, 1340, 1370 further cooperate to provide an internal open space or void 1302 for deployment of therapeutic agents, as discussed herein.

Turning specifically to FIG. 41B, the intervertebral device 1300 is depicted in a collapsed configuration, the elongated shaft 900 of the delivery system 800 engaged with the sliding element 1340, in accordance with the discussion above with respect to attaching the system 800 to the intervertebral device 700. The grasping unit 840 and associated structures have been removed to allow for a better view of the operation. The delivery system 800 may include portions that interface with one or more recesses 1332 to fixedly hold the intervertebral device 1300 in contact with the delivery system 800, but such portions have been removed for this specific discussion. Turning also to FIG. 41C, when the elongate shaft 602 is translated toward distal end 1314 of the intervertebral device 1300, in a direction indicated by arrow $41C_4$, the sliding or second element 1340 also translates in a distal direction. As the sliding element 1340 moves distally various surfaces of the sliding element 1340 cooperate with corresponding various surfaces of the lifting element 1370 such that the top surface 1371 moves in a rotationally vertical direction away from the base element 1310, for example, as described in greater detail below.

Figure 42:
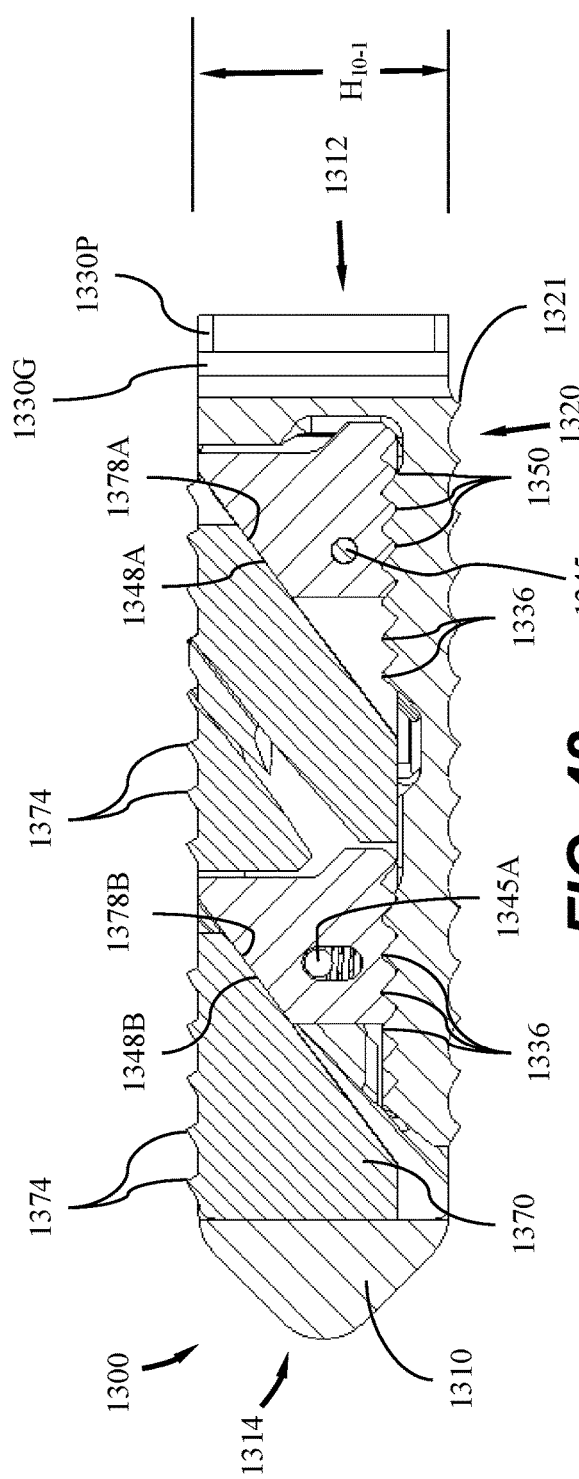
Figure 43:
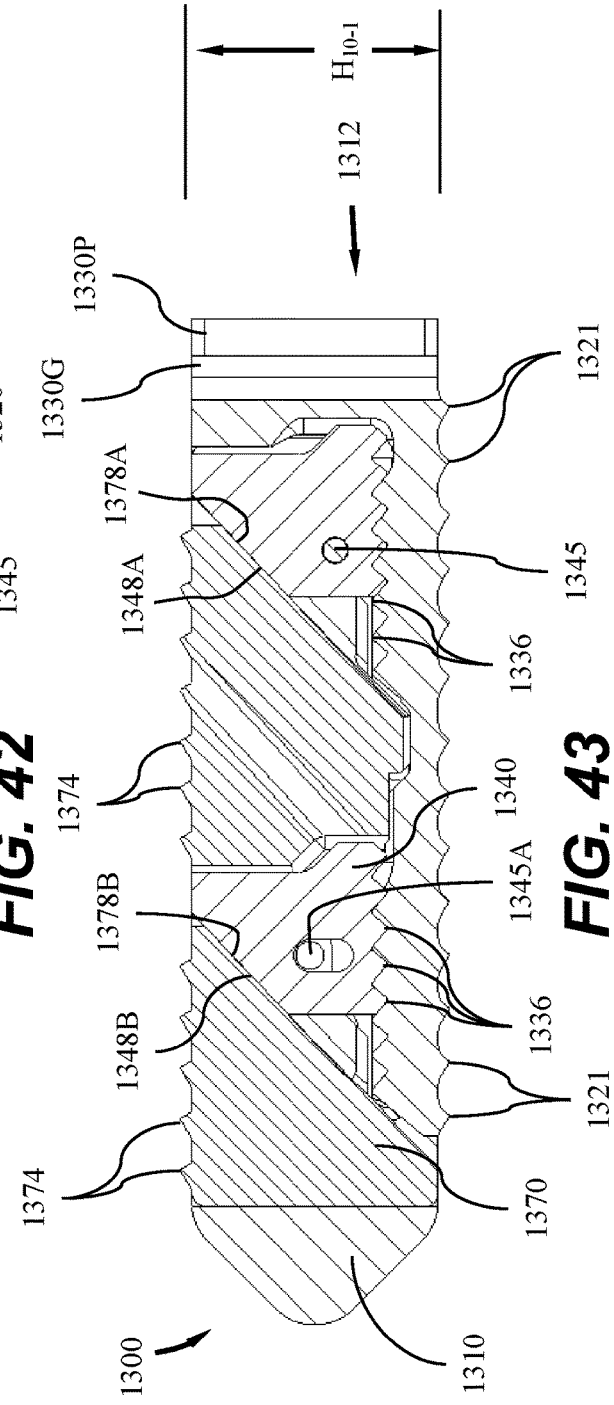
Figure 44:
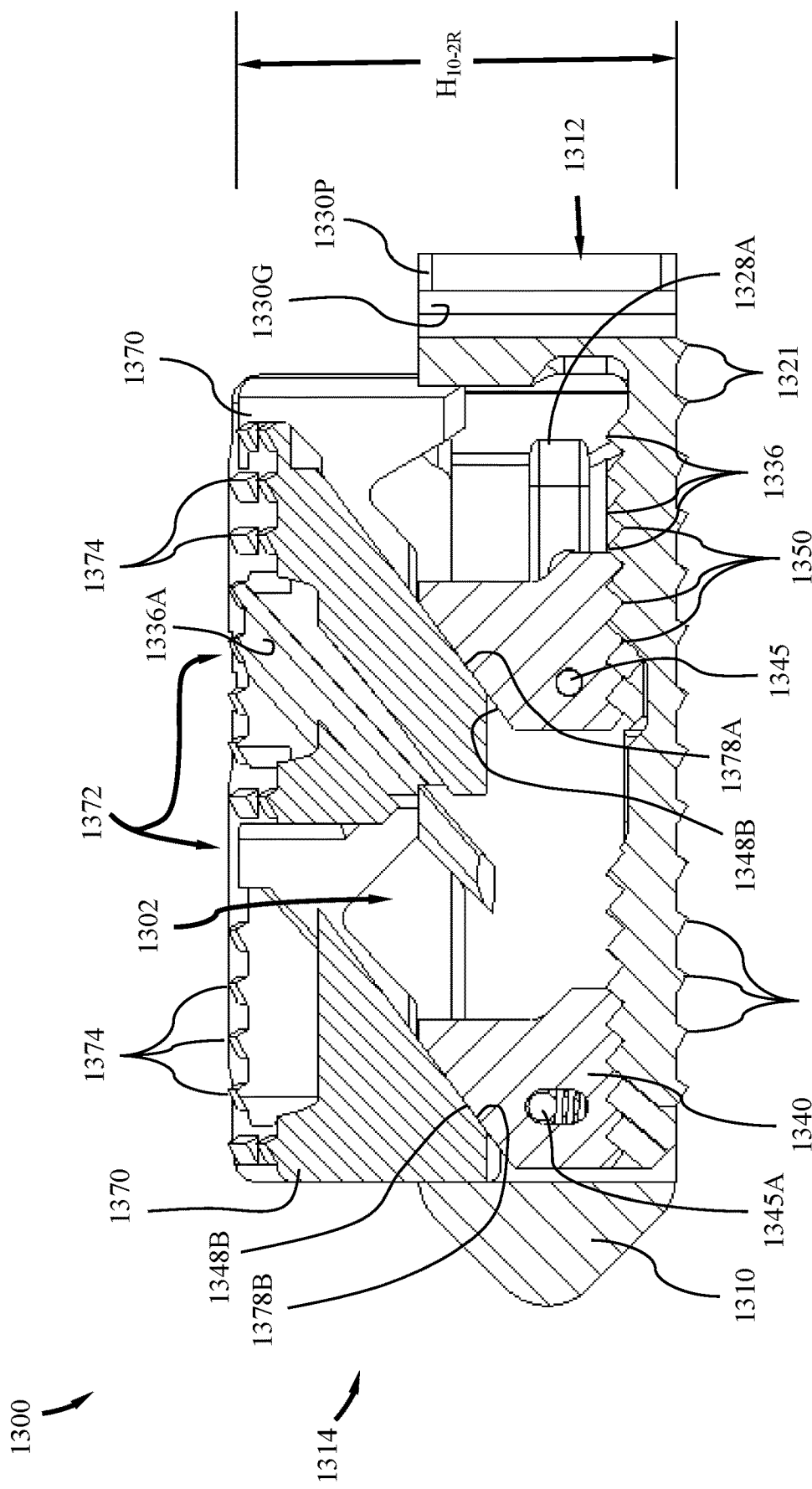

Turning to FIGS. 42-45, elevated side views of the exemplary intervertebral device 1300 are depicted in cut view along section A-A of FIG. 41A in FIGS. 42 and 44 and along section B-B of FIG. 41A in FIGS. 43 and 45. As with other intervertebral devices described or contemplated herein and better understood in light of the discussion below, the elements 1310, 1340, 1370 cooperate such that the intervertebral device 1300 geometric height, $H_{10}$, may have a minimum value, $H_{10-1}$, when the device 1300 is in a collapsed configuration, as generally depicted in FIGS. 42 and 43, a maximum height, $H_{10-2}$, when the device 1300 is in an expanded configuration, as generally depicted in FIGS. 44 and 45, and an intermediate value, $H_{10}$, when the device 1300 is in an intermediate configuration therebetween.

The first element 1310, also referred to as base 1310 or base element 1310, may be configured to provide a base or outer structure for the intervertebral device 1300, and includes a first end 1312, a second end 1314, and two side portions, a first side portion 1316 and an opposing side portion 1318, as better viewed, for example, in FIG. 41A. A bottom portion 1320 of the first element 1310 may include one or more openings 1322, as depicted also in FIG. 41A, allowing for one or more therapeutic agents to pass therethrough, for example. It should be readily understood that the second and third elements 1340, 1370 may also include similar openings for the same or differing purposes. As with other embodiments described or contemplated herein, the proximal end 1312 may include an opening 1330 for passing a portion of one or more tools utilized for delivery of said therapeutic materials, or expanding, contracting, or locking the intervertebral device 1300 in a specific configuration, for example. Such one or more tools may include, or be similar to, delivery system 800 and the delivery tool 1000.

The intervertebral device 1300 may be expanded or contracted to any suitable height, $H_{10}$, between a first collapsed height $H_{10-1}$, as depicted in FIG. 72, for example, and second expanded heights $H_{10-2R}$ and $H_{10-2L}$, as depicted generally in FIGS. 46A and 46B. As described in greater detail below, since the third element 1370 is configured to at least rotate with respect to the first and second elements 1310, 1340, when the intervertebral device 1300 is in an expanded configuration, a first lateral portion of the third element 1370 may have a first height $H_{10-2R}$ and a second lateral portion of the third element 1370 may have a second height $H_{10-2L}$, as viewed in FIGS. 46A and 46B, respectively. The proximal end 1312 may also include structures, such as protrusions 1330P and grooves 1330G, which may allow for attachment points to a delivery system (not shown), as described above with respect to delivery device 800 of FIG. 6, for example. Such attachment points may also form the basis for at least initially positioning the intervertebral device 1300, for example between two adjacent vertebrae, through an approach described or contemplated herein, or otherwise known in the art. As described in greater detail above, the delivery system 800 may include tubular members through which therapeutic agents may be introduced, for example, to internal spaces within the intervertebral device 1300 and exiting through the one or more openings 1322 of the element 1310 or one or more openings 1372 of the element 1370, or other similar openings of the elements 1310, 1340, 1370. In this way, such therapeutic agents or materials may contact surrounding tissues, such as bone tissue, encouraging healing.

As with other intervertebral devices described or contemplated herein, the third element 1370 may be slidably interfaced to the first and second elements 1310, 1340 such that the third element 1370 at least slides vertically with respect to the first and second elements 1310, 1340. The top portion 1371 may include one or more protrusions 1374 that may aide in holding the top surface 1371 immobile with respect to adjacent structures or biological tissue, such as vertebral structures for example. While only a few protrusions 1374 are identified, additional or less protrusions 1374 may be utilized. Such protrusion structures 1374 may be constructed from any biocompatible material and in any suitable form and may be applied to any embodiment described or contemplated herein. Additionally, sidewalls 1316, 1318 of element 1310 may include one or more protrusions (not shown), and a bottom portion 1320 of base 1210 may include one or more protrusions 1321. Protrusions 1321 may be, for example, similar to or different from protrusions 1374, and may aide in holding a bottom portion 1320 immobile with respect to adjacent structures or biological tissue, such as vertebral structures.

Turning temporarily back to FIG. 41A, the base element 1310 may include a positioning structure or pin 1324P which may be configured or adapted to move within a corresponding channel 1376A to ensure that the element 1370 moves in a specific manner with respect to the base element 1310.

As with other intervertebral devices described or contemplated herein, a void or space 1302 is defined by the first, second, and third elements 1310, 1340, 1370 of the intervertebral device 1300, the void increasing in volume as the device 1300 transitions from a collapsed configuration to an expanded configuration. In this way, once the device 1300 is deployed, one or more therapeutic agents may be positioned within the void 1302. Such therapeutic agents may further flow out of the open space via additional openings, such as openings 1372 and 1322, or other openings positioned about the elements 1310, 1340, 1370.

The third element 1370 of intervertebral device 1300 at least rotates with respect to the first and second elements 1310, 1340. As with other intervertebral devices described or contemplated herein, the intervertebral device 1300 utilizes interfacing, interacting or mating surfaces between the second and third elements 1340, 1370, however the surfaces of the intervertebral device 1300 may include curvilinear portions to encourage at least rotational movement of the third element 130 with respect to the first and second elements 1310, 1340. Such curvilinear surfaces may be helical in nature, for example, to provide the desired rotation, which results in a desired angular relationship between the top surface 1371 of the third element 1370 and the bottom surface 1120 of the first element 1310 and a desired height, $H_{10}$, when in an intermediate or expanded configuration. Such curvilinear surfaces may also allow for various portions of the third element 1370 to move at different rates with respect to the first and second elements 1310, 1340, for at least a portion of its operation. Accordingly, as the second element or sliding element 1340 translates between the first end 1312 and the second end 1314 of the base element 1310, the curvilinear surfaces 1348A contact and slide along corresponding respective curvilinear surfaces 1378A of the third element 1370, and the curvilinear surface 1378C may contact and slide along curvilinear surface 1348C at a specific location, resulting in at least rotational movement of the element 1370 with respect to the first and second elements 1310, 1340. The amount of rotational movement can be defined by adjusting the geometry of surface 1378C with respect to the geometry of surface 1378A. While the surfaces 1348A, 1348B, 1378A, 1378B are described as being curvilinear surfaces, they may also include linear portions, depending on the overall desired movement to be achieved by the lifting element 1370. In this example, the desired rotational movement of the intervertebral device 1300 results in curvilinear surfaces 1348A, 1348B being similar in geometric form, as is discussed in greater detail below with respect to FIGS. 47-50.

As shown in FIGS. 44 and 45, in the expanded configuration the top surface 1371 of the third or lifting element 1370 may be angled with respect to the bottom surface 1320 of the base element 1310. Turning now to FIGS. 46A and 46B, the right lateral portion 1370R of the lifting element 1370, which includes second corner portion $1371_{C2}$ and third corner portion $1371_{C3}$, achieves a height $H_{10-2R}$ in the expanded configuration, while the left lateral portion 1370L of the lifting element 1370, which includes first corner portion $1371_{C1}$ and fourth corner portion $1371_{C4}$, achieves a height $H_{10-2L}$. The top surface 1371 of the lifting element 1370 may define a geometric plane that forms an angle with respect to the planar surface 1320 of the base element 1310, the angle represented by angle 1371A. As is discussed below with respect to FIGS. 47-50, this angle 1371A may be defined such that a desired angle is achieved, with a corresponding desired height $H_{10}$, when the intervertebral device 1300 is in its final configuration, which may be an intermediate configuration or its expanded configuration.

Turning to FIGS. 47-50, the formation of the certain various curvilinear surfaces 1348, 1378 of the intervertebral device 1300 will be described in greater detail, from which any suitable curvilinear surface may be derived, as part of one or more intervertebral devices described or contemplated herein for example. As with other embodiments described or contemplated herein, the parameters of the intervertebral device 1300 may first be defined. Such defined parameters may include a height, $H_{10}$, both when in a collapsed configuration and when in an expanded configuration, as well as the desired angular relationship between top surface 1371 of the third element 1370 and the bottom surface 1320 of the base element 1310. For illustration purposes only, the intervertebral device 1300 may be defined to have an initial collapsed configuration height, $H_{10-1}$, of 7 mm, and an expanded configuration height, $H_{10-2R}$, of 12 mm, requiring a right lateral edge of the top surface including the second and third corner portions $1371_{C2}$, $1371_{C4}$, to expand 5 mm. That is, the expanded height, $H_{10-2R}$, less the initial height, $H_{10-1}$, equals 5 mm. For a desired exemplary angle of 10° lateral tilt, e.g. defining an angle 1371A of 10°, the center of axis, Rc, about which the right lateral edge rotates must first be determined.

With the highest outside edge of the top surface 1371 of the third element 1370 being 5 mm higher in the expanded position as compared to the inside edge of the top surface 1371 of the third element 1370, and with an angle of 10 degrees tilt of the top surface 1371, a circle or arc must exist where it's radius times the sin of 10 degrees equals this height differential, 5 mm. That radius is approximately 1.15 inches, and if the cage is 0.5 inches wide, then the center of that radius is 1.15 inches from the far lateral side 1316 and 0.65 inches from the near side 1318 of the intervertebral device 1300. The center of the arc of rotation is collinear with the axis that the top plate rotates about. This axis does not have to be coplanar with the top surface 1371 of the third element 1370, but can be positioned higher or lower than the top surface 1371 of the third element 1370, as desired, to best facilitate it moving with the first and second elements 1310, 1340, while still lifting and rotating the desired amount.

Figure 50:
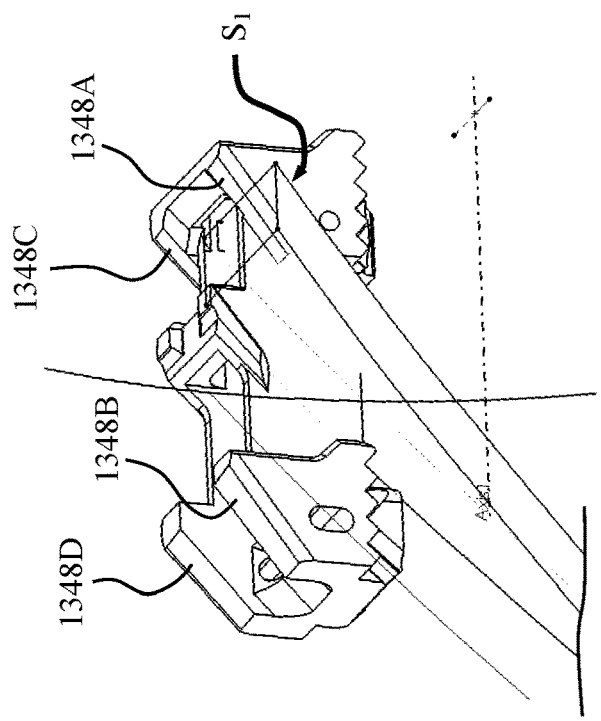
FIG. 50 is yet another graph depicting certain geometric properties of the exemplary intervertebral device of FIG. 41A.
Figure 49:
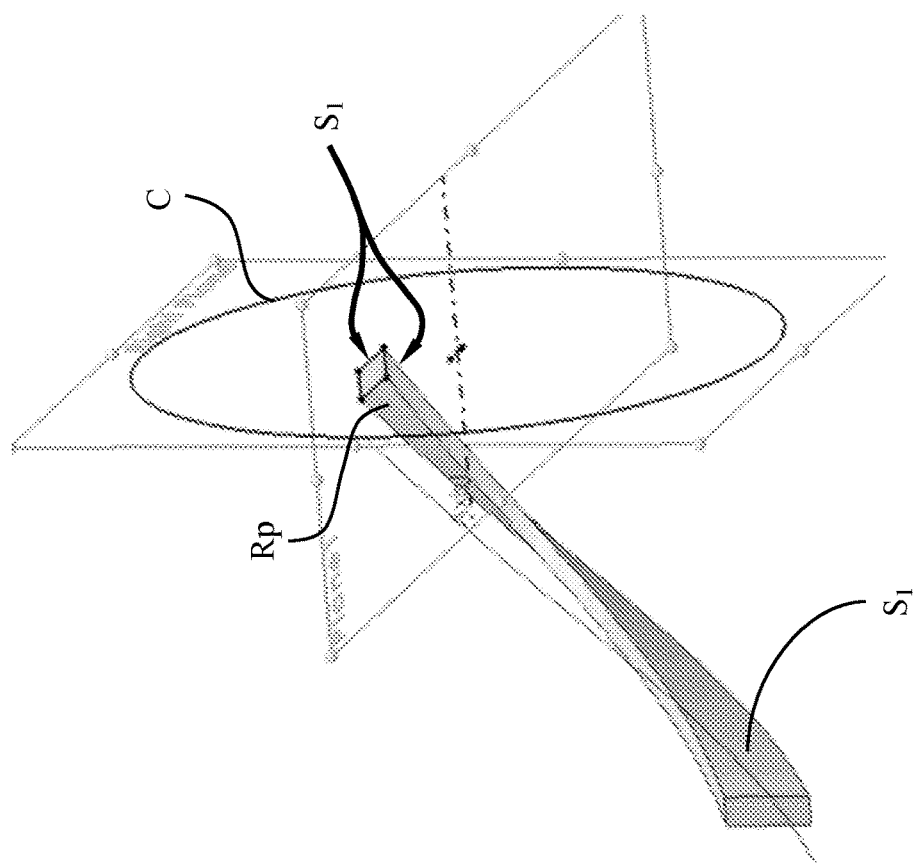
FIG. 49 is another graph depicting certain geometric properties of the exemplary intervertebral device of FIG. 41A.

The distance the second or sliding element 1340 must be able to move distally must also be determined or defined. For example, we may desire for every 0.2 inches that the sliding element 1340 moves in the distal direction, the top plate will rotate 10 degrees, e.g., having its outer edge of the top surface 1371 elevated 0.2 inches. With specific reference to FIG. 49, a circle, C, is drawn in a Right Plane with the center located on the axis of rotation, labeled Axis 1. A helical curve is drawn, as shown, starting at the 3 o'clock position (or 9 o'clock, depending on from what side you are looking at the circle), extending and rotating at a rate of 10 degrees per 0.2 inches, and rotating for at least some distance, for example, for 90 degrees as shown. A rectangular pattern RP is provided starting at a surface of a plane, labeled Plane 1, and transitioned along the helical path described above, forming a solid helical structure. A first side surface S1 of this solid helical structure defines the curvilinear surface of the two proximal surfaces, e.g., 1348A, 1348C, of the sliding element 1340, as generally depicted in FIG. 50.

The two proximal surfaces 1348A, 1348C of the sliding element 1340 are relatively coplanar, however, don't necessarily need to be represented by the first side S1 of this one solid helical structure RP. Rather, each of the proximal surfaces 1348A, 1348C may be represented by any solid helical structural surface that has its axis of rotation at Axis 1 and has it's rotation to distance ratio at 10 degrees per 0.20 inches. All the curvilinear surfaces 1348 of the sliding element 1340 must share the same axis of rotation and rate of rotation, 10 degrees per 0.20 inches in this case.

The mating curvilinear surfaces 1378 of the third element 1370 are simply the exact same curvilinear surfaces 1348 of the second element 1140, however, are defined by a solid helical structure coming from the opposite side of curvilinear surfaces 1348.

The first element or base element 1310 may further include a plurality of engaging elements 1336 protruding from a top inner surface of the bottom portion 1320 of element 1310. Second element 1340 may include a plurality of engaging elements 1350, at least one of the elements 1350 engaging a respective one of the plurality of engaging elements 1336 of the base element 1310. While depicted as being integral to the respective elements 1310, 1340, the engaging elements 1336, 1350 may be individual parts attached or affixed to the surfaces of the base element 1310 and sliding element 1340, respectively. The engaging elements 1336, 1350 are depicted as having similar shapes, e.g., triangular portions, however in other configurations, the shapes can be dissimilar, or may be nonsymmetrical along its vertical central axis, passing through the tip of each element 1336, 1350.

intervertebral device 1300 may include further include a plurality of pins 1345 coupled to sliding member 1340. Rather than extending through openings, such as opening 728 of intervertebral device 700, the pins 1345 may extend within grooves 1328A on the inner walls of side portions 1316, 1318 of base element 1310, as best viewed in FIGS. 44 and 45. These grooves may provide surfaces such that the pins behave similarly as if they extended through slots, as described above with respect to intervertebral device 700. With the intervertebral device 1300 in the collapsed configuration, as depicted in FIGS. 42 and 43, the sliding element 1340 is nearer the first end 1312, the pins 1345 being nearer the first end 1312, as well. With the intervertebral device 1300 in the expanded configuration, as depicted in FIGS. 44 and 45, the sliding element 1340 is nearer the distal end or second end 1314, the pins 1345 being nearer the second end 1314, as well. The grooves 1328A of the first element 1310 may be spaced to allow some vertical travel of the sliding element 1340 and pins 1345 in accordance with the geometrical shapes, e.g. height, of the engaging elements 1336. It is noted that by adjusting the slope or curvilinear shape of each side surface of the engaging elements 1350, 1336 the translational force to move the sliding element 1340 in the presence of a compression force between the top surface 1371 of element 1370 and the bottom portion 1320 of the base element 1310 may differ in accordance with the corresponding element 1350, 1336 shaped surfaces. The geometric shape of each side surface of the engaging elements 1350, 1336, which may be linear or curvilinear, or a combination thereof, may be configured to encourage movement of the sliding element 1340 in a first direction along the longitudinal axis of the base 1310 with respect to movement of the sliding element 1340 in a second opposite direction. In any case, the engaging elements 1350, 1336 are configured, e.g., with suitable shaped surfaces or the like, to become locked or immovable when a compression force exists between the third element 1370 and the base element 1310.

As with vertebral device 700, in the presence of a linear force applied to sliding element 1340 moving the element 1340 toward the distal end 1314, in a ratcheting manner, for example, the engaging elements 1350, 1336 continuously engage and disengage with adjacent opposing engaging elements 1350, 1336. As the element 1340 translates, the third element 1370 moves vertically to increase the overall height, $H_{10}$, of the device 1100. With a compression force applied between the third element 1370 and the base element 1310, e.g. when the device 1300 is positioned between adjacent tissue surfaces, such as two adjacent vertebrae, the engaging elements 1350, 1336 of the sliding element 1340 and base element 1310, respectively, engage and prevent the sliding element 1340 from further translating. For illustration purposes only, the sliding element 1340 of the intervertebral device 1300 may be translated through the use of a tool, such as expansion tool 860 described above for example, the distal portion of the sliding element 1340 including protrusions 1340P and grooves 1340G, similar to protrusions 740P and grooves 740G of intervertebral device 700, for example.

Figure 51A:
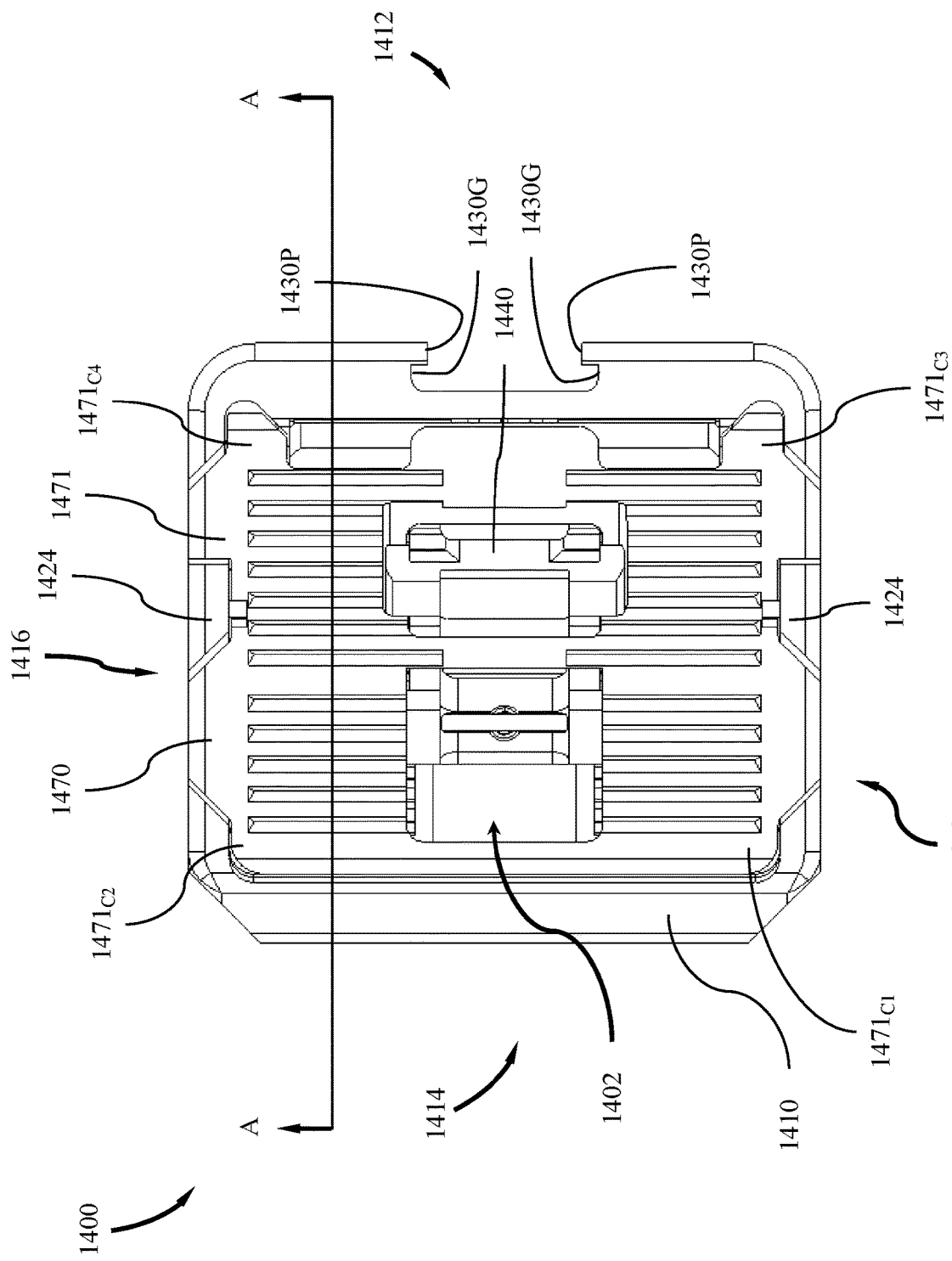
FIG. 51A is a top view of yet another exemplary intervertebral device.
Figures 51B, 51C:
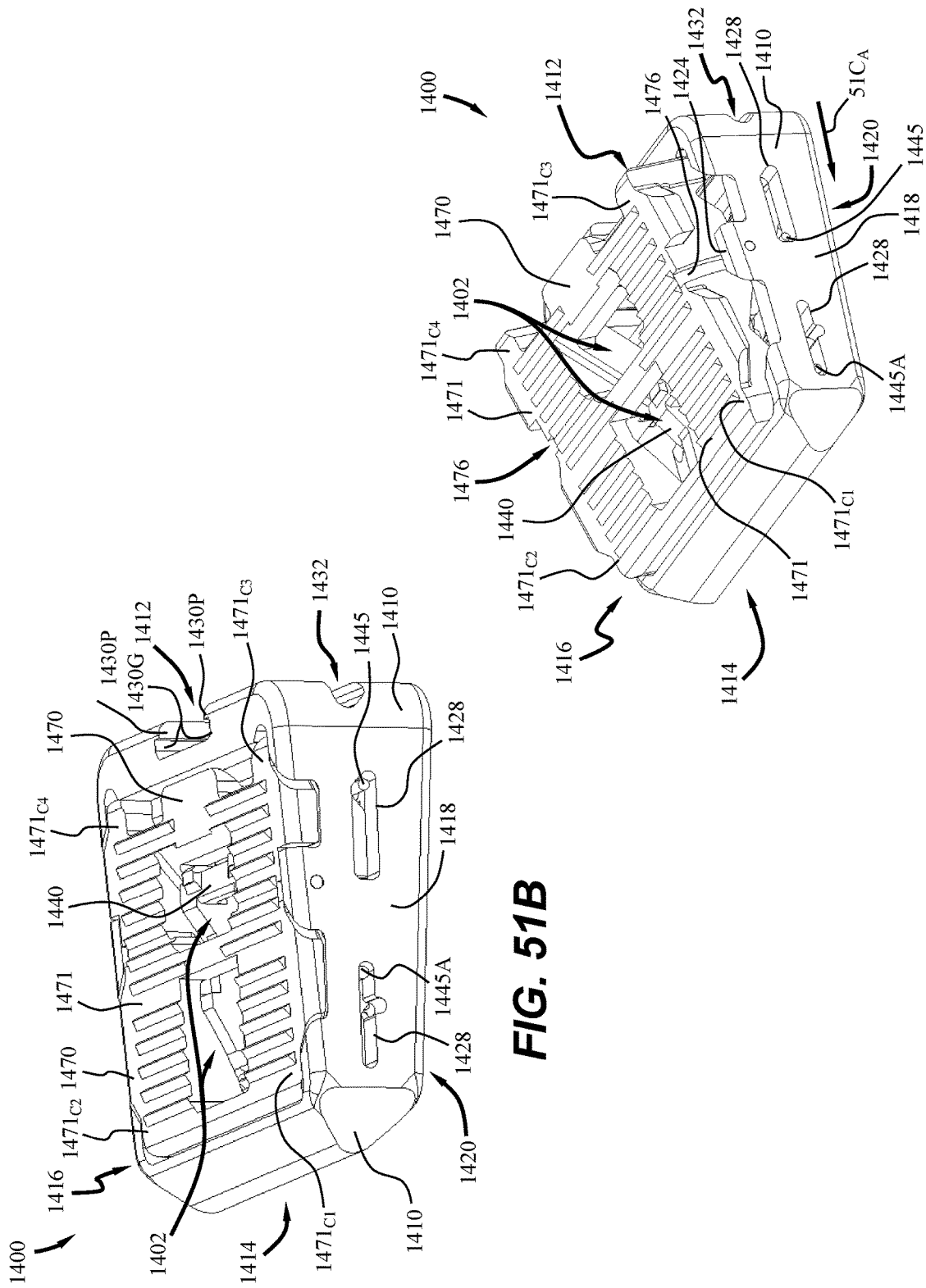
FIGS. 51B-51C are prospective views of the exemplary intervertebral device of FIG. 51A.

Turning now to FIGS. 51A, 51B, and 51C, yet another exemplary intervertebral device 1400 includes a first or base element 1410, a second or sliding element 1440, and a third or lifting element 1470. The intervertebral device 1400 is generally similar to other intervertebral devices described or disclosed herein, however the first, second and third elements 1410, 1440, 1470 cooperate such that the third element 1470 is adapted to rotate with respect to the other elements 1420, 1440 during operation and along a longitudinal axis of the third element 1470, a height of the distal portion 1414 of the device 1400 being less than a height of the proximal portion 1412 when the device 1400 is in an expanded configuration. As with other embodiments described herein, the third element 1470 may include a top surface 1471 that may include first, second, third, and forth corner portions, $1471_{C1}$, $1471_{C2}$, $1471_{C3}$, $1471_{C4}$, respectively, and $1471_C$ collectively. The second element 1440 and the third element 1470 may be adapted such that each of the four corner portions $1470_C$ of the top surface 1471 move at one of a plurality of rates as the second element 1440 translates with respect to the third element 1470. More specifically, the first corner portion $1471_{C1}$ and second corner portion $1471_{C2}$ may have a first rate, and the third corner portion $1471_{C3}$ and forth corner portion $1471_{C4}$ may have a second rate, the second rate being greater than the first rate. In this way, for example, the third element 1470 may have a top planar surface 1471 that is angled with respect to a bottom planar surface 1420 of the base element 1410, as better viewed in FIGS. 51B and 51C, when the interventional device 1400 transitions from a collapsed configuration to an expanded configuration. Furthermore, as described in greater detail above with respect to intervertebral device 1100A, the top surface 1471 of the third element 1470 may be initially angled with respect to a bottom surface 1420 of the base element 1410 when in a collapsed configuration, such that when the third element 1470 is at least elevated a portion, its top planar surface 1471 may form a desired angle with respect to the bottom planar surface 1420 of the base element 1410. The intervertebral device 1400 includes a proximal end 1412 and a distal end 1414, as well as a first lateral side 1416 and a second lateral side 1418. The proximal end 1412 may include geometric structures 1430G, 1430P for positioning the intervertebral device 1400, as described in greater detail above with respect to other embodiments. The first, second, and third elements 1410, 1440, 1470 further cooperate to provide an internal open space or void 1402 for deployment of therapeutic agents, as discussed herein.

Turning specifically to FIG. 51B, the intervertebral device 1400 is depicted in a collapsed configuration. The base element 1410 and the sliding element 1440 include various protrusions and grooves to allow for interfacing the device 1400 to a delivery system, such as delivery system 800. For example, the elongated shaft 900 of the delivery system 800 may engage the sliding element 1340 and may engage groove 1430G and protrusion 1430P of the base element 1410, both in accordance with the discussion above. The delivery system 800 may further include portions that interface with one or more recesses 1432 to fixedly hold the intervertebral device 1400 in contact with the delivery system 800. Turning also to FIG. 51C, when the elongate shaft 900 is translated toward distal end 1414 of the intervertebral device 1400, in a direction indicated by arrow $51C_A$, the sliding or second element 1440 also translates in a distal direction. As the sliding element 1440 moves distally various curvilinear surfaces of the sliding element 1440 cooperate with corresponding various curvilinear surfaces of the lifting element 1470 such that the top surface 1471 moves in a rotationally vertical direction away from the base element 1410, for example, as described in greater detail below.

Figure 52A:
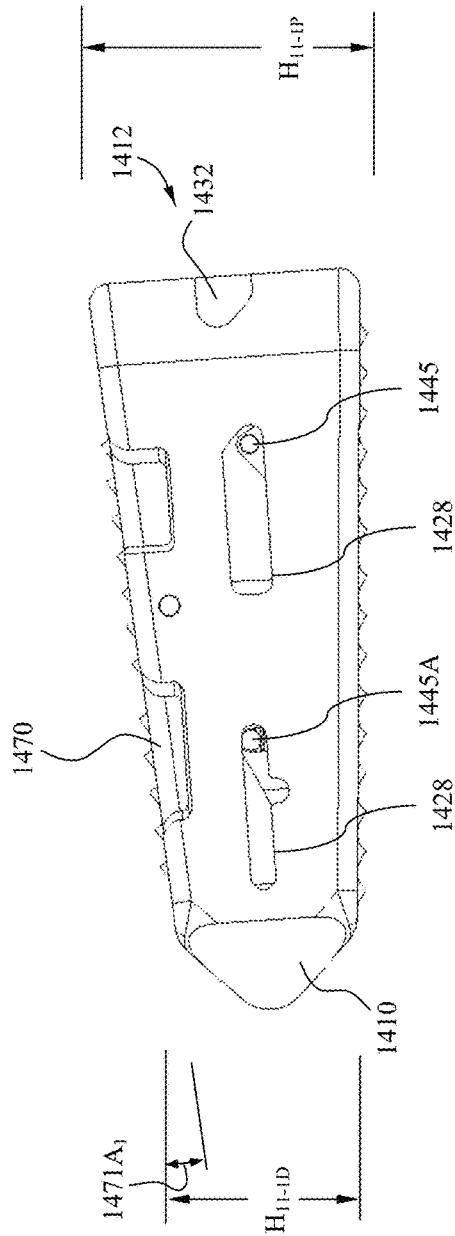
FIGS. 52A-52B are side elevation views of the exemplary intervertebral device of FIG. 51A.
Figure 52B:
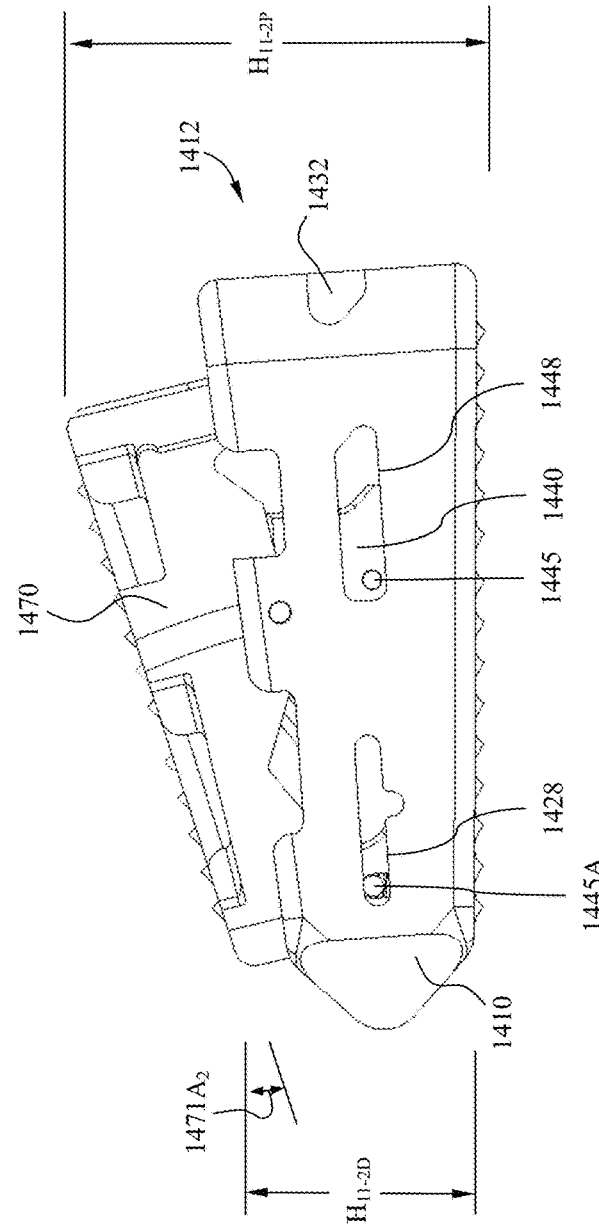

Turning now to FIG. 52A, since the intervertebral device 1400 includes a sloped top surface 1471 as compared to a bottom surface 1420 of the base 1410, in a collapsed position the intervertebral device 1400 may have a first distal height $H_{11-1D}$ and a first proximal height $H_{11-1P}$. The top surface may define an angle $1471A_1$ with respect to a longitudinal axis parallel to the bottom surface 1420 of the base 1410. In the collapsed configuration the sliding element 1430 is in its most proximal position. Turning now to FIG. 52B, the sliding element 1430 has moved from its most proximal position to its most distal position, the third element 1470 rotating with respect to the base element 1410 such that the top surface 1471 has a second distal height $H_{11-2D}$ and a second proximal height $H_{11-2P}$. The top surface 1471 of the third element 1470 forms a second angle $1471A_2$ with respect to a longitudinal axis parallel to the bottom surface 1420 of the base element 1410.

Turning also to FIGS. 53A and 53B, in which perspective views of the exemplary intervertebral device 1400 are depicted in cut view along section A-A of FIG. 51A, as with other intervertebral devices described or contemplated herein, and discussed above, the elements 1410, 1440, 1470 cooperate such that the intervertebral device 1400 has a geometric height, $H_{11}$, may have a minimum height, $H_{11-1}$, in a collapsed configuration, as generally depicted in FIG. 53A, and a maximum height, $H_{11-2}$, in an expanded configuration, as generally depicted in FIG. 53B. As discussed immediately above, the intervertebral device 1400 in a collapsed configuration has a first distal height $H_{11-1D}$ and a first proximal height $H_{11-1P}$, and in an expanded configuration has a second distal height $H_{11-2D}$ and a second proximal height $H_{11-2P}$.

The first element 1410, also referred to as base 1410 or base element 1410, may be configured to provide a base or outer structure for the intervertebral device 1400, and includes a first end 1412, a second end 1414, and two side portions, a first side portion 1416 and an opposing side portion 1118 (as shown in FIGS. 51A-51C). A bottom portion 1420 includes one or more openings 1422, allowing for one or more therapeutic agents to pass therethrough, for example. The second and third elements 1440, 1470 may also include similar openings for the same or differing purposes. The proximal end 1412 may include an opening 1430 at the proximal end 1412 for passing a portion of one or more tools utilized for delivery of said therapeutic materials, or expanding, contracting, or locking the intervertebral device 1400 in a specific configuration, for example. Such an opening 1430 may be similar, for example, to opening 1330 of the intervertebral device 1300, as depicted in FIG. 46A. As with other intervertebral devices described or contemplated herein, utilizing a single connecting point on the device 1400 for interfacing with a tool that can allow for other tools to be easily attached, tools for expanding, contracting or locking the device 1400 in a specific configuration, or tools for delivery of therapeutic materials, provides for a more efficient system, allowing a user to more easily place, position, manipulate, and operate the device 1400.

The intervertebral device 1400 may be expanded or contracted to any suitable height, $H_{11}$, between a first collapsed heights $H_{11-1D}$, $H_{11-1P}$, as depicted in FIG. 53A, and second expanded heights $H_{11-2D}$ and $H_{11-2P}$, as depicted in FIG. 53B. As described in greater detail below, since the third element 1470 is configured to rotate with respect to the first and second elements 1410, 1440 as the intervertebral device 1300 transitions from a collapsed configuration to an expanded configuration, a distal portion of the third element 1470 may have a first expanded height $H_{11-2D}$ and a proximal portion of the third element 1470 may have a second height $H_{8-2P}$. For example, the intervertebral device 1400 may be expanded from a first position, having minimum distal height of $H_{11-1D}$ and a minimum proximal height $H_{11-1P}$ as depicted in FIG. 53A, to a second position, having a maximum distal height of $H_{11-2D}$ and a maximum proximal height of $H_{11-2P}$ as depicted in FIG. 28, or another position therebetween, and locked in that corresponding position.

The proximal end 1412 may also include structures, such as protrusions 1430P and grooves 1430G, which may allow for attachment points to a delivery system (not shown), as described above with respect to delivery device 800 of FIG. 6, for example, in a similar manner as intervertebral device 1100, for example. In this way, such therapeutic agents or materials may contact surrounding tissues, such as bone tissue, encouraging healing. The tubular members to perform these functions may be the same tubular member or different tubular members.

As with other intervertebral devices described or contemplated herein, the third element 1470 may be slidably interfaced to the first and second elements 1410, 1440 such that the third element 1470 at least slides vertically with respect to the first and second elements 1410, 1440, as well as rotationally. The third element 1470 may include one or more openings 1472 in the top portion or surface 1471 thereof to allow for passage or introduction of therapeutic elements or bone growth enhancing materials therethrough. The top portion 1471 may include one or more protrusions 1474 that may aide in holding the top portion 1471 immobile with respect to adjacent structures or biological tissue, such as vertebrae structures for example. While only a few protrusions 1474 are identified, additional or less protrusions 1474 may be utilized. Such protrusion structures 1474 may be constructed from any biocompatible material and in any suitable form. Additionally, sidewalls 1416, 1418 of element 1410 may include one or more protrusions (not shown), and a bottom portion or surface 1420 of base 1410 may include one or more protrusions 1421. Protrusions 1421 may be, for example, similar to protrusions 1474, which may aide in holding a bottom portion 1420 immobile with respect to adjacent structures or biological tissue, such as vertebral structures for example.

The first element 1410 may include a positioning structure or protrusion 1424, which may be configured or adapted to move within a corresponding channel 1476 of the third element 1470 to ensure the third element 1470 moves in a specific direction with respect to the base element 1410. In this case, the protrusion 1424 and corresponding channel 1476 may be curvilinear to allow for rotation of the third element 1470 with respect to the second element 1440 as the second element 1440 translates.

As with other intervertebral devices described or contemplated herein, a void or space 1402 is defined by the first, second, and third elements 1410, 1440, 1470 of the intervertebral device 1400, the void 1402 increasing as the device 1400 transitions from a collapsed configuration to an expanded configuration. In this way, once the device 1400 is deployed, one or more therapeutic agents may be positioned within the void 1402. As described above, such therapeutic agents may further flow out of the void 1402 via additional openings, such as openings 1472 and 1422, positioned about the elements 1410, 1440, 1470.

In operation, the third element 1470 of intervertebral device 1400 at least rotates with respect to the first and second elements 1410, 1440. As with other intervertebral devices described or contemplated herein, the intervertebral device 1400 utilizes interfacing, interacting or mating surfaces between the second and third elements 1440, 1470, however the surfaces of the intervertebral device 1400 may be curvilinear to encourage at least rotational movement of the third element 1470 with respect to the first and second elements 1410, 1440. Such curvilinear surfaces may allow for portions of the third element 1470 to move at different rates with respect to other portions thereof, while maintaining constant or near constant surface contact between the curvilinear surfaces of the third element 1470 and the second element 1440. More specifically, the third element 1470 may include a plurality of curvilinear surfaces 1478 that are configured or adapted to come in contact along a respective one of a plurality of curvilinear surfaces 1448 of second element 1440. Curvilinear surfaces 1478 may include a first pair of curvilinear surfaces 1478A and a second par of curvilinear surfaces 1478B and these curvilinear surfaces may interface with corresponding curvilinear surfaces 1448A, 1448B of the second element 1440, respectively. Accordingly, as the second element or sliding element 1440 translates between the first end 1412 and the second end 1414 of the base element 1410, the curvilinear surfaces 1448 of the second element 1440 contact and slide along corresponding respective curvilinear surfaces 1478 of the third element 1470 resulting in movement of the element 1470 in at least a vertical direction.

As depicted, translation of sliding element 1440 from the first end 1412 toward the second end 1414 results in movement of the element 1470 in at least a vertical direction away from the base element 1410, the third element 1470 rotating with respect to the first and second elements 1410, 1440. Translation of the sliding element 1440 in a direction from the second end 1414 toward the first end 1412 results in movement of the element 1470 in at least a vertical direction toward the base element 1410, the third element 1470 once again rotating with respect to the first and second elements 1410, 1440, the top surface 1471 of the third element 1470 being substantially parallel with the bottom surface 1420 of the first element 1410 when the device 1400 returns to its collapsed configuration.

Curvilinear surfaces 1448A of the second element 1440 and curvilinear surfaces 1478A of the third element 1470 may define a first circle having a radius R1 (not shown), while curvilinear surface 1448B of the second element and curvilinear surface 1478B of the third element 1470 may define a second circle having a radius R2 (not shown), which is greater than the radius R1. First and second circles are concentric allowing for all interfacing curvilinear surfaces to be in intimate contact during activation. As the second element 1440 moves distally, differences in radii R1 and R2 result in portions of the third element 1470 moving vertically at differing rates. For example, corner portions $1470_{C1}$ and $1470_{C2}$ of the third element 1170 may move vertically at a slower rate than corner portions $1470_{C3}$ and $1470_{C4}$ of the third element 1470, resulting in at least rotational movement of the third element 1470 with respect to the first and second elements 1410, 1440.

As shown in FIG. 53A, when the second element 1440 is in its most proximal position, a minimum height of the third element 1470 is $H_{11-1D}$ and a maximum height of the third element 1470 is $H_{11-1P}$, the top surface 1471 of the third element 1470 forming an angle $1471A_1$ with respect to a bottom surface 1420 of the base element 1410. As shown in FIG. 53B, when the second element 1440 is in its most distal position, a minimum height of the third element 1470 is $H_{11-2D}$ and a maximum height of the third element 1470 is $H_{11-2P}$, the top surface 1471 of the third element 1470 forming an angle $1471A_2$ with respect to a bottom surface of the base element 1410. The height $H_{11-2D}$ and the height $H_{11-2P}$ may range any suitable amount to provide for a desired angle $1471A_2$. As should be understood by one of ordinary skill in the art, the radii R1 and R2 may be selected to provide for larger or smaller rates of rotation of the third element 1470 with respect to the first element 1410.

As with other intervertebral devices described or contemplated herein, the first element or base element 1410 may include a plurality of engaging elements 1456 that protrude from a top inner surface of the bottom portion 1420 of element 1410. Second element 1440 may include a plurality of engaging elements 1450, at least one of the elements 1450 engaging a respective one of the plurality of engaging elements 1456. While depicted as being integral to the respective elements 1410, 1440, the engaging elements 1436, 1450 may be individual parts attached or affixed to the surfaces of the base element 1410 and sliding element 1440, respectively. As with the engaging elements 736, 750 of the intervertebral device 700, the engaging elements 1436, 1450 are depicted as having similar shapes, e.g., triangular portions, however in other configurations, the shapes can be dissimilar, or may be nonsymmetrical along its vertical central axis, passing through the tip of each element 1436, 1450.

As with intervertebral device 700, the intervertebral device 1400 may be configured such that applying a linear force to the sliding element 1440 to translate the element 1440 between the first and second ends 1412, 1414 of base member 1410, results in each engaging element 1450 sliding up and over a corresponding engaging element 1436, and engaging an adjacent engaging element 1436 in the direction of the movement of sliding element 1440. Accordingly, sliding element 1440, while primarily moving along the longitudinal axis of the base element 1410, may also move vertically in accordance with the geometry outline and coupling of the engaging elements 1450, 1456 of the sliding element 1440 and base element 1410, respectively.

The intervertebral device 1400 may further include a plurality of pins 1445 coupled to sliding member 1440 and extending through corresponding openings 1428 in the side portions 1416, 1418 of base element 1410, the openings 1428 may be similar to openings 728 of the intervertebral device 700, as viewed in FIGS. 51A-53B. It is noted that by adjusting the slope or curvilinear shape of each side surface of the engaging elements 1450, 1456 the translational force to move the sliding element 1440 in the presence of a compression force between the top surface 1471 of element 1470 and the bottom portion 1420 of the base element 1410 may differ in accordance with the corresponding engaging element 1450, 1456 shaped surfaces. The geometric shape of each side surface of the engaging elements 1450, 1456, which may be linear or curvilinear, or a combination thereof, may be configured to encourage movement of the sliding element 1440 in a first direction along the longitudinal axis of the base 1410 with respect to movement of the sliding element 1440 in a second opposite direction. In any case, the engaging elements 1450, 1436 are configured, e.g., with suitable shaped surfaces or the like, to become locked or immovable when a compression force exists between the third element 1470 and the base element 1410.

The sliding element 1440 may include a protrusion 1444, similar to protrusion 1144 of the sliding element 1140 of intervertebral device 1100, such protrusion being configured or adapted to slidably interface with a corresponding recessed portion or groove along the inner walls of side portions, respectively, of the third element 1470.

As with vertebral device 700, in the presence of a linear force applied to sliding element 1440 moving the element 1440 toward the distal end 1414, in a ratcheting manner, for example, the engaging elements 1450, 1456 continuously engage and disengage with adjacent opposing engaging elements 1450, 1456. As the element 1440 translates, the third element 1470 moves vertically to increase the overall height, $H_{11}$, of the device 1400. With a compression force applied between the third element 1470 and the base element 1410, e.g. when the device 1400 is positioned between adjacent tissue surfaces, such as two adjacent vertebrae, the engaging elements 1450, 1456 of the sliding element 1440 and base element 1410, respectively, engage and prevent the sliding element 1440 from further translating. For illustration purposes only, the sliding element 1440 of the intervertebral device 1400 may be translated through the use of a tool, such as exemplary tool 1000 described above for example, the distal portion of the sliding element 1440 including protrusions and grooves similar to protrusions 1140P and grooves 1140G, as best viewed in FIGS. 29 and 30, to interface with the tool 1000, for example.

This disclosure provides exemplary embodiments that allow for the generation of a multitude of different intervertebral devices through determining the desired initial and final heights, and an angle of a top surface of the intervertebral device with respect to a bottom surface of said device. In this way, an intervertebral device may be provided that corresponds to any suitable access approach and patient anatomy. For example, certain embodiments may have third elements that rotate about an axis that is substantially perpendicular to a longitudinal axis of the intervertebral device, such as exemplary intervertebral device 1100 and exemplary intervertebral device 1400. Additionally, certain embodiments may have third elements that rotate about an axis that is substantially parallel to a longitudinal axis of the intervertebral device, such as exemplary intervertebral device 1300. However, it should be noted that the rotational axis about which the third element rotates might not be parallel to nor perpendicular to a longitudinal axis of the intervertebral device. For illustration purposes only, such a rotational axis may form a 45-degree angle with a longitudinal axis of the intervertebral device. Such a device is discussed immediately below with respect to FIGS. 54A-56B.

Figure 54A:
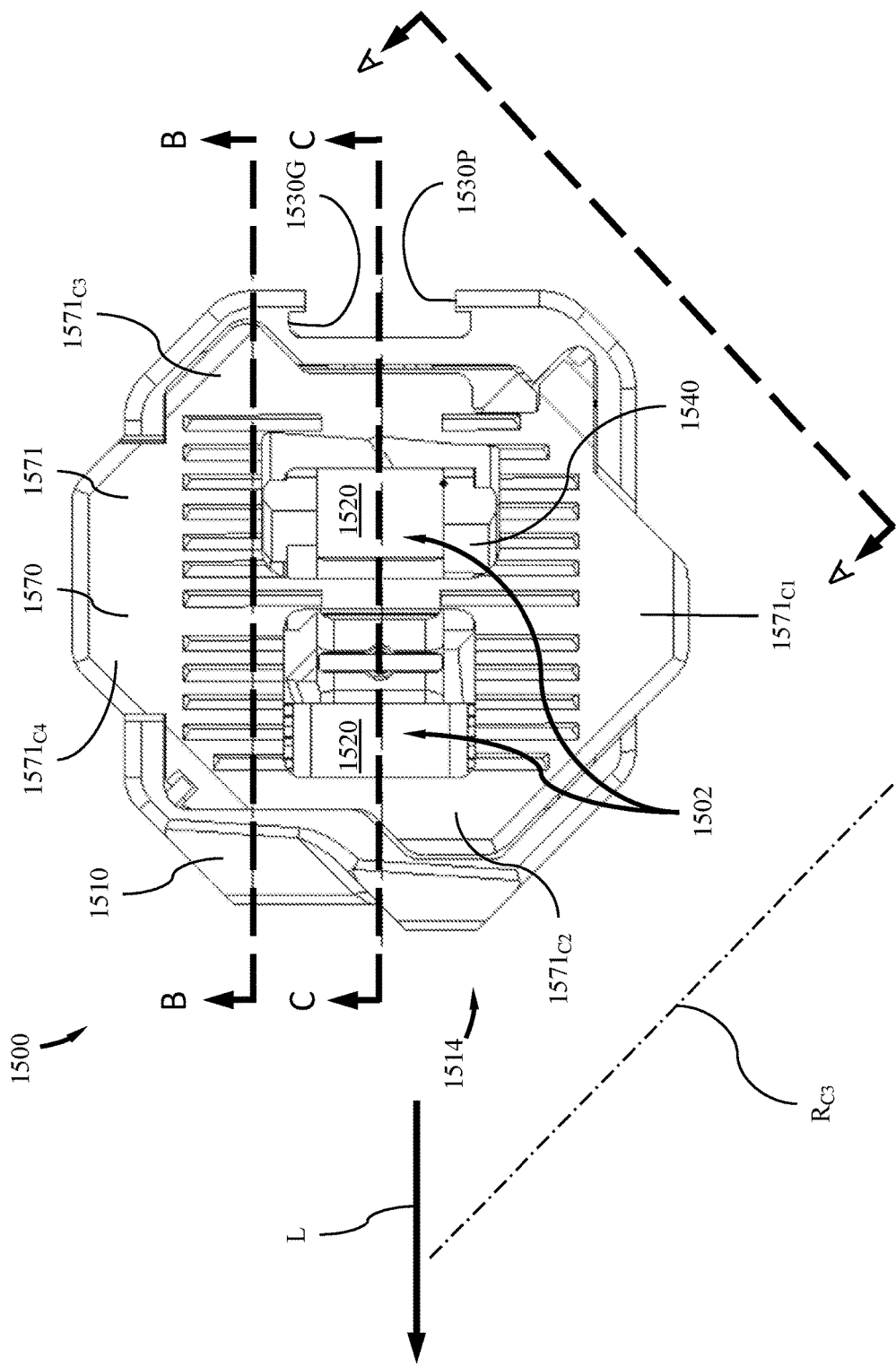
FIG. 54A is a top view of another exemplary intervertebral device.

Turning now to FIG. 54A, yet another exemplary intervertebral device 1500 includes a first or base element 1510, a second or sliding element 1540, and a third or lifting element 1570. The intervertebral device 1500 is generally similar to other intervertebral devices described or disclosed herein, however the first, second and third elements 1510, 1540, 1570 cooperate such that the third element 1570 is adapted to rotate with respect to the other elements 1510, 1540 during operation and along a rotational axis that is nether parallel to nor perpendicular to a longitudinal axis, L, of the intervertebral device 1500.

As with other embodiments described herein, the third element 1570 may include a top surface 1571 that may include first, second, third, and forth corner portions, $1571_{C1}$, $1571_{C2}$, $1571_{C3}$, $1571_{C4}$, respectively, and $1571_C$ collectively. The second element 1540 and the third element 1570 may be adapted such that each of the four corner portions $1570_C$ of the top surface 1571 move at one of a plurality of rates as the second element 1540 translates with respect to the third element 1570. More specifically, each of the first corner portion $1571_{C1}$, the second corner portion $1571_{C2}$, the third corner portion $1571_{C3}$, and the forth corner portion $1571_{C4}$ may have a respective one of a plurality of rates. In this way, for example, the third element 1570 may have a top planar surface 1571 that is angled with respect to a bottom planar surface 1520 of the base element 1510 as the interventional device 1500 transitions from a collapsed configuration to an expanded configuration. Furthermore, as described in greater detail above with respect to intervertebral device 1100A, the top surface 1571 of the third element 1570 may be initially angled with respect to a bottom surface 1520 of the base element 1510 when in a collapsed configuration, such that when the third element 1570 is elevated at least a portion, its top planar surface 1571 may form a desired angle with respect to the bottom planar surface 1520 of the base element 1510.

The intervertebral device 1500 includes a proximal end 1512 and a distal end 1514, and the proximal end 1512 may include geometric structures 1530G, 1530P for positioning the intervertebral device 1500, as described in greater detail above with respect to other embodiments. The first, second, and third elements 1510, 1540, 1570 further cooperate to provide an internal open space or void 1502 for deployment of therapeutic agents, as discussed herein.

Figure 54B:
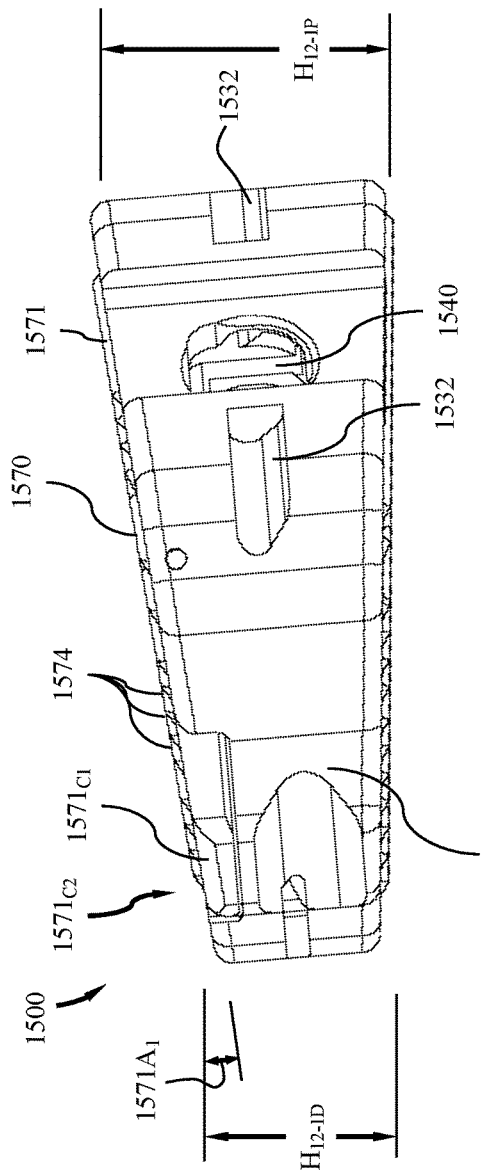
FIGS. 54B and 54C are side elevation views of the exemplary intervertebral device of FIG. 54A.
Figure 54C:
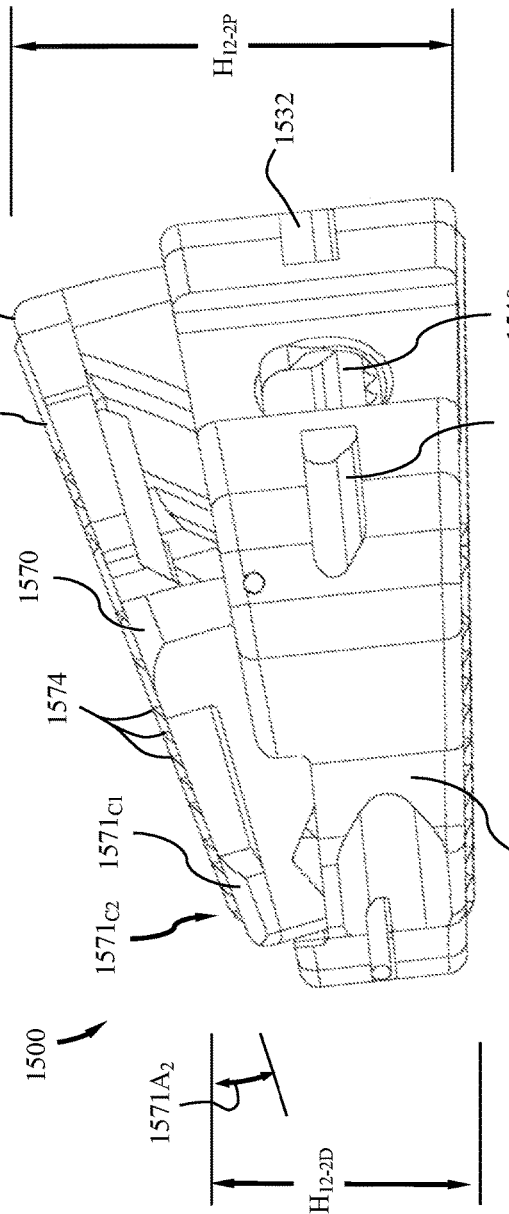
Figure 56A:
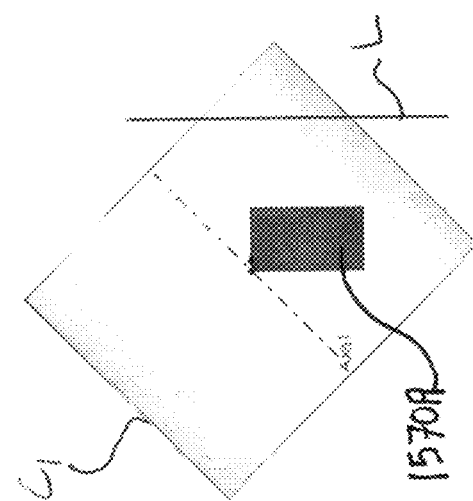
Figure 56B:
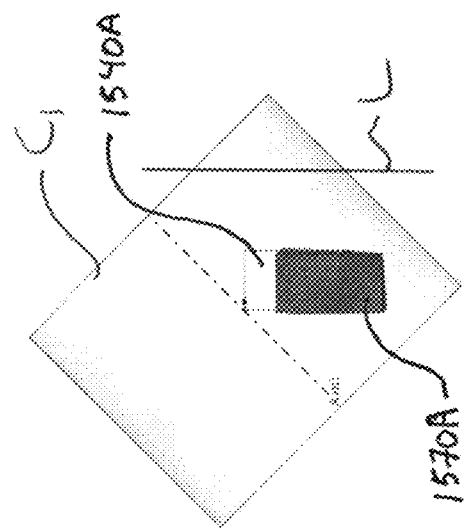
Figure 57A:
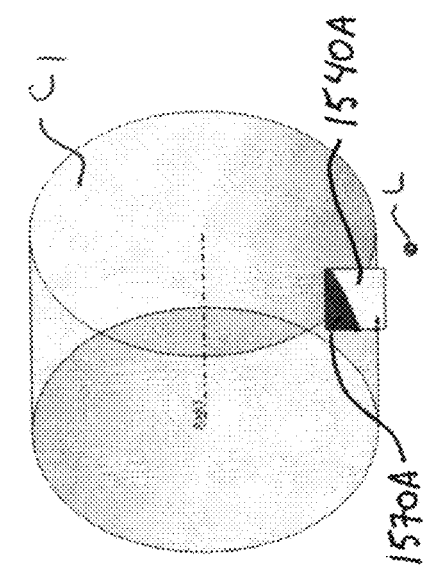
Figure 57B:
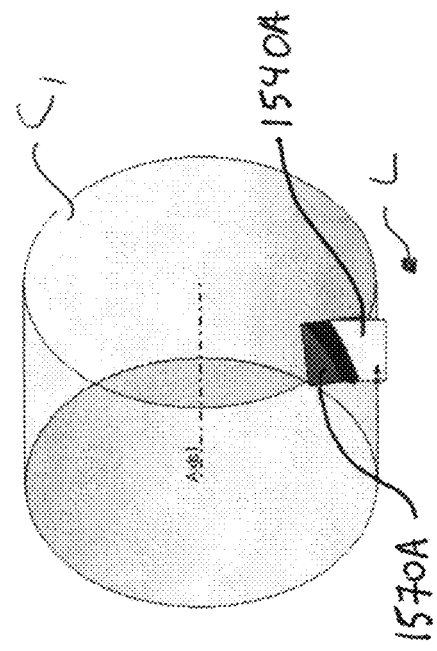

Turning also to FIGS. 54B and 54C, which depict elevation side views of the intervertebral device 1500 as viewed from section line A, the section line A being perpendicular to the axis of rotation $R_{C3}$, in both a collapsed configuration (FIG. 54B) and an expanded configuration (FIG. 54C). The base element 1510 and the sliding element 1540 include various protrusions and grooves to allow for interfacing the device 1500 to a delivery system, such as delivery system 800. For example, the elongated shaft 900 of the delivery system 800 may engage a groove 1530G and a protrusion 1530P of the second element 1540, in accordance with the discussion above with respect to groove 730G and protrusion 730P of the intervertebral device 700. The delivery system 800 may further include portions that interface with one or more recesses 1532 to fixedly hold the intervertebral device 1500 in contact with the delivery system 800. Accordingly, when the elongate shaft 900 is translated toward distal end 1514 of the intervertebral device 1500, in a direction parallel to longitudinal axis L of the device 1500 for example, the sliding or second element 1540 also translates in a distal direction. As the sliding element 1540 moves distally various curvilinear surfaces of the sliding element 1540 cooperate with corresponding various curvilinear surfaces of the lifting element 1570 such that the top surface 1571 moves in a rotationally vertical direction away from the base element 1510, for example, as described in greater detail below.

Turning now to FIG. 55A, since the intervertebral device 1500 includes a sloped top surface 1571 as compared to a bottom surface 1520 of the base 1510, in a collapsed position the intervertebral device 1500 may have a first distal height, for example near corner $1571_{C2}$, $H_{12-1D}$ and a first proximal height, for example near corner $1571_{C3}$, $H_{12-1P}$. Note that these heights are for illustration purposes only and are defined relative to the specific elevation views of FIGS. 54B and 54C and, therefore, are not necessarily the distal most or proximal most portions of the device 1500. The top surface 1571 may define an angle $1571A_1$ with respect to a line, $R_P$, which is perpendicular to the axis of rotation, $R_{C3}$, and parallel to the bottom surface 1520 of the base 1510. In the collapsed configuration the sliding element 1540 is in its most proximal position.

Turning now to FIG. 54C, the sliding element 1540 has moved from its most proximal position to its most distal position, the third element 1570 rotating with respect to the base element 1510 such that the top surface 1571 has a second distal height $H_{12-2D}$ and a second proximal height $H_{12-2P}$. The top surface 1571 of the third element 1570 forms a second angle $1571A_2$ with respect to a line, $R_P$, which is perpendicular to the axis of rotation, $R_{C3}$, and parallel to the bottom surface 1520 of the base 1510.

Turning also to FIGS. 55A and 55B, in which perspective views of the exemplary intervertebral device 1500 are depicted in cut view along section B-B of FIG. 54A, as with other intervertebral devices described or contemplated herein, and discussed above, the elements 1510, 1540, 1570 cooperate such that the intervertebral device 1500 has a geometric height, $H_{12}$. The height, $H_{12}$, of the intervertebral device 1500 and may have a minimum value in a collapsed configuration as depicted in FIG. 55A, generally referred to as a height $H_{12-1}$, and may have a maximum value in an expanded configuration as depicted in FIG. 55B, generally referred to as height $H_{12-2}$. More specifically, the intervertebral device 1500 in a collapsed configuration has a first distal height $H_{12-1D}$ and a first proximal height $H_{12-1P}$, and in an expanded configuration has a second distal height $H_{12-2D}$ and a second proximal height $H_{12-2P}$.

The first element 1510, also referred to as base 1510 or base element 1510, may be configured to provide a base or outer structure for the intervertebral device 1500, and includes a first end 1512, and a second end 1514. A bottom portion 1520 includes one or more openings 1522 (not shown), allowing for one or more therapeutic agents to pass therethrough, for example. The second and third elements 1540, 1570 may also include similar openings for the same or differing purposes. The proximal end 1512 may include an opening 1530 for passing a portion of one or more tools utilized for delivery of said therapeutic materials, or expanding, contracting, or locking the intervertebral device 1500 in a specific configuration, for example. Such an opening 1530 may be similar, for example, to opening 1330 of the intervertebral device 1300, as depicted in FIG. 46A. As with other intervertebral devices described or contemplated herein, utilizing a single connecting point on the device 1500 for interfacing with a tool that can allow for other tools to be easily attached, tools for expanding, contracting or locking the device 1500 in a specific configuration, or tools for delivery of therapeutic materials, provides for a more efficient system, allowing a user to more easily place, position, manipulate, and operate the device 1500.

The intervertebral device 1500 may be expanded or contracted to any suitable height, $H_{12}$, between a first collapsed heights $H_{12-1D}$, $H_{12-1P}$, as depicted in FIG. 55A, and second expanded heights $H_{12-2D}$ and $H_{12-2P}$, as depicted in FIG. 55B. As described in greater detail below, since the third element 1570 is configured to rotate, as well as move vertically, with respect to the first and second elements 1510, 1540 as the intervertebral device 1500 transitions from a collapsed configuration to an expanded configuration, a distal portion of the third element 1570 may have a first expanded height $H_{12-2D}$ and a proximal portion of the third element 1570 may have a second height $H_{12-2P}$. For example, the intervertebral device 1500 may be expanded from a first position, having minimum distal height of $H_{12-1D}$ and a minimum proximal height $H_{12-1P}$ as depicted in FIG. 55A, to a second position, having a maximum distal height of $H_{12-2D}$ and a maximum proximal height of $H_{12-2P}$ as depicted in FIG. 55B, or another position therebetween, and locked in that corresponding position. For illustration purposes, the height $H_{12}$, may range from about 12 mm to about 25 mm, and the angle may range from between about 0 degrees to about 20 degrees.

The proximal end 1512 may also include structures, such as protrusions 1530P and grooves 1530G, best views in FIG. 54A, which may allow for attachment points to a delivery system (not shown), as described above with respect to delivery device 800 of FIG. 6, for example, in a similar manner as intervertebral device 1100, for example. In this way, such therapeutic agents or materials may contact surrounding tissues, such as bone tissue, encouraging healing. The tubular members to perform these functions may be the same tubular member or different tubular members.

As with other intervertebral devices described or contemplated herein, the third element 1570 may be slidably interfaced to the first and second elements 1510, 1540 such that the third element 1570 at least slides vertically with respect to the first and second elements 1510, 1540, as well as rotationally. The third element 1570 may include one or more openings 1572 in the top portion or surface 1571 thereof to allow for passage or introduction of therapeutic elements or bone growth enhancing materials therethrough. The top portion 1571 may include one or more protrusions 1574 that may aide in holding the top portion 1571 immobile with respect to adjacent structures or biological tissue, such as vertebrae structures for example. While only a few protrusions 1574 are identified, additional or less protrusions 1574 may be utilized. Such protrusion structures 1574 may be constructed from any biocompatible material and in any suitable form. Additionally, a bottom portion or surface 1520 of base 1510 may include one or more protrusions 1521. Protrusions 1521 may be, for example, similar to protrusions 1574, which may aide in holding a bottom portion 1520 immobile with respect to adjacent structures or biological tissue, such as vertebral structures for example.

As with other intervertebral devices described or contemplated herein, a void or space 1502 is defined by the first, second, and third elements 1510, 1540, 1570 of the intervertebral device 1500, the void 1502 increasing as the device 1500 transitions from a collapsed configuration to an expanded configuration. In this way, once the device 1500 is deployed, one or more therapeutic agents may be positioned within the void 1502. As described above, such therapeutic agents may further flow out of the void 1502 via additional openings, such as openings 1572 and 1522, positioned about the elements 1510, 1540, 1570.

In operation, the third element 1570 of intervertebral device 1500 at least rotates with respect to the first and second elements 1510, 1540. As with other intervertebral devices described or contemplated herein, the intervertebral device 1500 utilizes interfacing, interacting or mating surfaces between the second and third elements 1540, 1570, however the surfaces of the intervertebral device 1500 may be curvilinear to encourage at least rotational movement of the third element 1570 with respect to the first and second elements 1510, 1540. Such curvilinear surfaces may allow for portions of the third element 1570 to move at different rates with respect to other portions thereof, while maintaining constant or near constant surface contact between the curvilinear surfaces of the third element 1570 and the second element 1540. More specifically, the third element 1570 may include a plurality of curvilinear surfaces 1578 that are configured or adapted to come in contact along a respective one of a plurality of curvilinear surfaces 1548 of second element 1540. Curvilinear surfaces 1578 may include a first curvilinear surface 1578A (not shown) and a second curvilinear surface 1578B along a distal portion of the third element 1570, and a third curvilinear surface 1578C (not shown) and a forth curvilinear surface 1578D along a proximal portion of the third element 1570. These curvilinear surfaces 1578 may interface with corresponding curvilinear surfaces 1548A (not shown), 1548B, 1548C (not shown), and 1548D of the second element 1540, respectively. Accordingly, as the second element or sliding element 1540 translates between the first end 1512 and the second end 1514 of the base element 1510, the curvilinear surfaces 1548 of the second element 1540 contact and slide along corresponding respective curvilinear surfaces 1578 of the third element 1570 resulting in movement of the third element 1570 in a rotationally vertical direction with respect to the base element 1510 and the sliding element 1540.

As depicted, translation of sliding element 1540 from the first end 1512 toward the second end 1514 results in movement of the element 1570 in at least a vertical direction away from the base element 1510, the third element 1570 rotating with respect to the first and second elements 1510, 1540. Translation of the sliding element 1540 in a direction from the second end 1514 toward the first end 1512 results in movement of the element 1570 in at least a vertical direction toward the base element 1510, the third element 1570 once again rotating with respect to the first and second elements 1510, 1540, the top surface 1571 of the third element 1570 being substantially parallel with the bottom surface 1520 of the first element 1510 when the device 1500 returns to its collapsed configuration.

Turning to FIGS. 56 through 60, the characteristics of curvilinear surfaces 1578. 1548 of the intervertebral device 1500 will be discussed in greater detail. In particular, each of the FIGS. 56A, 57A, 58A, and 59A depict a portion 1540A of the second element 1540 and a portion 1570A of the third element 1570 in a first position, while FIGS. 56B, 57B, 58B, and 59B depict the portion 1570A of the third element 1570 in a second position relative to the portion 1540A of the second element 1540, which maintains its first position for this discussion. The various figures depict the curvilinear surfaces 1578, 1548 of the portions 1570A, 1540A from different views relative the intervertebral device 1500. More specifically, FIGS. 56A and 56B depict a top view of a portion of the intervertebral device 1500 along its longitudinal axis, L; FIGS. 57A and 57B depict a front view of the portion of the intervertebral device 1500 along its longitudinal axis, L; FIGS. 58A and 58B depict a left side view of the portion of the intervertebral device 1500 along its longitudinal axis, L; and FIGS. 59A and 59B depict an isometric view of the portion of the intervertebral device 1500.

As depicted, the curvilinear surfaces 1578, 1548 are perfectly coplanar with a cylindrical structure, C1, having an axis, Axis 1, which is also the rotational axis about which the third element 1570 rotates. In this example, Axis 1 is approximately 45 degrees from the longitudinal axis, L, of the intervertebral device 1500. Accordingly, as the portion of the third element 1570 moves relative to the second element 1540, the third element merely rotates about Axis 1 while moving generally parallel to the longitudinal axis, L, of the intervertebral device 1500, as shown in FIGS. 56B, 57B, 58B, and 59B. Alternatively, one can describe this movement as, first, rotating about Axis 1 and then, second, moving parallel to Axis 1. This also perfectly mimics the outcome of the two parts if the bottom part moves along its longitudinal axis and the top part is held in place but free to rotate and translate upward.

Figure 60:
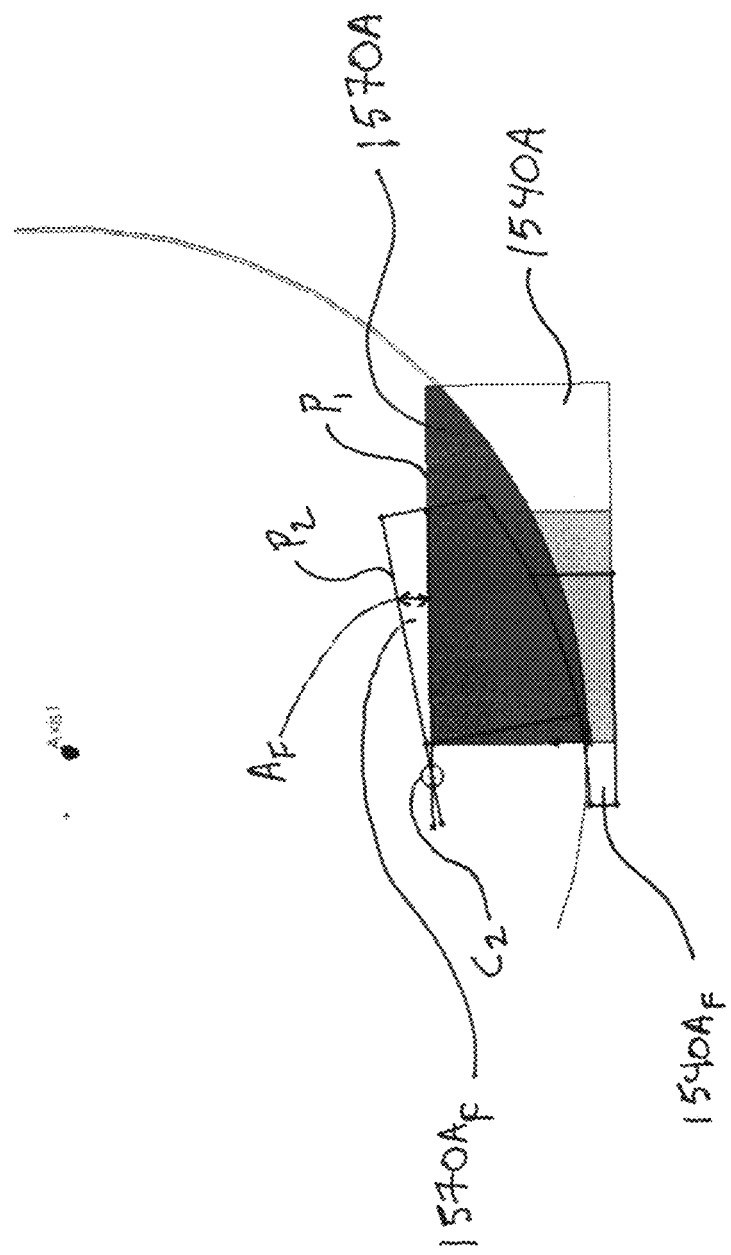

Turning to FIG. 60, initial location of the two portions 1570A, 1540A are depicted, with the final position is provided in outline view of the sides of the two portions after the portion 1540A is moved and the top portion 1570A is allowed to only rotate and translate upward, the final view of portion 1570A being $1570A_F$ and the final view of portion 1540A being $1540_F$. A top surface of the portion 1570A includes a planar surface $P_1$, and the top surface of the portion $1570A_F$ includes a planar surface $P_2$. The circle, C2, defines the intersection of the two planes P1 and P2, an angle, $A_F$, between the two planes $P_1$ and $P_2$ defining the angle between the top surface of the third element 1570F in its final position and the top surface of the third element 1570A. Because the two portions, 1570A, 1540A, move in continuous motion all positions in between the initial and final positions will be continuous.

The angle between Axis 1 and the longitudinal axis, L, of the intervertebral device 1500 and the location of Axis 1 relative to the intervertebral device 1500 can all be varied to bring about a desired angle of rotation and location of rotation, e.g., C2 of FIG. 60, of the top part.

The common surface between portions 1570A, 1540A can be a plurality of surfaces that are cylindrical and centered about the same axis, such as Axis 1. In this way the portion 1570A, relative to the portion 1540A, can always be rotated about Axis 1 and moved in the direction parallel to the longitudinal axis, L. Alternatively, one can describe this movement as, first, rotating about Axis 1 and then, second, moving parallel to Axis 1, thus keeping all the common surfaces between the two parts in constant contact. This completely mimics the sliding element 1540 and third element 1570 on intervertebral device 1500.

As with other intervertebral devices described or contemplated herein, the first element or base element 1510 may include a plurality of engaging elements 1536 that protrude from a top inner surface of the bottom portion 1520 of element 1510. Second element 1540 may include a plurality of engaging elements 1550, at least one of the elements 1550 engaging a respective one of the plurality of engaging elements 1536. While depicted as being integral to the respective elements 1510, 1540, the engaging elements 1536, 1550 may be individual parts attached or affixed to the surfaces of the base element 1510 and sliding element 1540, respectively. As with the engaging elements 736, 750 of the intervertebral device 700, the engaging elements 1536, 1550 are depicted as having similar shapes, e.g., triangular portions, however in other configurations, the shapes can be dissimilar, or may be nonsymmetrical along its vertical central axis, passing through the tip of each element 1536, 1550.

As with intervertebral device 700, the intervertebral device 1500 may be configured such that applying a linear force to the sliding element 1540 to translate the element 1540 between the first and second ends 1512, 1514 of base member 1510, results in each engaging element 1550 sliding up and over a corresponding engaging element 1536, and engaging an adjacent engaging element 1536 in the direction of the movement of sliding element 1540. Accordingly, sliding element 1540, while primarily moving along the longitudinal axis of the base element 1510, may also move vertically in accordance with the geometry outline and coupling of the engaging elements 1550, 1536 of the sliding element 1540 and base element 1510, respectively.

The intervertebral device 1500 may further include a plurality of pins 1545 coupled to sliding member 1540 and extending through corresponding openings 1528 in the side portions 1516, 1518 of base element 1510, the openings 1528 may be similar to openings 728 of the intervertebral device 700.

The intervertebral devices described herein may be made from any suitable biocompatible material, including but not limited to metals, metal alloys (e.g. stainless steel) and polymers (e.g. polycarbonate), and may be formed using any appropriate process, such as screw-machining or molding (e.g. injection molding). The intervertebral devices herein may be sized for minimally invasive procedures having operating lumens at about 14 mm or less.

It should be understood that features of any one of the above-described intervertebral devices described herein may be applied to any other of the above-described intervertebral devices, as appropriate. The intervertebral devices described herein may be made from any suitable biocompatible material, including but not limited to metals, metal alloys (e.g. stainless steel) and polymers (e.g., polycarbonate), and may be formed using any appropriate process, such as screw-machining or molding (e.g., injection molding). The intervertebral devices herein may be sized for minimally invasive procedures having operating lumens at about 12 mm or less.

The invention claimed is:

1. A device comprising:
    a base element, the base element having a distal end and a proximal end;
    a first body portion slidably attached to the base element and configured to move in at least a first direction with respect to the base element, the first body portion including a first plurality of curvilinear surfaces,
    a second body portion slidably attached to the base element and configured to move in at least a second direction with respect to the base element, the second body portion including a second plurality of curvilinear surfaces,
    each of the first plurality of curvilinear surfaces configured to couple with a respective one of the second plurality of curvilinear surfaces, such that the second body portion at least rotates with respect to the base element as the first body portion moves in the first direction,
    the first body portion including a first engaging element and the base element including a plurality of second engaging elements, the first engaging element configured to couple with first and second ones of the plurality of second engaging elements, the first engaging element and the plurality of second engaging elements being configured such that the coupling of the first engaging element and the plurality of second engaging elements prevents movement of the second body portion in a third direction with respect to the base element when a compression force is present between a top surface of the second body portion and a bottom surface of the base element,
    the first body portion configured to move along a path extending from a first point where the first body portion abuts the proximal end of the base element to a second point where the first body portion abuts the distal end of the base element, the proximal end of the base element being configured to prevent further proximal movement of the first body portion, and the distal end of the base element being configured to prevent further distal movement of the first body portion, each position of the first body portion along the path corresponding to one of a plurality of heights of the device, each one of the plurality of heights being different from the remaining ones of the plurality of heights.

2. The device of claim 1, wherein the device includes a longitudinal axis parallel to the first direction and the second body portion includes an axis of rotation, the axis of rotation of the second body portion neither being perpendicular nor parallel to the longitudinal axis of the device.

3. The device of claim 1, wherein a shape of each of a first pair of the first curvilinear surfaces of the first body portion are similar.

4. The device of claim 3, wherein each of a second pair of the first curvilinear surfaces of the first body portion are similar, the second pair being different from the first pair.

5. The device of claim 1, wherein each of the first plurality of curvilinear surfaces are different.

6. A kit comprising: the device of claim 1, and a delivery system, the delivery system including an attachment assembly having a lumen therethrough, the attachment assembly configured to removably attach to the base element and position the device.

7. The kit of claim 6, wherein the delivery system further includes an expansion tool having an elongate shaft, a distal end of the elongate shaft configured to pass through the lumen of the attachment assembly and removably attach to the first body portion, the expansion tool being configured to translate the elongate shaft and the first body portion attached thereto.

8. The kit of claim 6, wherein the delivery system further includes an insertion assembly having an elongate member, the elongate member of the insertion assembly being slidably coupled to the lumen of the attachment tool, a distal end of the elongate member configured to translate through the lumen of the attachment tool.

9. The kit of claim 8, wherein the base element, the first body portion, and the second body portion are configured to define a void, the distal end of the elongate member configured to translate within the void.

10. The device of claim 1, wherein the second body portion includes the top surface having a first corner portion, a second corner portion, a third corner portion and a fourth corner portion, each of the first corner portion, second corner portion, third corner portion, and fourth corner portion moving at a corresponding one of a plurality of rates as the second body portion moves in the second direction, the plurality of rates being selected such that the top surface forms an angle with respect to the bottom surface of the base element as the second body portion moves in the second direction.

11. The device of claim 10, wherein each of the plurality of rates are different, such that the top surface of the second body portion forms a complex angle with respect to the bottom surface of the base.

12. The device of claim 1, wherein the third direction is substantially opposite to the second direction.

* * * * *